United States Patent
Reiser et al.

(10) Patent No.: US 9,278,978 B2
(45) Date of Patent: *Mar. 8, 2016

(54) 6-ALKYNYL PYRIDINE

(71) Applicants: Ulrich Reiser, Vienna (AT); James Madden, Reading (GB)

(72) Inventors: Ulrich Reiser, Vienna (AT); James Madden, Reading (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,692

(22) Filed: Aug. 20, 2014

(65) Prior Publication Data
US 2015/0057295 A1    Feb. 26, 2015

(30) Foreign Application Priority Data
Aug. 23, 2013    (EP) ..................................... 13181577

(51) Int. Cl.
| | |
|---|---|
| C07D 491/048 | (2006.01) |
| C07D 213/75 | (2006.01) |
| C07D 401/04 | (2006.01) |
| C07D 401/14 | (2006.01) |
| C07D 471/04 | (2006.01) |
| C07D 473/00 | (2006.01) |
| C07D 487/04 | (2006.01) |
| C07D 401/02 | (2006.01) |
| C07D 403/02 | (2006.01) |
| C07D 403/14 | (2006.01) |
| A61K 31/519 | (2006.01) |
| A61K 31/444 | (2006.01) |
| A61K 31/435 | (2006.01) |

(52) U.S. Cl.
CPC .......... *C07D 491/048* (2013.01); *A61K 31/435* (2013.01); *A61K 31/444* (2013.01); *A61K 31/519* (2013.01); *C07D 213/75* (2013.01); *C07D 401/02* (2013.01); *C07D 401/04* (2013.01); *C07D 401/14* (2013.01); *C07D 403/02* (2013.01); *C07D 403/14* (2013.01); *C07D 471/04* (2013.01); *C07D 473/00* (2013.01); *C07D 487/04* (2013.01)

(58) Field of Classification Search
None
See application file for complete search history.

(56) References Cited

FOREIGN PATENT DOCUMENTS

| WO | 2005097791 A1 | 10/2005 |
|---|---|---|
| WO | 2008073306 A1 | 6/2008 |
| WO | 2013127729 A1 | 9/2013 |

OTHER PUBLICATIONS

International Search Report, form PCT/ISA/210, and Written Opinion, PCT/ISA/237, for corresponding application PCT/EP2014/067859, date of mailing Oct. 10, 2014.

*Primary Examiner* — Samantha Shterengarts
(74) *Attorney, Agent, or Firm* — Michael P. Morris; Alan R. Stempel

(57) ABSTRACT

This invention relates to 6-alkynyl-pyridine of general formula (I)

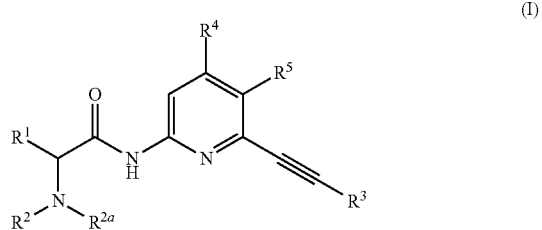

their use as SMAC mimetics, pharmaceutical compositions containing them, and their use as a medicaments for the treatment and/or prevention of diseases characterized by excessive or abnormal cell proliferation and associated conditions such as cancer.
The groups $R^1$ to $R^5$ have the meanings given in the claims and in the specification.

16 Claims, No Drawings

6-ALKYNYL PYRIDINE

This invention relates to compounds of the general formula (I)

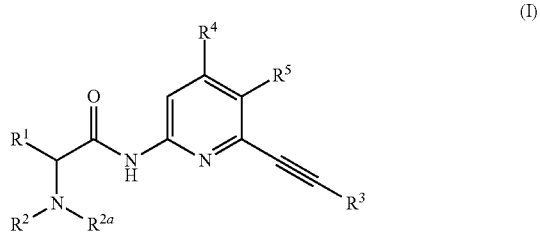

wherein the groups $R^1$ to $R^5$ have the meanings given below in the specification. The compounds of the invention are suitable for the treatment of diseases characterized by excessive or abnormal cell proliferation, pharmaceutical preparations containing such compounds and their uses as a medicament. The compounds of the invention modulate IAP activity.

BACKGROUND OF THE INVENTION

Apoptosis, a form of programmed cell death, typically occurs in the normal development and maintenance of healthy tissues in multicellular organisms. It is a complex process, which results in the removal of damaged, diseased or developmentally redundant cells, without signs of inflammation or necrosis. Apoptosis thus occurs as a normal part of development, the maintenance of normal cellular homeostasis, or as a consequence of stimuli such as chemotherapy and radiation.

The intrinsic apoptotic pathway is known to be deregulated in cancer and lymphoproliferative syndromes, as well as autoimmune disorders such as multiple sclerosis and rheumatoid arthritis. Additionally, alterations in a host apoptotic response have been described in the development or maintenance of viral and bacterial infections. Cancer cells gain the ability to overcome or circumvent apoptosis and continue with inappropriate proliferation despite strong pro-apoptotic signals such as hypoxia, endogenous cytokines, radiation treatments and chemotherapy. In autoimmune disease, pathogenic effector cells can become resistant to normal apoptotic cues. Resistance can be caused by numerous mechanisms, including alterations in the apoptotic machinery due to increased activity of anti-apoptotic pathways or expression of anti-apoptotic genes. Thus, approaches that reduce the threshold of apoptotic induction in cancer cells by overcoming resistance mechanisms may be of significant clinical utility.

Caspases serve as key effector molecules in apoptosis signaling. Caspases (cysteine containing aspartate specific proteases) are strong proteases and once activated, digest vital cell proteins from within the cell. Since caspases are highly active proteases, tight control of this family of proteins is necessary to prevent premature cell death. In general, caspases are synthesized as largely inactive zymogens that require proteolytic processing for activation. This proteolytic processing is only one of the ways in which caspases are regulated. The second mechanism of regulation is through a family of proteins that bind and inhibit caspases.

One family of molecules that inhibit caspases are the Inhibitors of Apoptosis (IAP) (Deveraux et al., J Clin Immunol (1999), 19: 388-398). IAPs were originally discovered in baculovirus by their ability to substitute for P35 protein function, an anti-apoptotic gene (Crook et al. (1993) J Virology 67, 2168-2174). Human IAPs are characterized by the presence of one to three homologous structural domains known as baculovirus IAP repeat (BIR) domains. Some IAP family members also contain a RING zinc finger domain at the C-terminus, with the capability to ubiquitylate target proteins via their E3 ligase function. The human IAPs, XIAP, HIAP1 (also referred to as cIAP2), and HIAP2 (cIAP1) each have three BIR domains, and a carboxy terminal RING zinc finger. Another IAP, NAIP, has three BIR domains (BIR1, BIR2 and BIR3), but no RING domain, whereas Livin, TsIAP and MLIAP have a single BIR domain and a RING domain. The X chromosome-linked inhibitor of apoptosis (XIAP) is an example of an IAP, which can inhibit the initiator caspase Caspase-9, and the effector caspases, Caspase-3 and Caspase-7, by direct binding. XIAP can also induce the degradation of caspases through the ubiquitylation-mediated proteasome pathway via the E3 ligase activity of a RING zinc finger domain Inhibition of Caspase-9 is mediated by the BIR3 domains of XIAP, whereas effector caspases are inhibited by binding to the linker-BIR2 domain. The BIR domains also mediate the interactions of IAPs with tumor necrosis factor-receptor associated factor (TRAFs)-I and -2, and with TAB1, adaptor proteins affecting survival signaling through NFkB activation. IAP proteins can thus function as direct brakes on the apoptosis cascade by inhibiting active caspases or by redirecting cellular signaling to a pro-survival mode. Survivin is another member of the IAP family of antiapoptotic proteins. It is shown to be conserved in function across evolution as homologues of the protein are found both in vertebrates and invertebrates.

Cancer cells and cells involved in autoimmune disease may avoid apoptosis by the sustained over-expression of one or more members of the IAP family of proteins. For example, IAP overexpression has been demonstrated to be prognostic of poor clinical outcome in multiple cancers, and decreased IAP expression through RNAi strategies sensitizes tumor cells to a wide variety of apoptotic insults including chemotherapy, radiotherapy and death receptor ligands. For XIAP, this is shown in cancers as diverse as leukemia and ovarian cancer. Over expression of cIAP1 and cIAP2 resulting from the frequent chromosome amplification of the 11q21-q23 region, which encompasses both genes, has been observed in a variety of malignancies, including medulloblastomas, renal cell carcinomas, glioblastomas, and gastric carcinomas.

The interaction between the baculoviral IAP repeat-3 (BIR3) domain of X-linked inhibitor of apoptosis (XIAP) and caspase-9 is of therapeutic interest because this interaction is inhibited by the NH2-terminal seven-amino-acid residues of the so-called "second mitochondrial-derived activator of caspase" (in short and hereinafter Smac), a naturally occurring antagonist of IAPs. Small-molecule Smac mimetics have been generated anticipating efficacy in cancer by reconstituting apoptotic signaling.

Thus, there is the need to provide SMAC mimetics useful for the prevention and/or treatment of diseases characterized by excessive or abnormal cell proliferation, such as cancer.

DETAILED DESCRIPTION OF THE INVENTION

The present invention relates to compounds of formula (I)

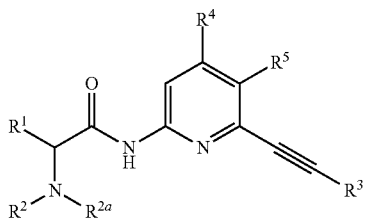

(I)

wherein $R^1$ to $R^5$ are as defined in the description. The compounds according to formula (I) act as Smac mimetics. Thus, the compounds of the invention may be used for example for the treatment of diseases which are characterized by an increased apoptosis resistance due to IAP function. Preferably, the compounds of the invention can be used in the treatment of cancer.

The present invention therefore relates to compounds of general formula (I)

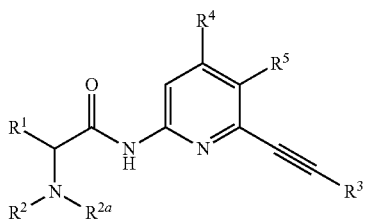

(I)

wherein,
$R^1$ is selected from —$C_{1-3}$alkyl, —$C_{1-3}$haloalkyl and —H;
$R^2$ is selected from —$C_{1-3}$alkyl or —H;
$R^{2a}$ is selected from —$C_{1-3}$alkyl or —H;
$R^3$ is selected from phenyl and 5-12 membered heteroaryl, each of which group can be optionally and independently substituted with one or more groups independently selected from $R^6$ or
$R^3$ is 8-12 membered aromatic heterocyclyl, each of which group can be optionally and independently substituted with one or more groups independently selected from =O and $R^6$;
$R^4$ is selected from phenyl and 5-12 membered heteroaryl, each of which group can be optionally substituted with one or more groups independently selected from $R^7$ or
$R^4$ is 8-12 membered aromatic heterocyclyl, each of which group can be optionally substituted with one or more groups independently selected from =O and $R^7$;
$R^5$ is selected from —H, halogen, —O—$C_{1-3}$alkyl and 5-6 membered heteroaryl;
$R^6$ is selected from halogen, —$C_{1-3}$alkyl, —O—$C_{1-3}$alkyl, cyano, 5-6 membered heteroaryl, wherein the heteroaryl group can be optionally substituted with —$C_{1-3}$alkyl, —O—$C_{1-3}$alkyl or halogen;
$R^7$ is selected from halogen, —$C_{1-3}$alkyl, —$C_{1-3}$haloalkyl and —O—$C_{1-3}$alkyl or cyano;
and wherein the compounds of formula (I) may optionally be present in the form of salts.

In a preferred embodiment the invention relates to compounds of formula (I), wherein $R^1$ is —$CH_3$ or —$CH_2$—$CH_3$.

In a preferred embodiment the invention relates to compounds of formula (I), wherein $R^2$ is —$CH_3$ or —$CH_2$—$CH_3$.

In a preferred embodiment the invention relates to compounds of formula (I), wherein $R^{2a}$ is —H.

In a preferred embodiment the invention relates to compounds of formula (I), wherein $R^3$ is selected from phenyl,

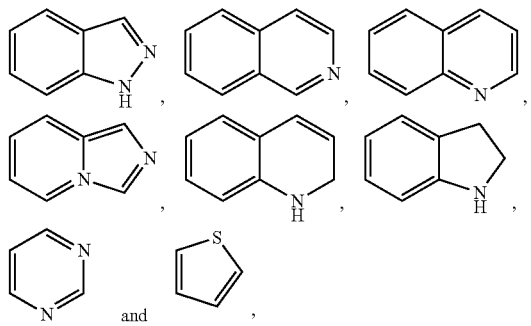

each of which groups can be optionally substituted as defined herein below and above.

In a preferred embodiment the invention relates to compounds of formula (I), wherein $R^3$ is selected from phenyl,

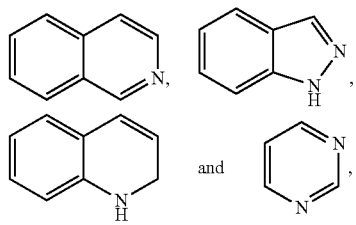

each of which group can be optionally substituted as defined herein above and below.

In a preferred embodiment the invention relates to compounds of formula (I), wherein $R^3$ is selected from phenyl,

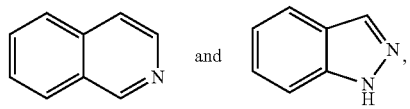 [SMILES: c1ccc2cnccc2c1 ; c1ccc2[nH]ncc2c1]

each of which group can be optionally substituted as defined herein above and below.

In a preferred embodiment the invention relates to compounds of formula (I), wherein $R^4$ is selected from phenyl, pyridyl,

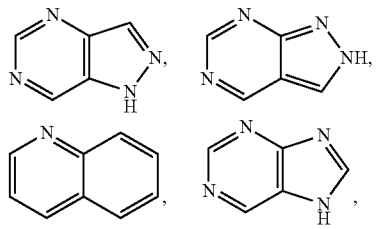

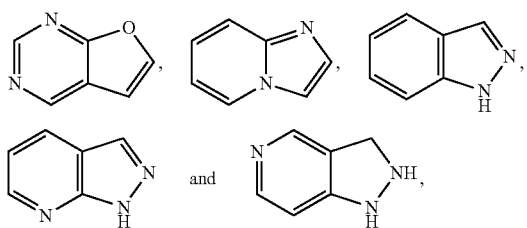

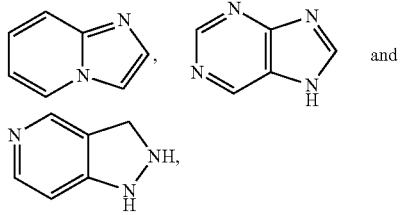

each of which groups can be optionally and independently substituted as defined herein below and above.

In a preferred embodiment the invention relates to compounds of formula (I), wherein $R^4$ is selected from phenyl, pyridyl,

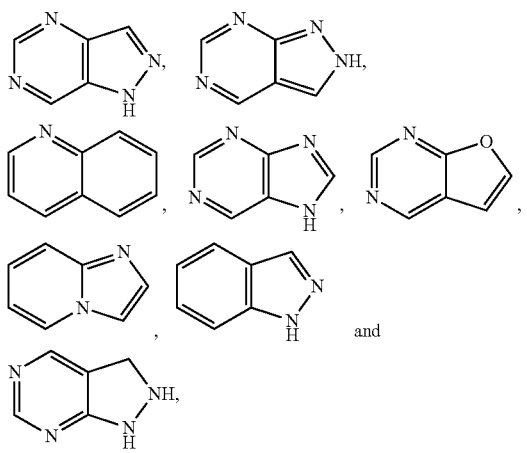

each of which groups can be optionally and independently substituted as defined herein below and above.

In a preferred embodiment the invention relates to compounds of formula (I), wherein $R^4$ is selected from phenyl, pyridyl,

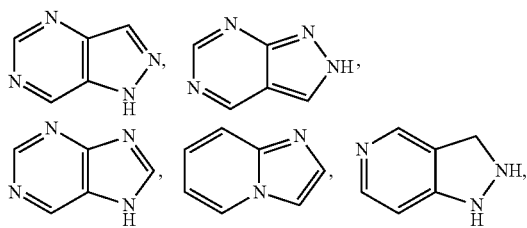

each of which groups can be optionally and independently substituted as defined herein below and above.

In a preferred embodiment the invention relates to compounds of formula (I), wherein $R^4$ is selected from

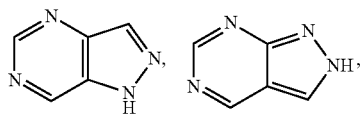

each of which groups can be optionally and independently substituted as defined herein above and below.

In a preferred embodiment the invention relates to compounds of formula (I), wherein $R^5$ is selected from —H, —Cl, —O—CH$_3$ and pyrimidinyl.

In a preferred embodiment the invention relates to compounds of formula (I), wherein $R^5$ is —H.

In a preferred embodiment the invention relates to compounds of formula (I), wherein $R^3$ is substituted with =O or $R^6$, wherein $R^6$ is selected from —F, —CH$_3$ and —O—CH$_3$,

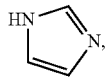

which imidazole can be optionally substituted with —CH$_3$.

In a preferred embodiment the invention relates to compounds of formula (I), wherein $R^4$ is substituted with =O or $R^7$, wherein $R^7$ is selected from —F, —CH$_3$ and —O—CH$_3$.

In another aspect the invention relates to compounds of general formula (I) or of anyone of the embodiments as disclosed above for use in the treatment of cancer.

In another aspect the invention relates to compounds of general formula (I) or of anyone of the embodiments as disclosed above—or the pharmaceutically acceptable salts thereof—for use as medicaments.

In another aspect the invention relates to compounds of general formula (I) or of anyone of the embodiments as disclosed above—or the pharmaceutically acceptable salts thereof—for use in the treatment and/or prevention of cancer, infections, inflammations and autoimmune diseases.

In another aspect the invention relates to compounds of general formula (I) or of anyone of the embodiments as disclosed above—or the pharmaceutically acceptable salts thereof—for use in the treatment and/or prevention of cancer, preferably of carcinomas of the breast, in particular triple negative breast cancer (TNBC), prostate, brain or ovary, non-small-cell bronchial carcinomas (NSCLC), melanomas, acute myeloid leukaemia (AML) and chronic lymphatic leukaemias (CLL).

In another aspect the invention relates to compounds of general formula (I) or of anyone of the embodiments as disclosed above—or the pharmaceutically acceptable salts thereof—for use in the treatment and/or prevention of carcinomas of the breast, in particular triple negative breast cancer (TNBC), prostate, brain or ovary, non-small-cell bronchial carcinomas (NSCLC), melanomas, acute myeloid leukaemia (AML) and chronic lymphatic leukaemias (CLL).

In another aspect the invention relates to a method for the treatment and/or prevention of cancer comprising administering a therapeutically effective amount of a compound of general formula (I) or of anyone of the embodiments as disclosed above—or one of the pharmaceutically acceptable salts thereof—to a human being.

In another aspect the invention relates to a method for the treatment and/or prevention of carcinoma of the breast, in particular triple negative breast cancer (TNBC), prostate, brain or ovary, non-small-cell bronchial carcinomas (NSCLC), melanomas acute myeloid leukaemia (AML) and chronic lymphatic leukemias (CLL) comprising administering a therapeutically effective amount of a compound of general formula (I) or of anyone of the embodiments as disclosed above—or one of the pharmaceutically acceptable salts thereof—to a human being.

In another aspect the invention relates to a pharmaceutical preparation containing as active substance one or more compounds of general formula (I) or of anyone of the embodiments as disclosed above—or the pharmaceutically acceptable salts thereof—optionally in combination with conventional excipients and/or carriers.

In another aspect the invention relates to a pharmaceutical preparation comprising a compound of general formula (I) or of anyone of the embodiments as disclosed above—or one of the pharmaceutically acceptable salts thereof—and at least one other cytostatic or cytotoxic active substance, different from formula (I).

DEFINITIONS

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named sub-group is the radical attachment point, for example the substitutent —$C_{1-5}$alkyl-$C_{3-10}$cycloalkyl, means a $C_{3-10}$cycloalkyl group which is bound to a $C_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocyclylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$-alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —$CH_2$—$CH(CH_2CH_3)$)—, —($CH(CH_2CH_3)$—$CH_2$)—, —($CH(CH_2CH_2CH_3)$)—, —($CHCH(CH_3)_2$)— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkyleneamino or $H_2N$—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexa-dienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or $H_2N$—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or $H_2N$—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc.

The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

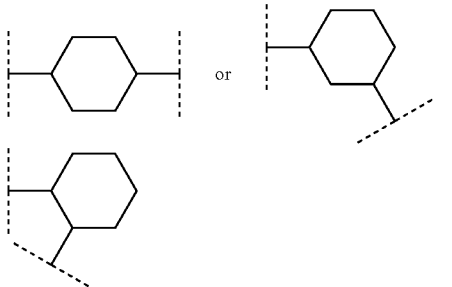

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

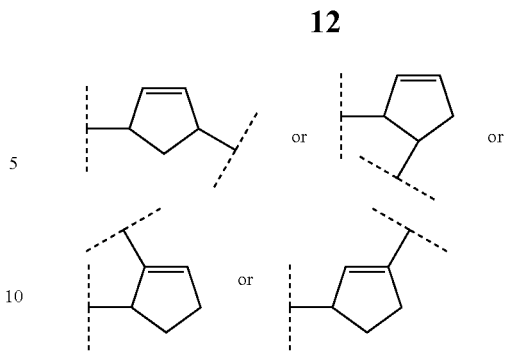

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g. phenyl and

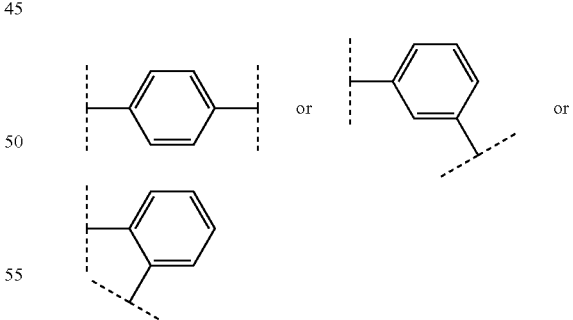

(o, m, p-phenylene), naphthyl and

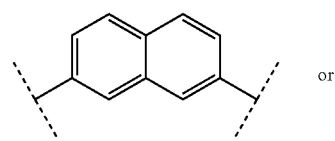

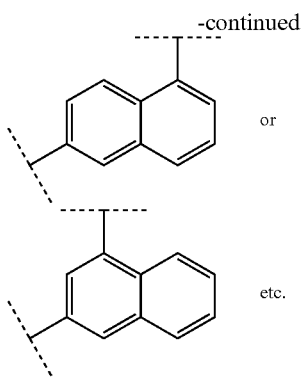

or etc.

The above definition for arylene also applies when arylene is part of another group as in HO-aryleneamino or $H_2N$-aryleneoxy for example.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —$SO_2$—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero) atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Aromatic heterocyclyl are those heterocyclyl comprising at least two ring, wherein at least one of which rings is aromatic.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]-nonyl, 1,4-dioxa-spiro[4.5]decyl, 1-oxa-3,8-diaza-spiro[4.5]decyl, 2,6-diaza-spiro[3.3]-heptyl, 2,7-diaza-spiro[4.4]nonyl, 2,6-diaza-spiro[3.4]octyl, 3,9-diaza-spiro[5.5]undecyl, 2.8-diaza-spiro[4.5]decyl etc.

Further examples are the structures illustrated below, which may be attached via each hydrogen-carrying atom (exchanged for hydrogen):

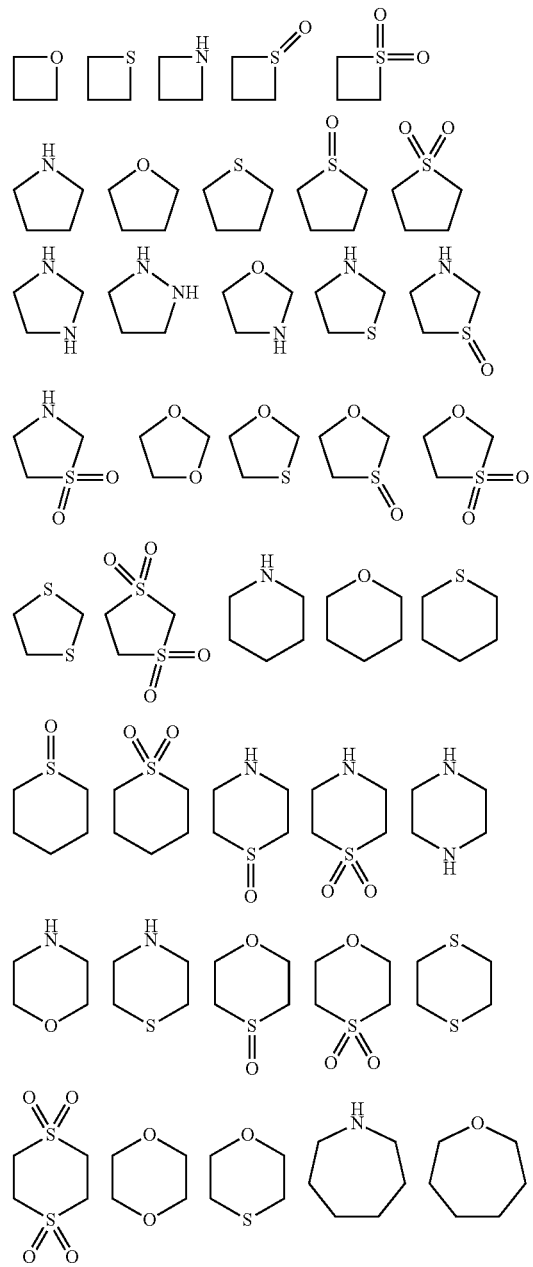

-continued
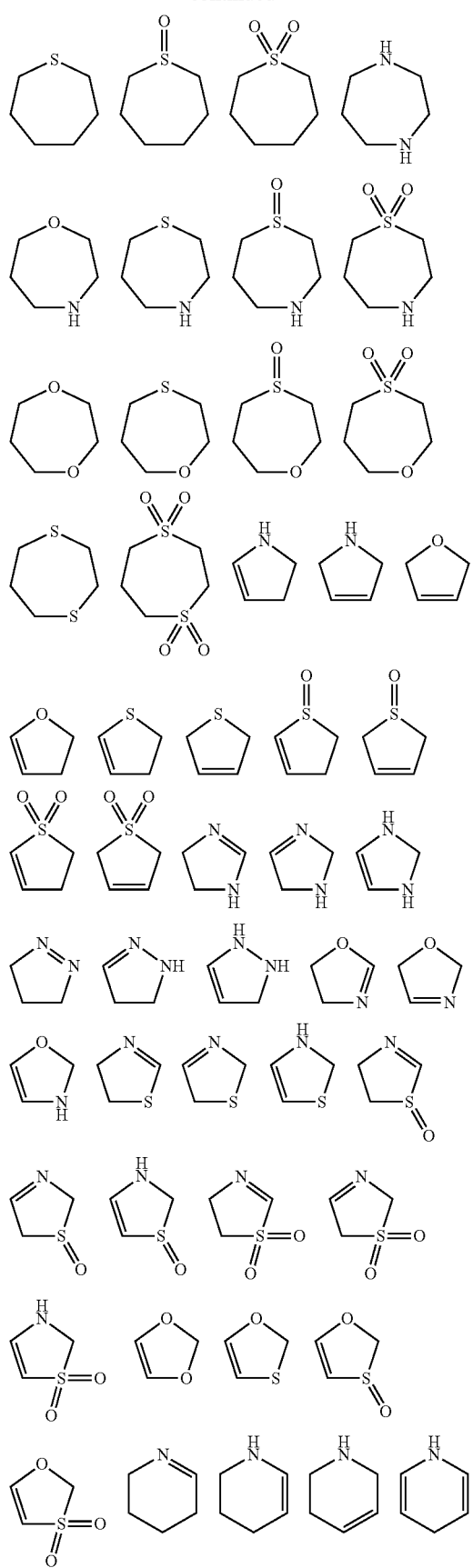
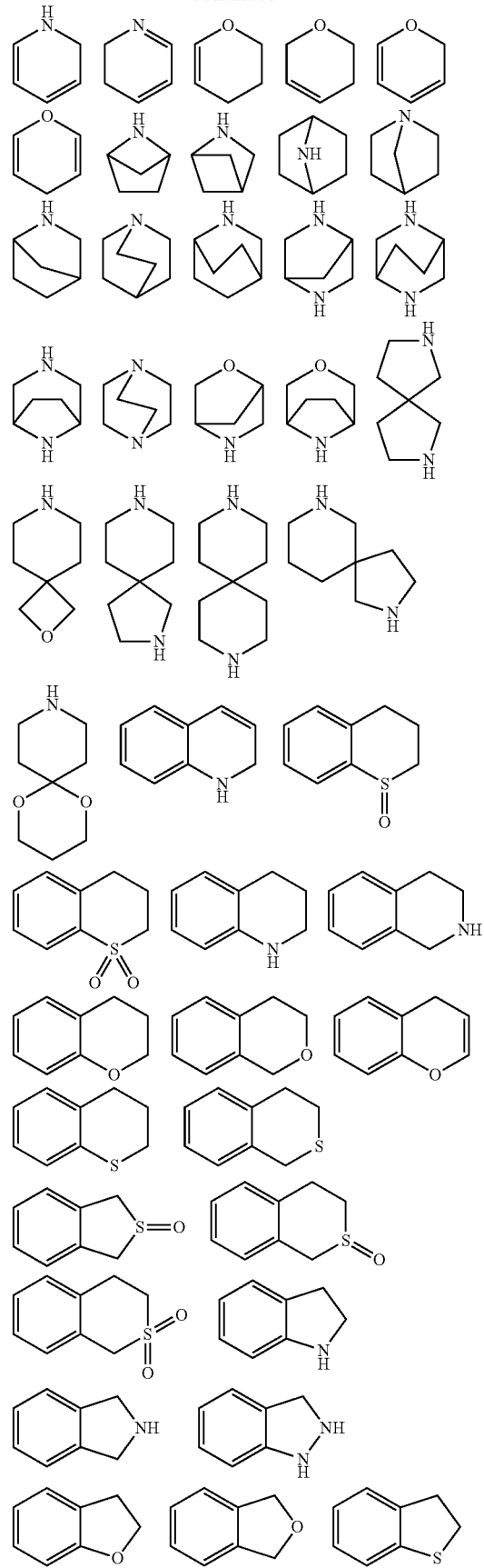

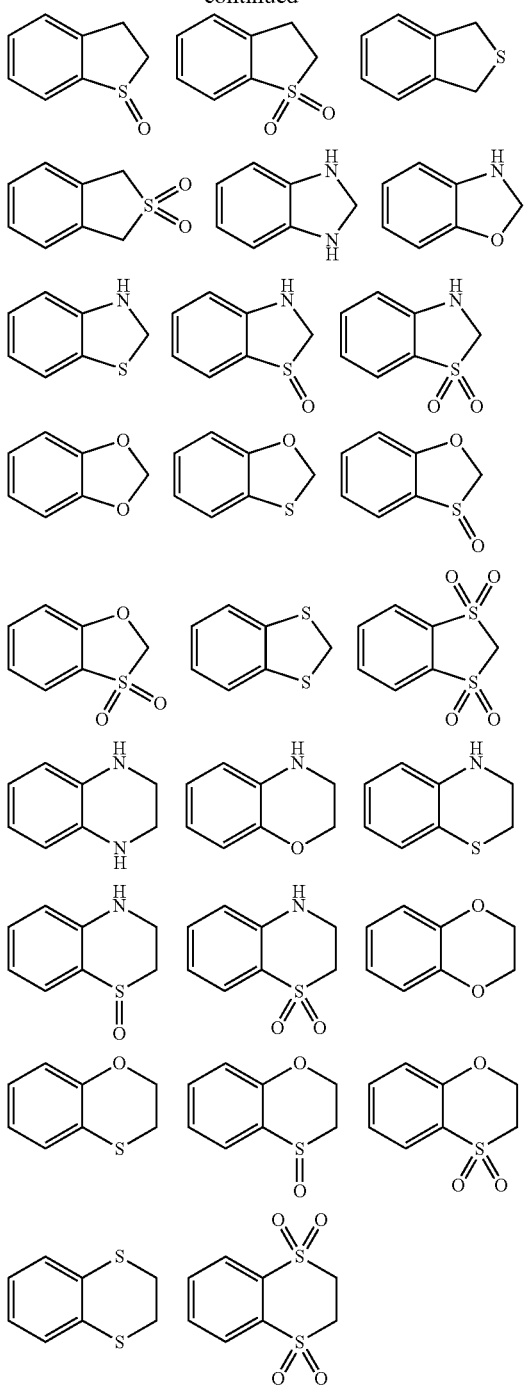

The above definition of heterocyclyl also applies if heterocyclyl is part of another group as in heterocyclylamino or heterocyclyloxy for example.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and 2,3-dihydro-1H-pyrrolyl and The above definition of heterocyclylene also applies if heterocyclylene is part of another group as in HO-heterocyclyleneamino or H$_2$N-heterocyclyleneoxy for example. Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

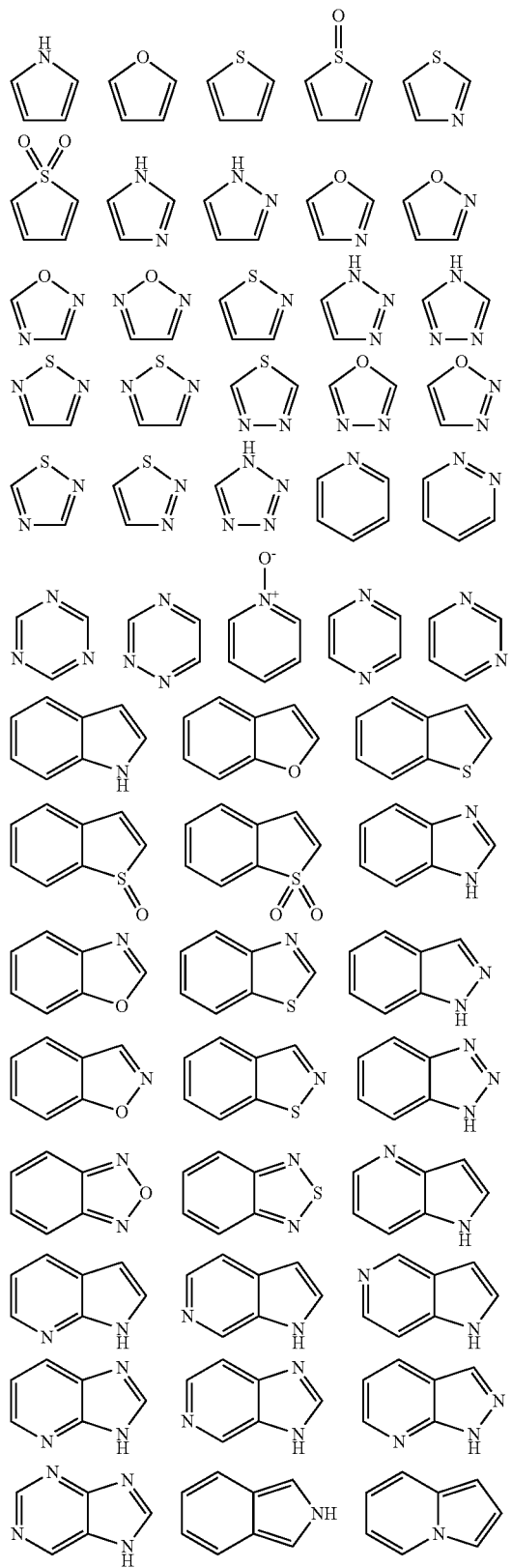

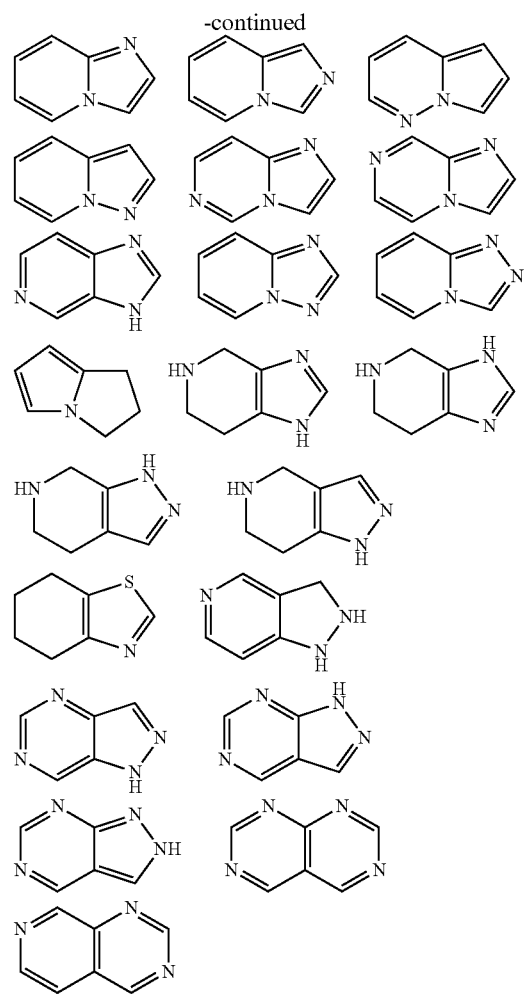

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

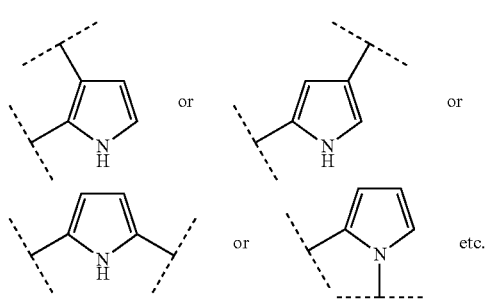

The above definition of heteroarylene also applies when heteroarylene is part of another group as in HO-heteroaryleneamino or H$_2$N-heteroaryleneoxy, for example.

The bivalent groups mentioned above (alkylene, alkenylene, alkynylene etc.) may also be part of composite groups (e.g. $H_2N-C_{1-4}$alkylene- or $HO-C_{1-4}$alkylene-). In this case one of the valencies is saturated by the attached group (here: $-NH_2$, $-OH$), so that a composite group of this kind written in this way is only a monovalent substituent over all.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsanilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound, which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

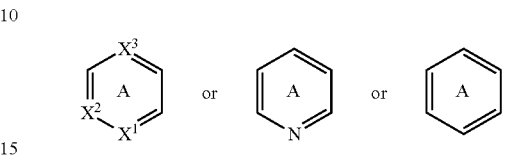

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

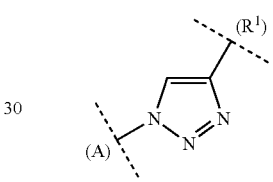

or $(R^2)-C(O)NH-$ or $(R^2)-NHC(O)-$;

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| | |
|---|---|
| ACN | acetonitrile |
| Bu | butyl |
| conc. | concentrated |
| d | day(s) |
| DCM | dichloromethane |
| DIPEA | diisopropylethyl amine |
| DMA | N,N-dimethylacetamide |
| DMAP | N,N-dimethylpyridin-4-amine |
| DMF | N,N-dimethylformamide |
| DMSO | dimethylsulphoxide |
| Et | ethyl |
| EtOAc | ethyl acetate |
| h | hour(s) |
| HATU | N-[(dimethylamino)-(1H-1,2,3-triazolo[4,5-b]pyridin-1-yl)-methylene]-N-methylmethan-aminium hexafluorophosphate N-oxide |
| HPLC | high performance liquid chromatography |
| iPr | isopropyl |

-continued

| | |
|---|---|
| M | molar |
| m.p. | melting point |
| Me | methyl |
| min | minute(s) |
| mL | millilitre |
| MS | mass spectrometry |
| N | normal |
| NMP | N-methylpyrrolindinone |
| NMR | nuclear resonance spectroscopy |
| NP | normal phase |
| ppm | part per million |
| prep | preparative |
| $R_f$ | retention factor |
| RP | reversed phase |
| RT | room temperature |
| tert | tertiary |
| TFA | trifluoroacetic acid |
| THF | tetrahydrofuran |
| TLC | thin layer chromatography |
| tR | retention time |

Other features and advantages of the present invention will become apparent from the following more detailed examples which exemplarily illustrate the principles of the invention without restricting its scope.

General

Unless stated otherwise, all the reactions are carried out in commercially obtainable apparatuses using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with IUPAC guidelines using ChemAxon's MarvinView 6.0.0 software. If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

A Biotage Isolera Four apparatus is used for automated preparative NP chromatography together with Interchim Puri Flash columns (50 μm, 12-300 g) or glass columns filled with silica gel made by Millipore (Granula Silica Si-60A 35-70 μm).

Preparative RP HPLC is carried out with columns made by Waters (Sunfire C18, 10 μm, 30×100 mm Part. No. 186003971 or X-Bridge C18, 10 μm, 30×100 mm Part. No. 186003930). The compounds are eluted using either different gradients of $H_2O$/acetonitrile or $H_2O$/MeOH, where 0.2% HCOOH is added to the water, or with different gradients utilizing a basic aqueous buffer solution (1 L water contains 5 mL of an ammonium hydrogencarbonate solution (158 g per 1 L $H_2O$) and 2 mL ammonia (7 mol/l solution in MeOH)) instead of the water-HCOOH-mixture.

The analytical HPLC (reaction monitoring) of intermediate compounds is carried out with columns made by Agilent and Waters. The analytical equipment is also provided with a mass detector in each case.

HPLC Mass Spectroscopy/UV Spectrometry

The retention times/MS-ESI$^+$ for characterising the example compounds according to the invention are determined using an HPLC-MS apparatus (high performance liquid chromatography with mass detector) made by Agilent or Shimadzu. Compounds that elute at the injection peak are given the retention time tR=0.

Analytical HPLC Methods

| Method_1 | |
|---|---|
| HPLC: | Agilent 1100 Series |
| MS: | Agilent LC/MSD SL |
| Column: | Waters, Xbridge C18, 2.5 μm, 2.1 × 20 mm |
| Solvent: | A: 20 mM $NH_4HCO_3$/ $NH_3$ |
| | B: ACN HPLC grade |
| Detection: | MS: Positive and negative |
| Mass range: | 120-800 m/z |
| Injection: | 5 μL |
| Flow: | 1.00 mL/min |
| Column temp.: | 60° C. |
| Gradient: | 0.00-1.50 min 10% → 95% B |
| | 1.50-2.00 min 95% B |
| | 2.00-2.10 min 95% → 10% B |

| Method_2 | |
|---|---|
| HPLC: | Agilent 1100/1200 Series |
| MS: | Agilent LC/MSD SL |
| Column: | Waters Sunfire, C18, 5.0 μm, 2.1 × 50 mm |
| Eluant: | A: $H_2O$ + 0.2% HCOOH; B: ACN |
| Detection: | MS: Positive and negative mode ESI |
| Mass range: | 105-1200 m/z |
| Flow: | 1.20 ml/min |
| Column temp.: | 35° C. |
| Gradient: | 0.00-0.01 min: 5% B |
| | 0.01-1.50 min: 5% → 95% B |
| | 1.50-2.00 min: 100% B |

| Method_3 | |
|---|---|
| HPLC: | Agilent 1100/1200 Series |
| MS: | Agilent LC/MSD SL |
| Column: | Waters X-Bridge BEH C18, 2.5 μm, 2.1 × 30 mm |
| Eluant: | A: 5 mM $NH_4HCO_3$/19 mM $NH_3$ in $H_2O$; |
| | B: ACN (HPLC grade) |
| Detection: | MS: Positive and negative mode ESI |
| Mass range: | 100-800 m/z |
| Flow: | 1.4 ml/min |
| Column temp.: | 45° C. |
| Gradient: | 0.00-0.01 min: 5% B |
| | 0.01-1.00 min: 5% → 100% B |
| | 1.00-1.37 min: 100% B |
| | 1.37-1.40 min: 100% → 5% B |

| Method_4 | |
|---|---|
| HPLC: | Agilent 1100 Series |
| MS: | Agilent LC/MSD SL |
| Column: | WatersXBridge C18, 5.0 μm, 2.1 × 50 mm |
| Eluant: | A: 5 mM $NH_4HCO_3$/19 mM $NH_3$ in $H_2O$; |
| | B: ACN (HPLC grade) |
| Detection: | MS: Positive and negative mode ESI |
| Mass range: | 105-1200 m/z |
| Flow: | 1.20 ml/min |
| Column temp.: | 35° C. |
| Gradient: | 0.00-0.01 min: 5% B |
| | 0.01-1.25 min: 5% → 95% B |
| | 1.25-2.00 min: 95% B |
| | 2.00-2.01 min: 95% → 5% B |

| Method_5 | |
|---|---|
| HPLC: | Shimadzu LC-20AB CTC PAL HTS |
| MS: | LCMS2010EV |
| UV: | SPD-M20A PDA |
| ELSD: | PL 2100 |
| Column: | Waters Atlantis dC18, 2.1 × 30 mm, 3 μm |
| Eluant: | A: $H_2O$ + 0.1% HCOOH; B: ACN (HPLC grade) + 0.1% HCOOH |
| Detection: | MS: Positive mode |
| Mass range: | 100-1000 m/z |
| Flow: | 1.0 ml/min |
| Column temp.: | 40° C. |
| Gradient: | 0.00-0.01 min: 5% B |
| | 0.01-1.50 min: 5% → 100% B |
| | 1.50-1.60 min: 100% B |
| | 1.60-1.61 min: 100% → 5% B |

-continued

| Method_6 | |
|---|---|
| HPLC: | Shimadzu LC-20AB CTC PAL HTS |
| MS: | LCMS2010EV |
| UV: | SPD-M20A PDA |
| ELSD: | PL 2100 |
| Column: | Waters Atlantis dC18, 2.1 × 100 mm, 3 μm |
| Eluant: | A: $H_2O$ + 0.1% HCOOH; B: ACN (HPLC grade) + 0.1% HCOOH |
| Detection: | MS: Positive mode |
| Mass range: | 100-1000 m/z |
| Flow: | 0.6 ml/min |
| Column temp.: | 40° C. |
| Gradient: | 0.00-0.01 min: 5% B |
| | 0.01-5.00 min: 5% → 100% B |
| | 5.00-5.40 min: 100% B |
| | 5.42 min: 100% → 5% B |

| Method_7 | |
|---|---|
| HPLC: | Shimadzu LC-20AB CTC PAL HTS |
| MS: | LCMS2010EV |
| UV: | SPD-M20A PDA |
| ELSD: | none |
| Column: | Waters Atlantis dC18, 2.1×100mm, 3 μm |
| Eluant: | A: $H_2O$ + 0.1% HCOOH; B: ACN (HPLC grade) + 0.1% HCOOH |
| Detection: | MS: Positive mode |
| Mass range: | 100-1000 m/z |
| Flow: | 0.6 ml/min |
| Column temp.: | 40° C. |
| Gradient: | 0.00-0.01 min: 5% B |
| | 0.01-5.00 min: 5% → 100% B |
| | 5.00-5.40 min: 100% B |
| | 5.42 min: 100% → 5% B |

Preparation of the Compounds According to the Invention

The compounds according to the invention are prepared by methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in literature are prepared according to the published methods.

Unless otherwise specified, the substituents $R^1$ through $R^5$ of the following reaction schemes are as defined in the specification and claims.

The compounds of formula (I) may be prepared according to the following schemes.

One method for the preparation of compounds of formula (I) is depicted in Scheme 1. An amino-dihalogeno-pyridine A is converted into the alkyne intermediate B e.g. via Sonogashira coupling utilizing a suitably protected alkyne. Intermediates C can be obtained through amidation reaction. The introduction of R4 moieties, e.g. by means of a coupling reaction with suitable boronic acids or via Miyaura borylation and subsequent Suzuki coupling results in intermediates D. Intermediates E which are obtained by deprotection of intermediates D can be further transformed into intermediates H e.g. via Sonogashira coupling. Finally, compounds of the formula (I) are obtained after deprotection of the amino function. The products are isolated by conventional means and preferably purified by chromatography.

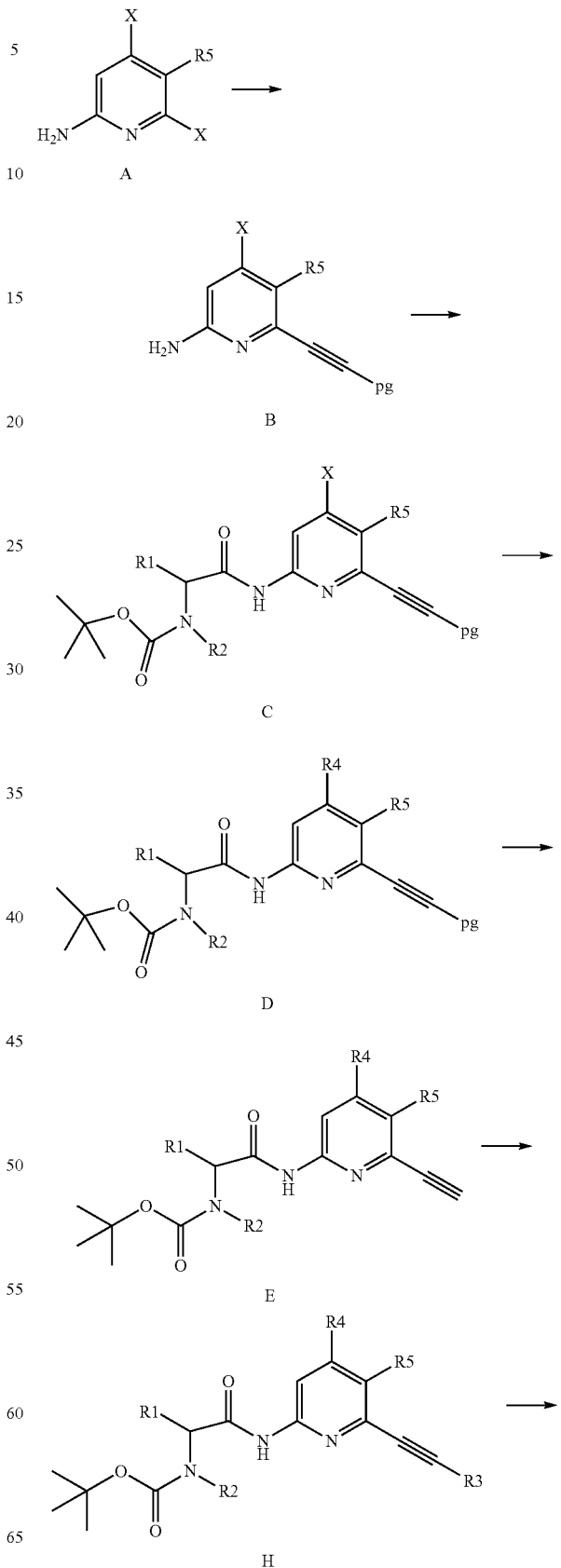

Scheme 1

-continued

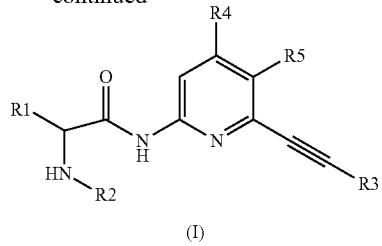

(I)

Additionally, the introduction of certain R5 moieties (e.g. R5=Cl, Br) can be also performed at a later stage starting from intermediates C in which R5=H:

Scheme 1b

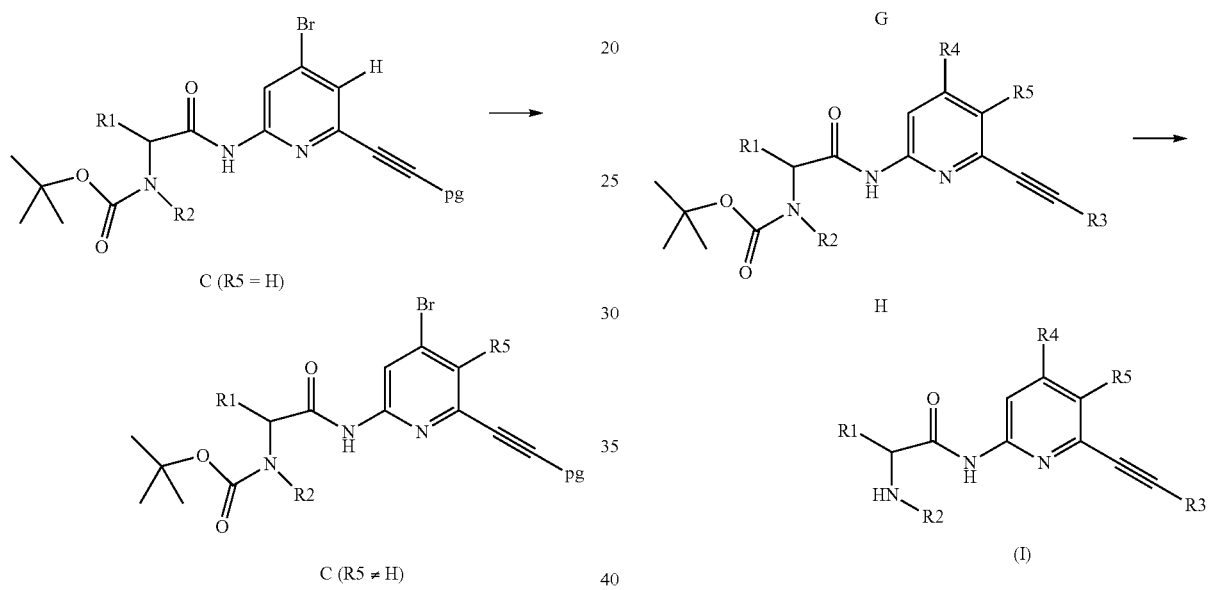

Another method for the preparation of compounds of formula (I) is depicted in Scheme 2. An amino-dihalogeno-pyridine A is converted into intermediates F, e.g. via Sonogashira coupling utilizing ethinyl-R3 building blocks. Intermediates F can be transformed into intermediates G by introduction of R4 moieties, e.g. through coupling reaction with suitable boronic acids or via Miyaura borylation and subsequent Suzuki coupling. Intermediates H are obtained through amidation reaction. Optionally, the amidation reaction can be also performed prior to the introduction of R4. H can be transformed into compounds of the formula (I) via deprotection of the amino function. The products are isolated by conventional means and preferably purified by chromatography.

Scheme 2

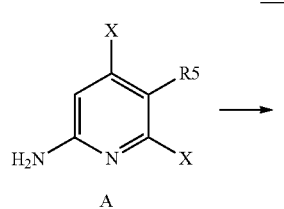

A

-continued

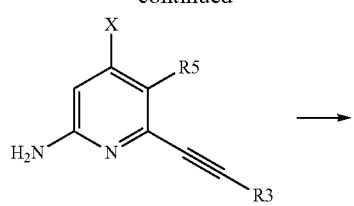

F

G

H (I)

Additionally, R5 moieties can be introduced at a later stage starting from intermediates G in which R5=H, e.g. via halogenation reaction and subsequent Suzuki coupling:

Scheme 2b

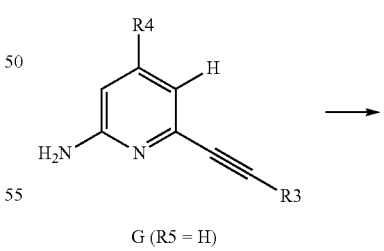

G (R5 = H)

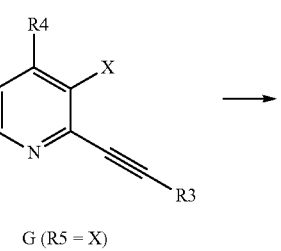

G (R5 = X)

-continued

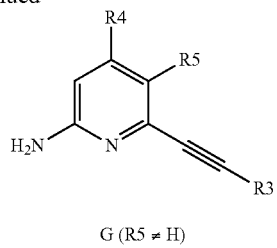

G (R5 ≠ H)

Preparation of Compounds a

A1) 2-Amino-4,6-dibromo-5-methoxy-pyridine

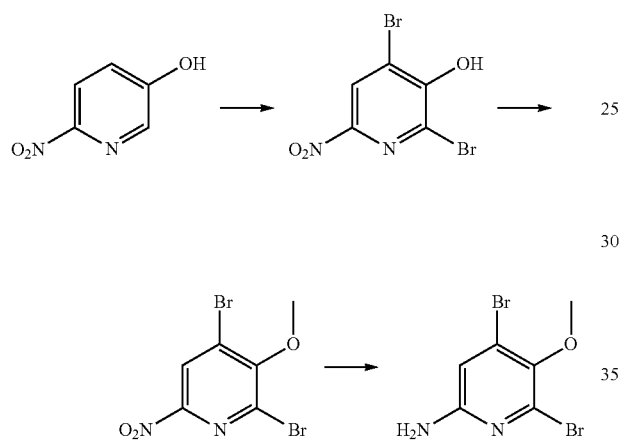

DIPEA (1.2 ml, 7.1 mmol) is added to a mixture of 6-nitro-pyridin-3-ol (900 mg, 6.4 mmol) in DCM (10 ml). Benzyltrimethylammonium tribromide (5.3 g, 13.5 mmol) in DCM (20 ml) is added at RT and the mixture is stirred for 15 min. The mixture is concentrated in vacuo and the intermediate 2,4-dibromo-6-nitro-pyridin-3-ol purified by RP HPLC. Yield: 1.14 g (60%). HPLC-MS: tR=0.21 min (METHOD_1)

A mixture of 2,4-dibromo-6-nitro-pyridin-3-ol (1.4 g, 4.7 mmol), DIPEA (8 ml; 47 mmol) and dimethylsulfate (4.5 ml, 47 mmol) is stirred at 50° C. for 1 h. The mixture is diluted with DCM and extracted with a saturated aqueous solution of sodium hydrogencarbonate. The combined organic layers are dried over MgSO$_4$ and concentrated in vacuo. The intermediate 2,4-dibromo-3-methoxy-6-nitro-pyridine is purified by RP HPLC. Yield: 1.29 g (88%). HPLC-MS: tR=1.10 min (METHOD_1).

Under an atmosphere of nitrogen 2,4-dibromo-3-methoxy-6-nitro-pyridine (0.8 g, 2.6 mmol) in THF (150 ml) is treated with Raney Nickel (50 mg). At RT the atmosphere is replaced by hydrogen (5 bar) and stirring is continued for 2 h. The mixture is filtered and concentrated in vacuo. The crude 2-amino-4,6-dibromo-5-methoxy-pyridine A1 (0.72 g) is used in the next step without further purification.

Preparation of Compounds B

B1) 4-bromo-6-{2-[tris(propan-2-yl)silyl]ethynyl}pyridin-2-amine

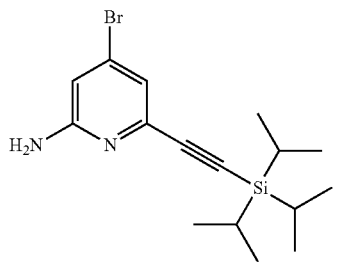 [SMILES: CC(C)[Si](C#Cc1cc(Br)cc(N)n1)(C(C)C)C(C)C]

Under argon atmosphere dichlorobis(triphenylphosphine)palladium(II) (1.6 g, 2.2 mmol) is added to a mixture of 2-amino-4,6-dibromopyridine (5.44 g, 21.6 mmol), ethynyl-tri(propan-2-yl)silane (5.1 g, 28.1 mmol), copper(I) iodide (0.44 g, 2.3 mmol) and triethylamine (9 ml, 64 mmol) in ACN (32 ml) with THF (16 ml). After stirring at 50° C. for 17 h the mixture is diluted with water and extracted with EtOAc. The combined organic layers are dried over MgSO$_4$ and concentrated in vacuo. The product is purified by NP chromatography. Yield: 4.7 g (62%). HPLC-MS: M+H=353/355; tR=1.80 min (METHOD_1).

Preparation of Compounds C

C1) (1-{4-Bromo-6-[(triisopropylsilanyl)-ethynyl]-pyridin-2-ylcarbamoyl}-ethyl)-methyl-carbamic acid tert-butyl ester

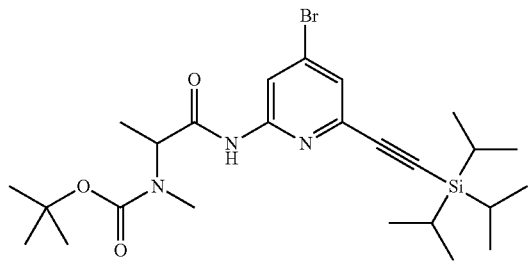 [SMILES: CC(C(=O)Nc1cc(Br)cc(C#C[Si](C(C)C)(C(C)C)C(C)C)n1)N(C)C(=O)OC(C)(C)C]

2,4,6-tripropyl-1,3,5,2,4,6-trioxatriphosphorinane-2,4,6-trioxide (70 ml of a 50 wt.-% solution in EtOAc, 118 mmol) is added to a mixture of 4-bromo-6-{2-[tris(propan-2-yl)silyl]ethynyl}pyridin-2-amine B1 (10.4 g, 29.5 mmol), 2-[methyl-[(2-methylpropan-2-yl)oxycarbonyl]amino]propanoic acid (12 g, 59 mmol) and pyridine (20 ml) at −20° C. The mixture is stirred for 3 h at that temperature. 200 ml of a saturated aqueous sodium hydrogencarbonate solution is added and the mixture extracted with EtOAc. The combined organic layers are dried over MgSO$_4$ and concentrated in vacuo. The product is purified by NP chromatography. Yield: 11.1 g (70%). HPLC-MS: M+H=538/540; tR=.2.05 min (METHOD_1).

C2) tert-butyl-N-{1-[(4-bromo-5-chloro-6-{2-[tris(propan-2-yl)silyl]ethynyl}-pyridin-2-yl)carbamoyl]ethyl}-N-methylcarbamate

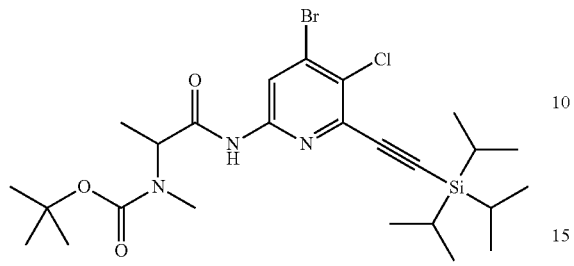

A mixture of (1-{4-Bromo-6-[(triisopropylsilanyl)-ethynyl]-pyridin-2-ylcarbamoyl}-ethyl)-methyl-carbamic acid tert-butyl ester C1 (50 mg, 930 μmol), N-chlorosuccinimide (12 mg, 0.90 mmol) and ACN (1 ml) is stirred at 50° C. for 17 h. The mixture is concentrated in vacuo and the product purified by RP HPLC. Yield: 11 mg (21%). HPLC-MS: M+H=574/572; tR=2.04 min (METHOD_1).

Preparation of Compounds D

D1) tert-butyl-N-{1-[(4-{1,3-dimethyl-1H-pyrazolo[4,3-d]pyrimidin-7-yl}-6-{2-[tris(propan-2-yl)silyl]ethynyl}pyridin-2-yl)carbamoyl]ethyl}-N-methylcarbamate

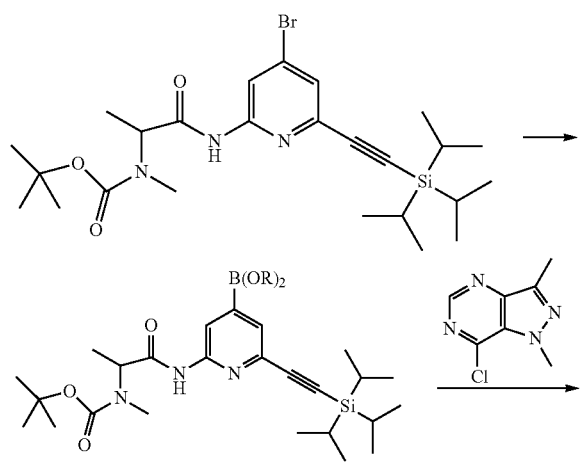

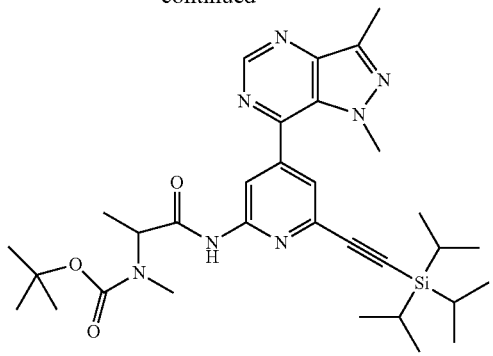

1,1'-Bis(diphenylphosphino)ferrocene]dichloropalladium (II) (0.38 g, 0.52 mmol) is added to a mixture of (1-{4-Bromo-6-[(triisopropylsilanyl)-ethynyl]-pyridin-2-ylcarbamoyl}-ethyl)-methyl-carbamic acid tert-butyl ester C1 (0.70 g, 1.3 mmol), bis(neopentyl glycolato)diboron (0.59 g, 2.6 mmol), KOAc (0.38 g, 3.9 mmol) and DMSO (7.5 ml) under argon atmosphere and the mixture is stirred at 50° C. for 2 h to obtain the boronic acid derivative. Directly to this mixture is added at RT under argon atmosphere 7-chloro-1,3-dimethyl-1H-pyrazolo[4,3-d]pyrimidine (0.48 g, 2.6 mmol), sodium carbonate (0.41 g, 3.9 mmol), water (1.5 ml) and 1,1'-Bis(diphenylphosphino)ferrocene]dichloropalladium(II) (0.19 g, 0.26 mmol). The mixture is stirred at 100° C. for 4 h. The mixture is diluted with water and extracted with EtOAc. The combined organic layers are dried over MgSO4 and concentrated in vacuo. The product is purified by RP HPLC. Yield: 0.52 g (66%). HPLC-MS: M+H=606; tR=1.91 min (METHOD_1).

The following compounds are prepared analogously utilizing 5-bromo-6-methoxy-2-methylquinoline, 6-chloro-7-methyl-7H-purine, 4-chloro-5,6-dimethylfuro[2,3-d]-pyrimidine, 5-bromo-2,3-dimethylimidazo[1,2-a]pyridine, 7-bromo-1-methyl-1H-indazole, 3-iodo-5-methylimidazo[1,2-a]pyridine Ka, 7-bromo-1,2,4,6-tetramethyl-1H,2H,3H-pyrazolo[4,3-c]pyridin-3-one Kb, 7-chloro-1,3,5-trimethyl-1H-pyrazolo[4,3-d]pyrimidine or N'-(5-acetyl-6-chloro-2-methylpyrimidin-4-yl)-N-methyl(tert-butoxy)carbohydrazide Kc, respectively.

| # | Molecular Structure | Chemical Name |
|---|---|---|
| D2 | 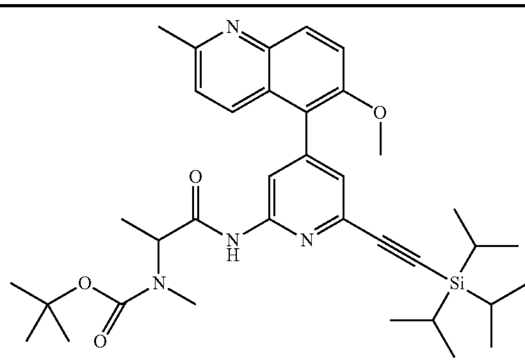 | tert-butyl-N-(1-{[4-(6-methoxy-2-methoxyquinolin-5-yl)-6-{2-[tris(propan-2-yl)silyl]ethynyl}pyridin-2-yl]carbamoyl}ethyl)-N-methylcarbamate |

| # | Molecular Structure | Chemical Name |
|---|---|---|
| D3 | 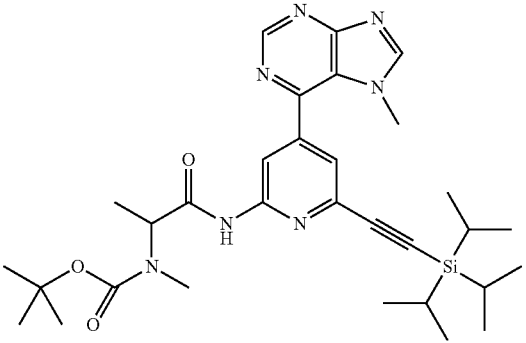 [SMILES: CC(C(=O)Nc1cc(-c2ncnc3ncn(C)c23)cc(C#C[Si](C(C)C)(C(C)C)C(C)C)n1)N(C)C(=O)OC(C)(C)C] | tert-butyl-N-methyl-N-(1-{[4-(7-methyl-7H-purin-6-yl)-6-{2-[tris(propan-2-yl)silyl]ethynyl}pyridin-2-yl]carbamoyl}ethyl)carbamate |
| D4 | 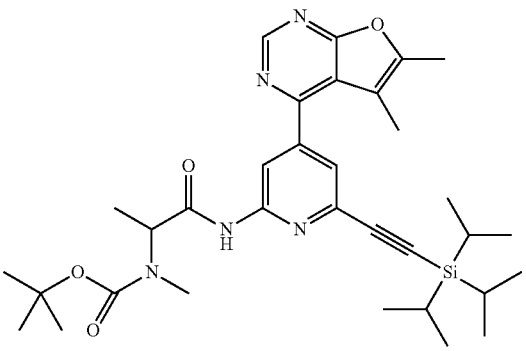 [SMILES: Cc1oc2ncnc(-c3cc(C#C[Si](C(C)C)(C(C)C)C(C)C)nc(NC(=O)C(C)N(C)C(=O)OC(C)(C)C)c3)c2c1C] | tert-butyl-N-{1-[(4-{5,6-dimethylfuro[2,3-d]pyrimidin-4-yl}-6-{2-[tris(propan-2-yl)silyl]ethynyl}pyridin-2-yl)carbamoyl]ethyl}-N-methylcarbamate |
| D5 | 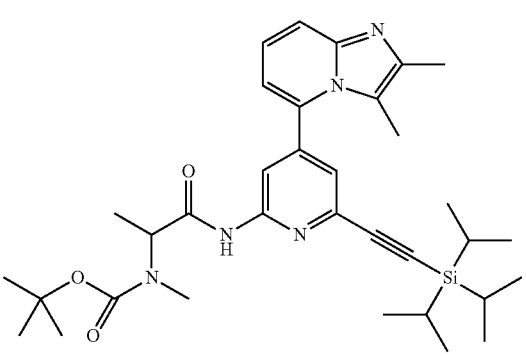 [SMILES: Cc1nc2cccc(-c3cc(C#C[Si](C(C)C)(C(C)C)C(C)C)nc(NC(=O)C(C)N(C)C(=O)OC(C)(C)C)c3)n2c1C] | tert-butyl-N-{1-[(4-{2,3-dimethylimidazo[1,2-a]pyridin-5-yl}-6-{2-[tris(propan-2-yl)silyl]ethynyl}pyridin-2-yl)carbamoyl]ethyl}-N-methylcarbamate |
| D6 | 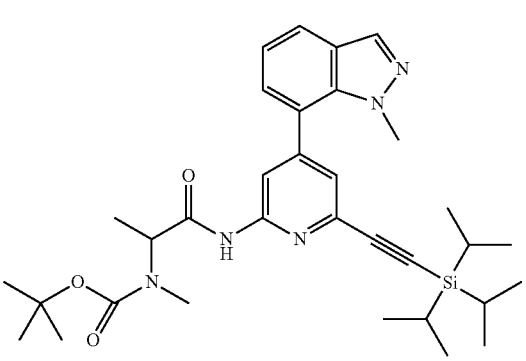 [SMILES: CC(C(=O)Nc1cc(-c2cccc3cnn(C)c23)cc(C#C[Si](C(C)C)(C(C)C)C(C)C)n1)N(C)C(=O)OC(C)(C)C] | tert-butyl-N-methyl-N-(1-{[4-(1-methyl-1H-indazol-7-yl)-6-{2-[tris(propan-2-yl)silyl]ethynyl}pyridin-2-yl]carbamoyl}ethyl)carbamate |

| # | Molecular Structure | Chemical Name |
|---|---|---|
| D7 | 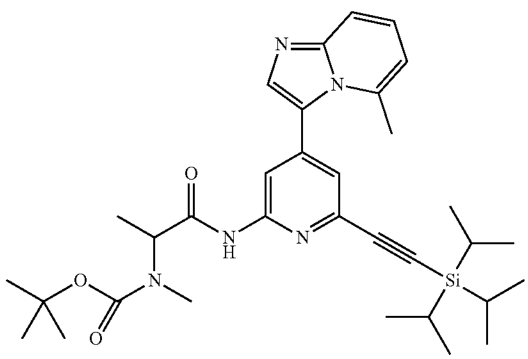 [SMILES: Cc1cccc2ncc(-c3cc(C#C[Si](C(C)C)(C(C)C)C(C)C)nc(NC(=O)C(C)N(C)C(=O)OC(C)(C)C)c3)n12] | tert-butyl-N-methyl-N-{1-[(4-{5-methylimidazo[1,2-a]pyridin-3-yl}-6-{2-[tris(propan-2-yl)silyl]ethynyl}pyridin-2-yl)carbamoyl]ethyl}carbamate |
| D8 | 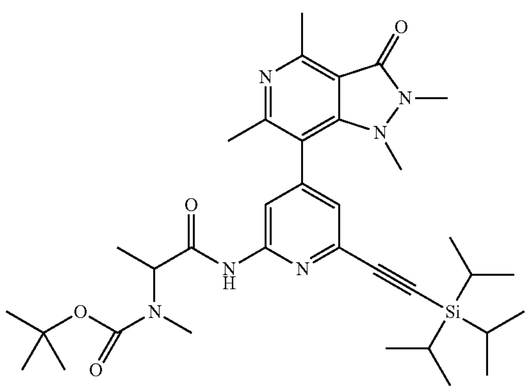 [SMILES: Cc1nc(C)c2c(=O)n(C)n(C)c2c1-c1cc(C#C[Si](C(C)C)(C(C)C)C(C)C)nc(NC(=O)C(C)N(C)C(=O)OC(C)(C)C)c1] | tert-butyl-N-methyl-N-{1-[(4-{1,2,4,6-tetramethyl-3-oxo-1H,2H,3H-pyrazolo[4,3-c]pyridin-7-yl}-6-{2-[tris(propan-2-yl)silyl]ethynyl}pyridin-2-yl)carbamoyl]ethyl}carbamate |
| D9 | 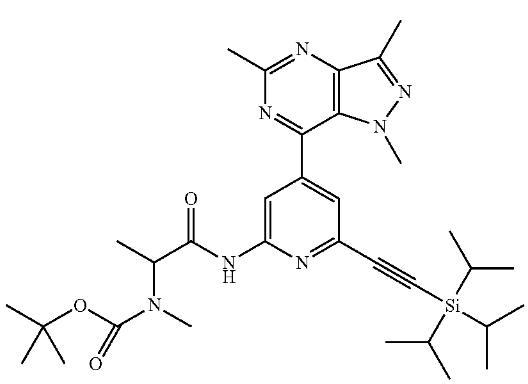 [SMILES: Cc1nc(-c2cc(C#C[Si](C(C)C)(C(C)C)C(C)C)nc(NC(=O)C(C)N(C)C(=O)OC(C)(C)C)c2)c2c(n1)c(C)nn2C] | tert-butyl-N-methyl-N-{1-[(4-{trimethyl-1H-pyrazolo[4,3-d]pyrimidin-7-yl}-6-{2-[tris(propan-2-yl)silyl]ethynyl}pyridin-2-yl)carbamoyl]ethyl}carbamate |

| # | Molecular Structure | Chemical Name |
|---|---|---|
| D10 | 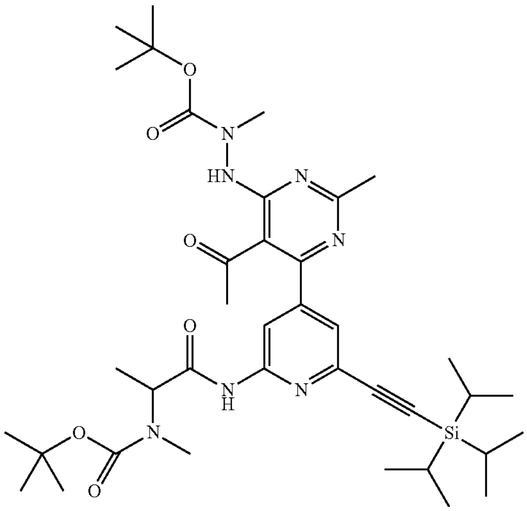 [SMILES: CC(=O)c1c(NN(C)C(=O)OC(C)(C)C)nc(C)nc1-c1cc(C#C[Si](C(C)C)(C(C)C)C(C)C)nc(NC(=O)C(C)N(C)C(=O)OC(C)(C)C)c1] | tert-butyl-N-[1-({4-{5-acetyl-6-({[(tert-butoxy)carbonyl](methyl)amino}amino)-2-methylpyrimidin-4-yl]-6-{2-[tris(propan-2-yl)silyl]ethynyl}pyridin-2-yl}carbamoyl)ethyl]-N-methylcarbamate |

D11) tert-butyl-N-[(1S)-1-{[5-chloro-4-(1-methyl-1H-indazol-7-yl)-6-{2-[tris(propan-2-yl)silyl]ethynyl}pyridin-2-yl]carbamoyl}ethyl]-N-methylcarbamate

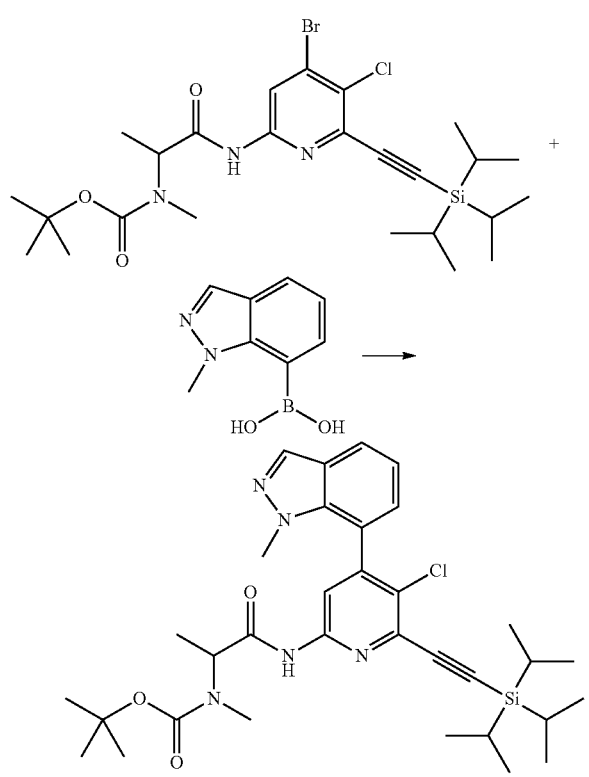

1,1'-bis(diphenylphosphino)ferrocene]dichloropalladium (II) (20 mg, 0.03 mmol) is added to a mixture of tert-butyl-N-{1-[(4-bromo-5-chloro-6-{2-[tris(propan-2-yl)silyl]ethynyl}-pyridin-2-yl)carbamoyl]ethyl}-N-methylcarbamate C2 (82 mg, 0.14 mmol), (1-methyl-1H-indazol-7-yl)boronic acid (24 mg, 0.14 mmol), Na$_2$CO$_3$ (44 mg, 0.42 mmol), dioxane (0.8 ml) and water (0.2 ml) under argon atmosphere and stirred at 100° C. for 4 h. The mixture is diluted with water (10 ml) and extracted with EtOAc. The combined organic layers are dried over MgSO$_4$ and concentrated in vacuo. The product is purified by RP HPLC. Yield: 25 mg (28%). HPLC-MS: M+H=624; tR=1.94 min (METHOD_1).

Preparation of Compounds E

E1) tert-butyl-N-{1-[(4-{1,3-dimethyl-1H-pyrazolo[4,3-d]pyrimidin-7-yl}-6-ethynylpyridin-2-yl)carbamoyl]ethyl}-N-methylcarbamate

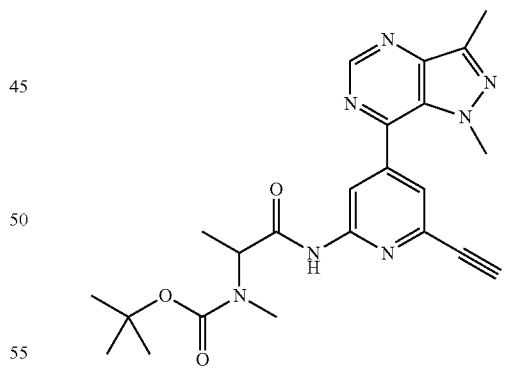

A mixture of tert-butyl-N-{1-[(4-{1,3-dimethyl-1H-pyrazolo[4,3-d]pyrimidin-7-yl}-6-{2-[tris(propan-2-yl)silyl]ethynyl}pyridin-2-yl)carbamoyl]ethyl}-N-methylcarbamate D1 (0.52 g, 0.86 mmol), THF (10 ml) and tetrabutylammonium fluoride (1 mol/l solution in THF, 0.95 ml, 0.95 mmol) is stirred at RT for 1 h. The mixture is diluted with DCM and extracted with a saturated aqueous solution of sodium hydrogencarbonate and brine. The combined organic layers are dried over MgSO$_4$ and concentrated in vacuo. The crude product is used in the next step without further purification.

The following compounds E2-E11 are prepared analogously from D2-D11, respectively:

| # | Molecular Structure | Chemical Name |
|---|---|---|
| E2 | 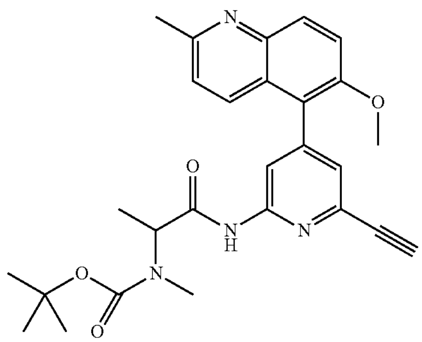 [SMILES: C#Cc1cc(-c2c(OC)ccc3nc(C)ccc23)cc(NC(=O)C(C)N(C)C(=O)OC(C)(C)C)n1] | tert-butyl-N-(1-{[6-ethynyl-4-(6-methoxy-2-methylquinolin-5-yl)pyridin-2-yl]carbamoyl}ethyl)-N-methylcarbamate |
| E3 | 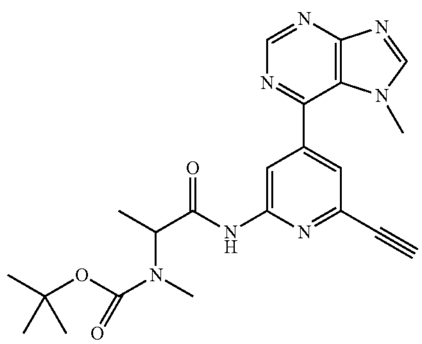 [SMILES: C#Cc1cc(-c2ncnc3ncn(C)c23)cc(NC(=O)C(C)N(C)C(=O)OC(C)(C)C)n1] | tert-butyl-N-(1-{[6-ethynyl-4-(7-methyl-7H-purin-6-yl)pyridin-2-yl]carbamoyl}ethyl)-N-methylcarbamate |
| E4 | 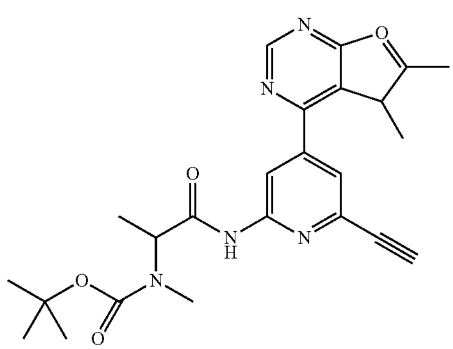 | tert-butyl-N-{1-[(4-{5,6-dimethylfuro[2,3-d]pyrimidin-4-yl}-6-ethynylpyridin-2-yl)carbamoyl]ethyl}-N-methylcarbamate |
| E5 | 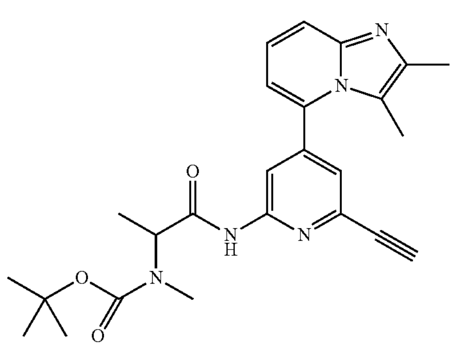 [SMILES: C#Cc1cc(-c2cccc3nc(C)c(C)n23)cc(NC(=O)C(C)N(C)C(=O)OC(C)(C)C)n1] | tert-butyl-N-{1-[(4-{2,3-dimethylimidazo[1,2-a]pyridin-5-yl}-6-ethynylpyridin-2-yl)carbamoyl]ethyl}-N-methylcarbamate |

| # | Molecular Structure | Chemical Name |
|---|---|---|
| E6 | 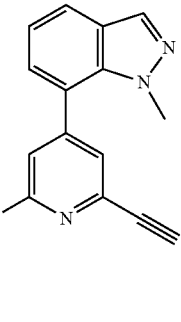 | tert-butyl-N-(1-{[6-ethynyl-4-(1-methyl-1H-indazol-7-yl)pyridin-2-yl]carbamoyl}ethyl)-N-methylcarbamate |
| E7 | 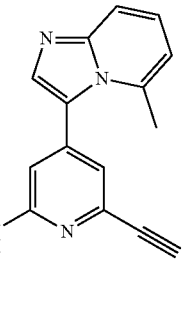 | tert-butyl-N-{1-[(6-ethynyl-4-{5-methylimidazo[1,2-a]pyridin-3-yl}pyridin-2-yl)carbamoyl]ethyl}-N-methylcarbamate |
| E8 | 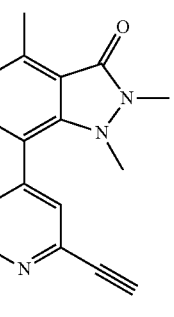 | tert-butyl-N-{1-[(6-ethynyl-4-{1,2,4,6-tetramethyl-3-oxo-1H,2H,3H-pyrazolo[4,3-c]pyridin-7-yl}pyridin-2-yl)carbamoyl]ethyl}-N-methylcarbamate |
| E9 | 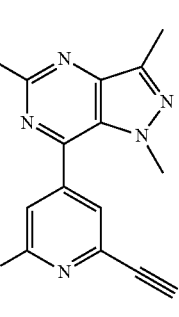 | tert-butyl-N-{1-[(6-ethynyl-4-{trimethyl-1H-pyrazolo[4,3-d]pyrimidin-7-yl}pyridin-2-yl)carbamoyl]ethyl}-N-methylcarbamate |

| # | Molecular Structure | Chemical Name |
|---|---|---|
| E10 | 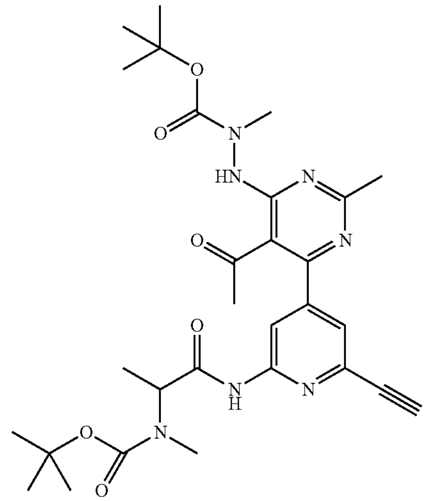 [SMILES: C#Cc1cc(-c2nc(C)nc(NN(C)C(=O)OC(C)(C)C)c2C(C)=O)cc(NC(=O)C(C)N(C)C(=O)OC(C)(C)C)n1] | tert-butyl-N-[1-({4-[5-acetyl-6-({[(tert-butoxy)carbonyl](methyl)amino}amino)-2-methylpyrimidin-4-yl]-6-ethynylpyridin-2-yl}carbamoyl)ethyl]-N-methylcarbamate |
| E11 | 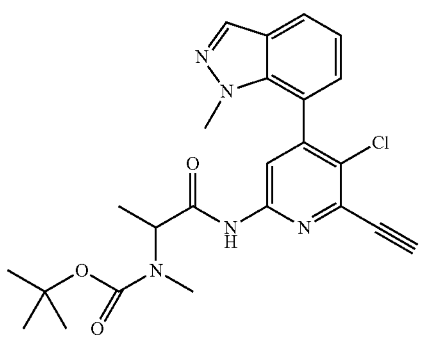 [SMILES: C#Cc1nc(NC(=O)C(C)N(C)C(=O)OC(C)(C)C)cc(-c2cccc3cnn(C)c23)c1Cl] | tert-butyl-N-(1-{[5-chloro-6-ethynyl-4-(1-methyl-1H-indazol-7-yl)pyridin-2-yl]carbamoyl}ethyl)-N-methylcarbamate |

Preparation of Compounds F

F1) 4-chloro-6-(2-phenylethynyl)pyridin-2-amine

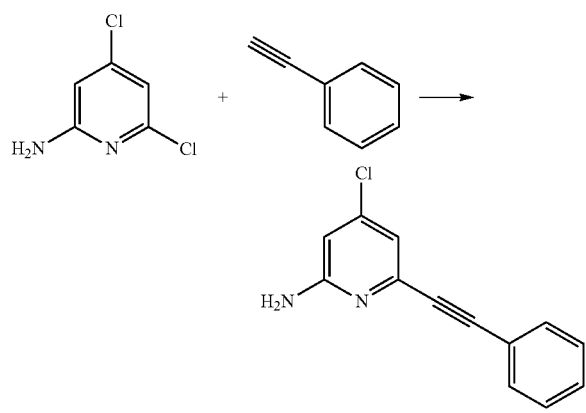

Dichlorobis(triphenylphosphine)palladium(II) (2.5 g, 3.06 mmol) is added to a mixture of 2-amino-4,6-dichloropyridine (5 g, 30.7 mmol), ethynylbenzene (7.05 g, 69 mmol), copper (I) iodide (0.58 g, 3.07 mmol), triethylamine (10.8 ml, 78 mmol), THF (25 ml) and ACN (50 ml) under argon atmosphere and is stirred at 90° C. for 17 h. The mixture is diluted with water (100 ml) and extracted with EtOAc. The combined organic layers are dried over $MgSO_4$ and concentrated in vacuo. The product is purified by NP chromatography. Yield: 3.52 g (50%). HPLC-MS: M+H=229; tR=1.85 min (METHOD_1).

F2) 4-bromo-5-methoxy-6-(2-phenylethynyl)pyridin-2-amine

Dichlorobis(triphenylphosphine)palladium(II) (17 mg, 25 µmol) is added to a mixture of 2-amino-4,6-dibromo-5-methoxy-pyridine A1 (70 mg, 0.25 mmol), ethynylbenzene (55 µl, 0.50 mmol), copper(I) iodide (5 mg, 25 µmol) triethylamine (140 µl, 1 mmol) and THF (1 ml) under argon atmosphere and is stirred at 50° C. for 1 h. The mixture is concentrated in vacuo and the product purified by RP HPLC. Yield: 35 mg (47%). HPLC-MS: tR=1.21 min (METHOD_1).

Preparation of Compounds G

G1) 6-(2-phenylethynyl)-4-(pyridin-4-yl)pyridin-2-amine

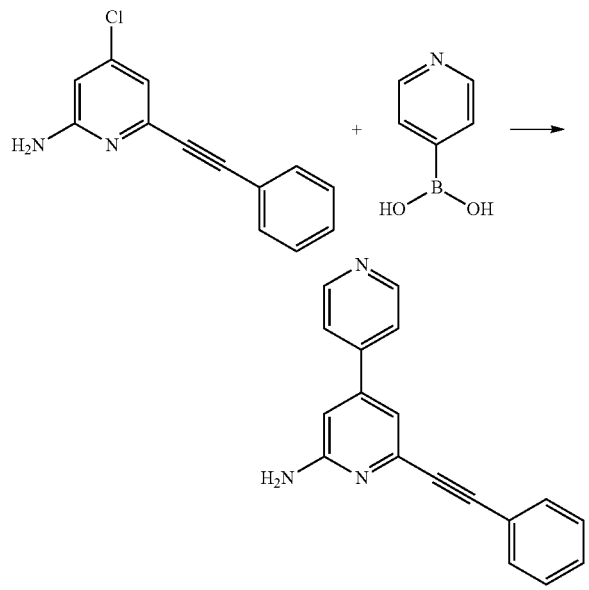

Dichlorobis(triphenylphosphine)palladium(II) (0.15 g, 0.22 mmol) is added to a mixture of 4-chloro-6-(2-phenylethynyl)pyridin-2-amine F1 (0.4 g, 1.7 mmol), pyridine-4-boronic acid (0.32 g, 2.6 mmol), $Cs_2CO_3$ (1.7 g, 5.2 mmol), 1,2-dimethoxyethane (8 ml), MeOH (2 ml) and water (2 ml) under argon atmosphere at RT and is stirred at 120° C. for 17 h. The mixture is diluted with water (100 ml) and extracted with EtOAc. The combined organic layers are dried over $MgSO_4$ and concentrated in vacuo. The product is purified by RP HPLC. Yield: 0.24 g (51%). HPLC-MS: M+H=272; tR=1.29 min (METHOD_1).

The following compounds are prepared analogously utilizing (5-fluoropyridin-3-yl)boronic acid, [6-(trifluoromethyl)pyridin-3-yl]boronic acid, (6-methoxypyridin-3-yl)boronic acid, (2-fluorophenyl)boronic acid, phenylboronic acid or (pyridin-3-yl)boronic acid, respectively:

| # | Molecular Structure | Chemical Name |
|---|---|---|
| G2 | | 4-(5-fluoropyridin-3-yl)-6-(2-phenylethynyl)pyridin-2-amine |
| G3 | 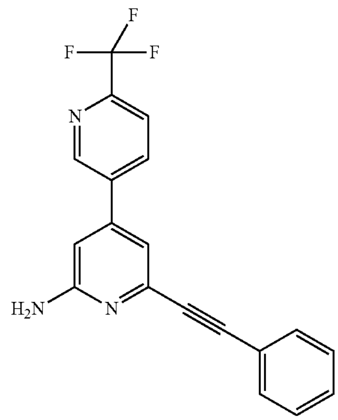 [SMILES: Nc1cc(-c2ccc(C(F)(F)F)nc2)cc(C#Cc2ccccc2)n1] | 6-(2-phenylethynyl)-4-[6-(trifluoromethyl)pyridin-3-yl]pyridin-2-amine |
| G4 | 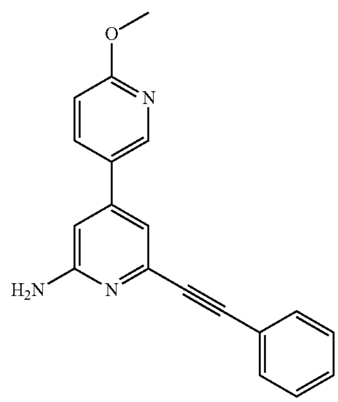 [SMILES: COc1ccc(-c2cc(N)nc(C#Cc3ccccc3)c2)cn1] | 4-(6-methoxypyridin-3-yl)-6-(2-phenylethynyl)pyridin-2-amine |
| G5 | 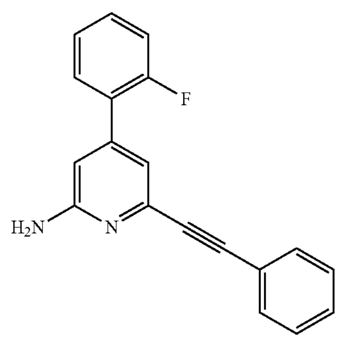 [SMILES: Nc1cc(-c2ccccc2F)cc(C#Cc2ccccc2)n1] | 4-(2-fluorophenyl)-6-(2-phenylethynyl)pyridin-2-amine |
| G6 | 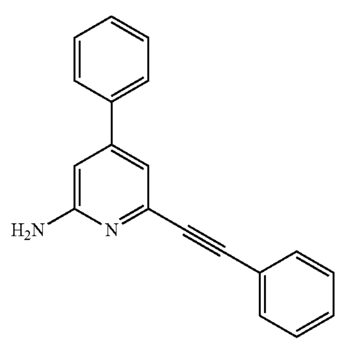 [SMILES: Nc1cc(-c2ccccc2)cc(C#Cc2ccccc2)n1] | 4-phenyl-6-(2-phenylethynyl)pyridin-2-amine |

-continued

| # | Molecular Structure | Chemical Name |
|---|---|---|
| G7 | 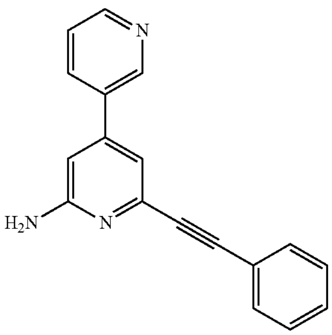 [SMILES: Nc1cc(-c2cccnc2)cc(C#Cc2ccccc2)n1] | 6-(2-phenylethynyl)-4-(pyridin-3-yl)pyridin-2-amine |

G8) 5-bromo-6-(2-phenylethynyl)-4-(pyridin-4-yl)pyridin-2-amine

A mixture of 6-(2-phenylethynyl)-4-(pyridin-4-yl)pyridin-2-amine G1 (93 mg, 0.34 mmol), N-bromosuccinimide (61 mg, 0.34 mmol) and ACN (11 ml) is stirred in the dark at RT for 20 h. The mixture is concentrated in vacuo and the product purified by NP chromatography. Yield: 90 mg (75%). HPLC-MS: M+H=350/352; tR=1.18 min (METHOD_5).

G9) 6-(2-phenylethynyl)-4-(pyridin-4-yl)-5-(pyrimidin-5-yl)pyridin-2-amine

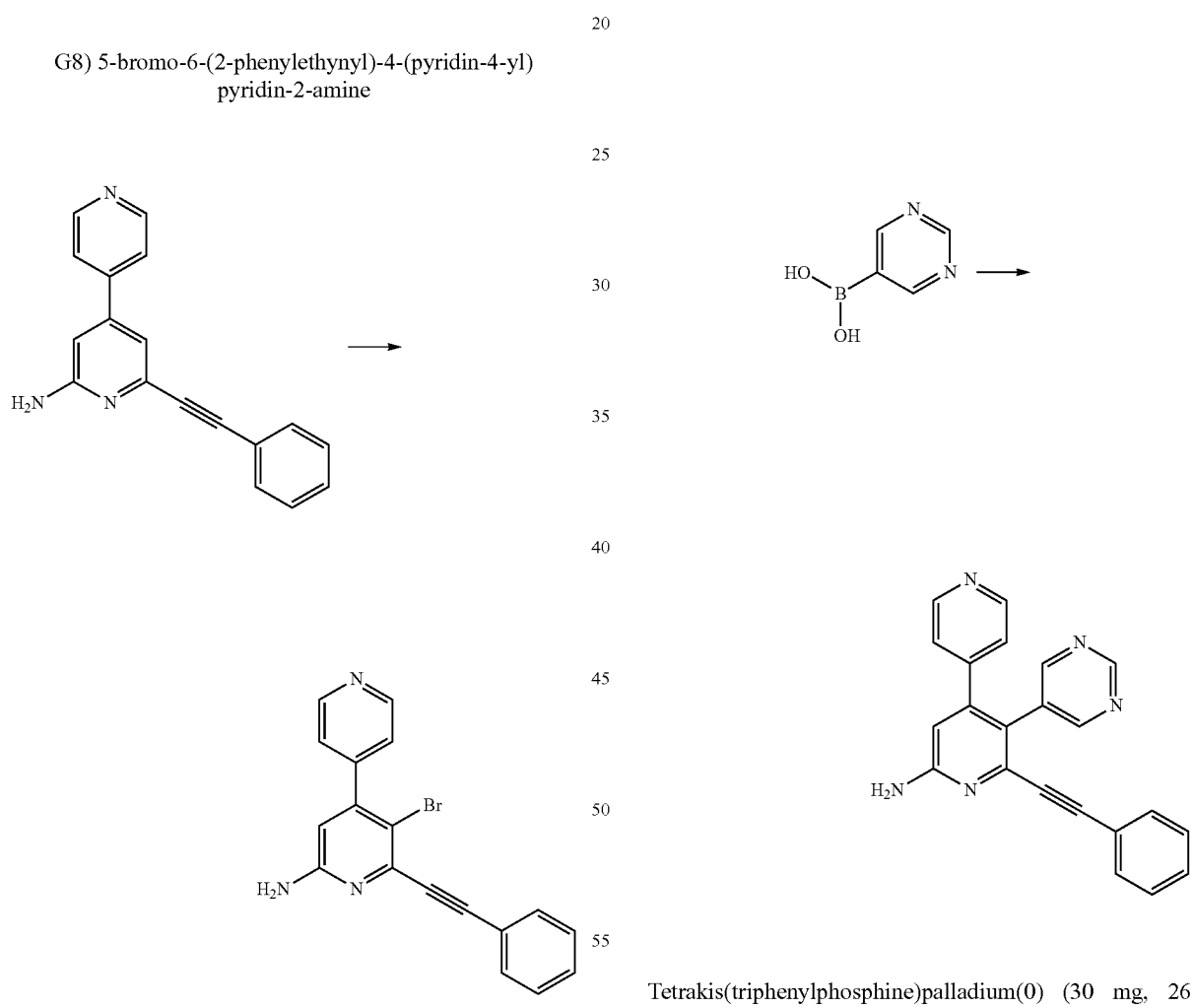

Tetrakis(triphenylphosphine)palladium(0) (30 mg, 26 µmol) is added to a mixture of 5-bromo-6-(2-phenylethynyl)-4-(pyridin-4-yl)pyridin-2-amine G8 (90 mg, 0.26 mmol), pyrimidine-5-boronic acid (48 mg, 0.39 mmol), sodium carbonate (aqueous solution, 2 mol/l, 0.39 ml, 0.78 mmol) and ACN (2.4 ml) under nitrogen atmosphere at RT and is stirred at 150° C. for 1 h. The mixture is concentrated in vacuo and the product purified by NP chromatography. Yield: 72 mg (80%). HPLC-MS: M+H=350; tR=1.11 min (METHOD_5).

The following compound is prepared analogously starting from G7:

| # | Molecular Structure | Chemical Name |
|---|---|---|
| G10 | 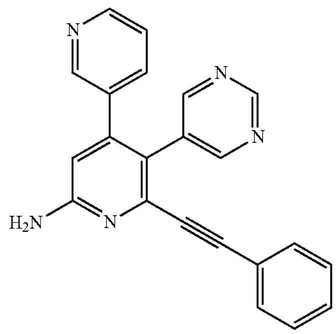 [SMILES: Nc1cc(-c2cccnc2)c(-c2cncnc2)c(C#Cc2ccccc2)n1] | 6-(2-phenylethynyl)-4-(pyridin-3-yl)-5-(pyrimidin-5-yl)pyridin-2-amine |

Preparation of Compounds H

H1) tert-butyl-N-{1-[(4-{1,3-dimethyl-1H-pyrazolo[4,3-d]pyrimidin-7-yl}-6-[2-(1-methyl-1H-indazol-5-yl)ethynyl]pyridin-2-yl)carbamoyl]ethyl}-N-methylcarbamate

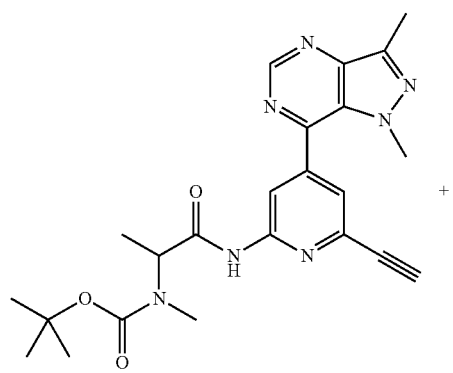

+

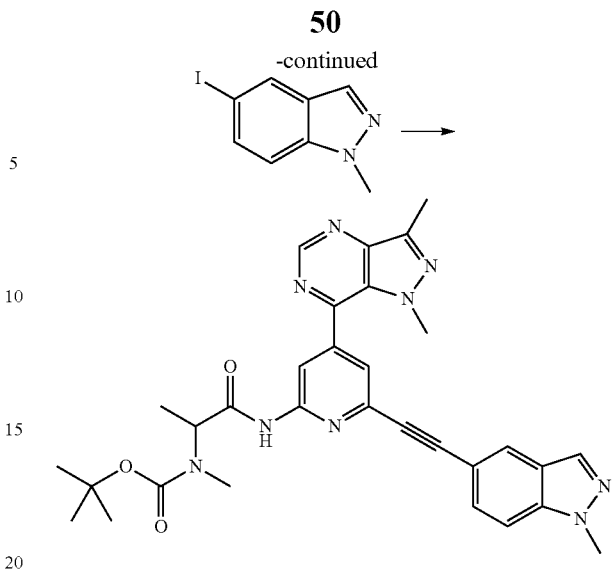

Dichlorobis(triphenylphosphine)palladium(II) (94 mg, 0.13 mmol) is added to a mixture of tert-butyl-N-{1-[(4-{1,3-dimethyl-1H-pyrazolo[4,3-d]pyrimidin-7-yl}-6-ethynylpyridin-2-yl)carbamoyl]ethyl}-N-methylcarbamate E1 (0.3 g, 0.47 mmol), 5-iodo-1-methyl-1H-indazole (0.17 g, 0.67 mmol), copper(I) iodide (13 mg, 68 µmol), DIPEA (340 µl, 2 mmol) and NMP (2 ml) under argon atmosphere at RT and is stirred at 50° C. for 17 h. The mixture is concentrated in vacuo and the product purified by RP HPLC. Yield: 107 mg (40%). HPLC-MS: M+H=580; tR=.2.11 min (METHOD_2).

The following compounds are prepared analogously from E1-E11 utilizing 6-iodo-1-methylisoquinoline La, 4-bromo-8-fluoro-2-methylquinoline, 7-bromo-3-methyl-imidazo[1,5-a]pyridine, iodobenzene, 6-iodo-1-methyl-1H-quinolin-2-one, 4-(4-methyl-imidazol-1-yl) iodobenzene, 5-iodo-1-methyl-2,3-dihydro-1H-indol-2-one, 5-iodo-1-methyl-1H-indazole, 5-bromo-2-(4-methyl-1H-imidazol-1-yl)pyrimidine, 2-iodothiophene, 6-bromo-2-methyl-quinoline, 4-bromo-2,6-dimethyl-pyridine, 1,3-difluoro-5-iodobenzene, 6-bromo-8-fluoro-quinoline or 5-bromo-1-methyl-1H-pyrazolo[3,4-b]pyridine:

| # | Molecular Structure | Chemical Name |
|---|---|---|
| H2 | 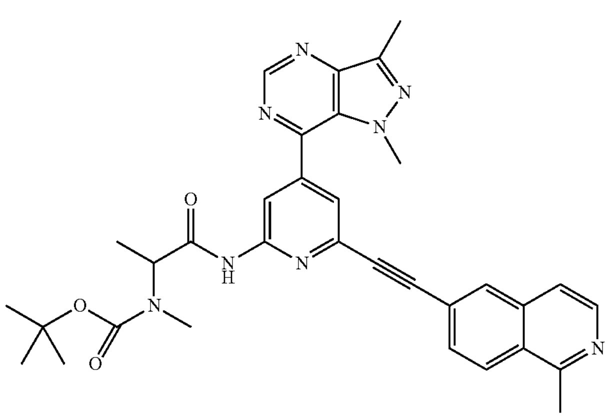 [SMILES: Cc1nccc2cc(C#Cc3cc(-c4ncnc5c(C)nn(C)c45)cc(NC(=O)C(C)N(C)C(=O)OC(C)(C)C)n3)ccc12] | tert-butyl-N-{1-[(4-{1,3-dimethyl-1H-pyrazolo[4,3-d]pyrimidin-7-yl}-6-[2-(1-methylisoquinolin-6-yl)ethynyl]pyridin-2-yl)carbamoyl]ethyl}-N-methylcarbamate |

-continued

| # | Molecular Structure | Chemical Name |
|---|---|---|
| H3 | 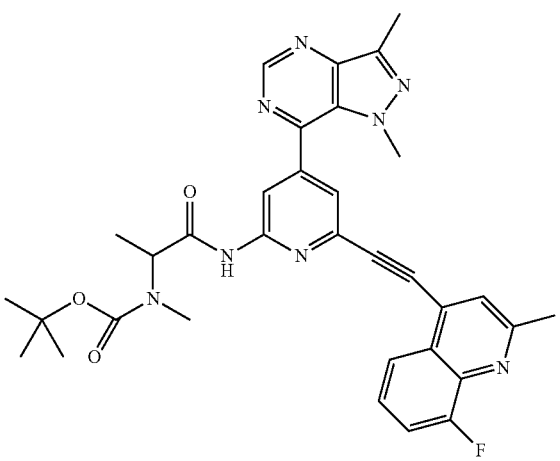 [SMILES: Cc1cc(C#Cc2cc(-c3ncnc4c(C)nn(C)c34)cc(NC(=O)C(C)N(C)C(=O)OC(C)(C)C)n2)c2cccc(F)c2n1] | tert-butyl-N-{1-[(4-{1,3-dimethyl-1H-pyrazolo[4,3-d]pyrimidin-7-yl}-6-[2-(8-fluoro-2-methylquinolin-4-yl)ethynyl]pyridin-2-yl)carbamoyl]ethyl}-N-methylcarbamate |
| H4 | 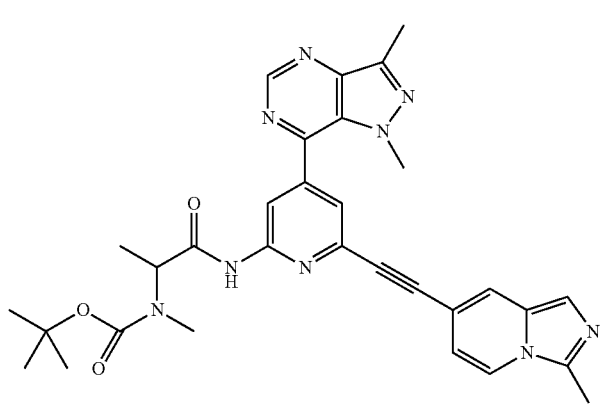 [SMILES: Cc1nn(C)c2c(-c3cc(C#Cc4ccn5c(C)ncc5c4)nc(NC(=O)C(C)N(C)C(=O)OC(C)(C)C)c3)ncnc12] | tert-butyl-N-{1-[(4-{1,3-dimethyl-1H-pyrazolo[4,3-d]pyrimidin-7-yl}-6-(2-{3-methylimidazo[1,5-a]pyridin-7-yl}ethynyl)pyridin-2-yl)carbamoyl]ethyl}-N-methylcarbamate |
| H5 | 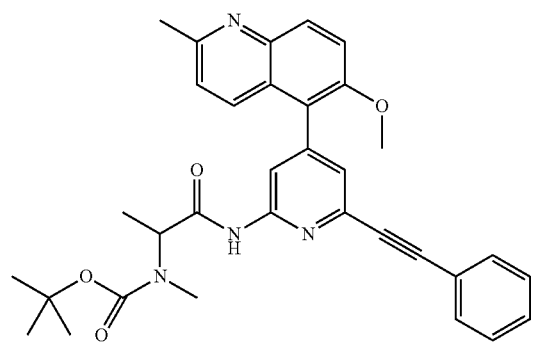 [SMILES: COc1ccc2nc(C)ccc2c1-c1cc(C#Cc2ccccc2)nc(NC(=O)C(C)N(C)C(=O)OC(C)(C)C)c1] | tert-butyl-N-(1-{[4-(6-methoxy-2-methylquinolin-5-yl)-6-(2-phenylethynyl)pyridin-2-yl]carbamoyl}ethyl)-N-methylcarbamate |
| H6 | 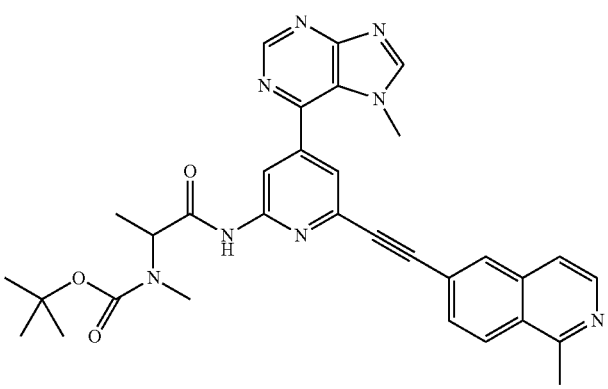 [SMILES: Cc1nccc2cc(C#Cc3cc(-c4ncnc5ncn(C)c45)cc(NC(=O)C(C)N(C)C(=O)OC(C)(C)C)n3)ccc12] | tert-butyl-N-methyl-N-(1-{[4-(7-methyl-7H-purin-6-yl)-6-[2-(1-methylisoquinolin-6-yl)ethynyl]pyridin-2-yl]carbamoyl}ethyl)carbamate |

| # | Molecular Structure | Chemical Name |
|---|---|---|
| H7 | 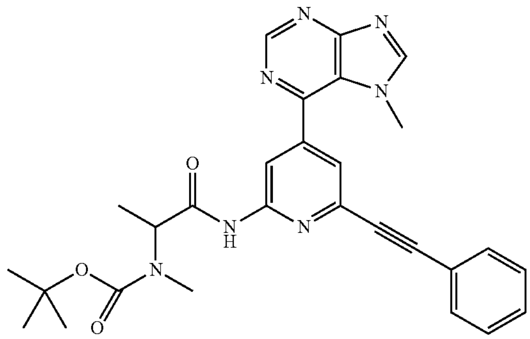 [SMILES: CC(C(=O)Nc1cc(-c2ncnc3ncn(C)c23)cc(C#Cc2ccccc2)n1)N(C)C(=O)OC(C)(C)C] | tert-butyl-N-methyl-N-(1-{[4-(7-methyl-7H-purin-6-yl)-6-(2-phenylethynyl)pyridin-2-yl]carbamoyl}ethyl)carbamate |
| H8 | 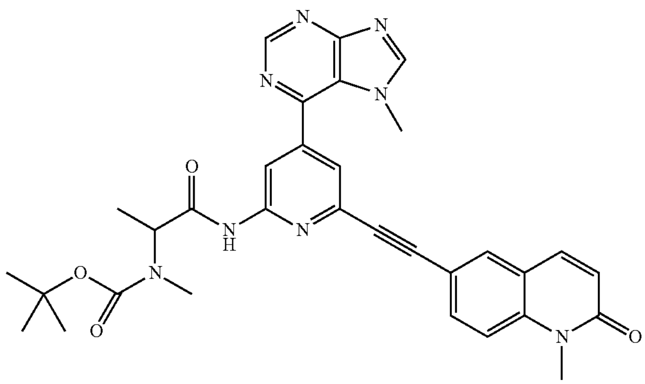 [SMILES: CC(C(=O)Nc1cc(-c2ncnc3ncn(C)c23)cc(C#Cc2ccc3c(ccc(=O)n3C)c2)n1)N(C)C(=O)OC(C)(C)C] | tert-butyl-N-methyl-N-[1-({6-[2-(1-methyl-2-oxo-1,2-dihydroquinolin-6-yl)ethynyl]-4-(7-methyl-7H-purin-6-yl)pyridin-2-yl}carbamoyl)ethyl]carbamate |
| H9 | 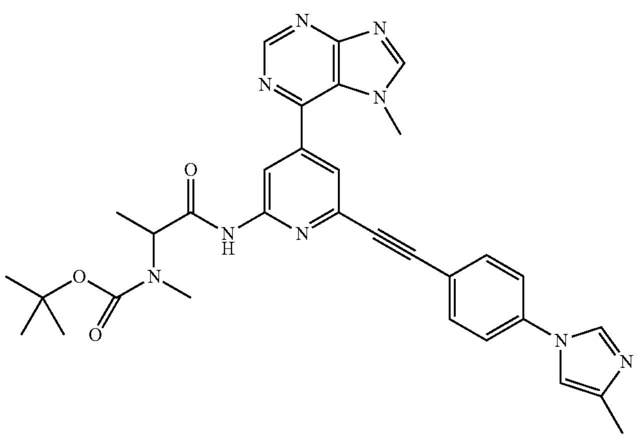 [SMILES: Cc1cn(-c2ccc(C#Cc3cc(-c4ncnc5ncn(C)c45)cc(NC(=O)C(C)N(C)C(=O)OC(C)(C)C)n3)cc2)cn1] | tert-butyl-N-methyl-N-{1-[(6-{2-[4-(4-methyl-1H-imidazol-1-yl)phenyl]ethynyl}-4-(7-methyl-7H-purin-6-yl)pyridin-2-yl)carbamoyl]ethyl}carbamate |
| H10 | 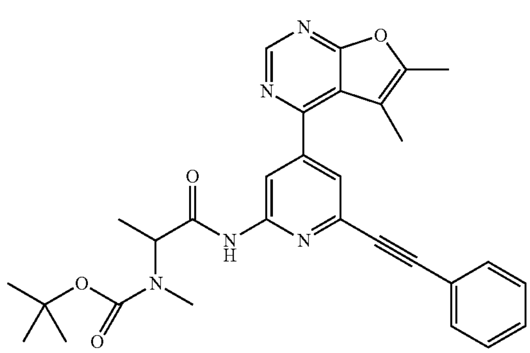 [SMILES: Cc1oc2ncnc(-c3cc(C#Cc4ccccc4)nc(NC(=O)C(C)N(C)C(=O)OC(C)(C)C)c3)c2c1C] | tert-butyl-N-{1-[(4-{5,6-dimethylfuran[2,3-d]pyrimidin-4-yl}-6-(2-phenylethynyl)pyridin-2-yl)carbamoyl]ethyl}-N-methylcarbamate |

| # | Molecular Structure | Chemical Name |
|---|---|---|
| H11 | 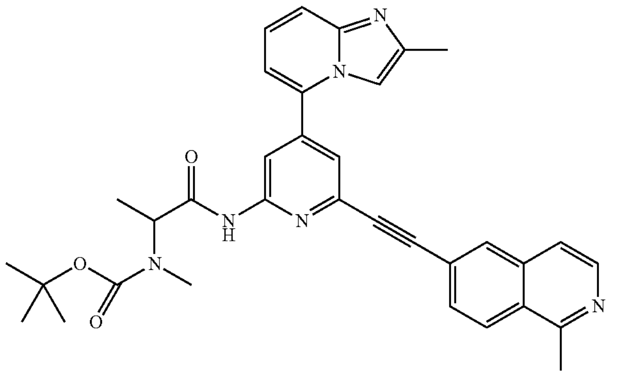 [SMILES: Cc1cn2c(-c3cc(C#Cc4ccc5c(C)nccc5c4)nc(NC(=O)C(C)N(C)C(=O)OC(C)(C)C)c3)cccc2n1] | tert-butyl-N-{1-[(4-{2,3-dimethylimidazo[1,2-a]pyridin-5-yl}-6-[2-(1-methylisoquinolin-6-yl)ethynyl]pyridin-2-yl)carbamoyl]ethyl}-N-methylcarbamate |
| H12 | 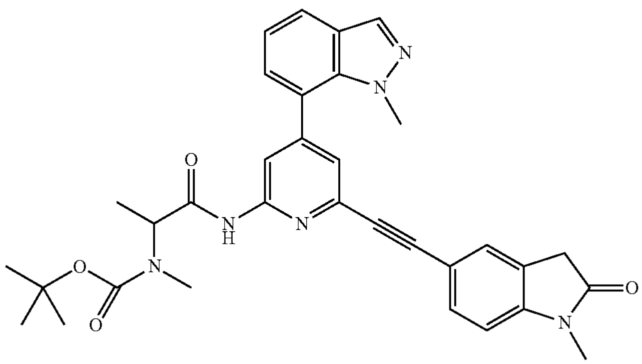 [SMILES: CC(C(=O)Nc1cc(-c2cccc3cnn(C)c23)cc(C#Cc2ccc3c(c2)CC(=O)N3C)n1)N(C)C(=O)OC(C)(C)C] | tert-butyl-N-methyl-N-(1-{[4-(1-methyl-1H-indazol-7-yl)-6-[2-(1-methyl-2-oxo-2,3-dihydro-1H-indol-5-yl)ethynyl]pyridin-2-yl]carbamoyl}ethyl)carbamate |
| H13 | 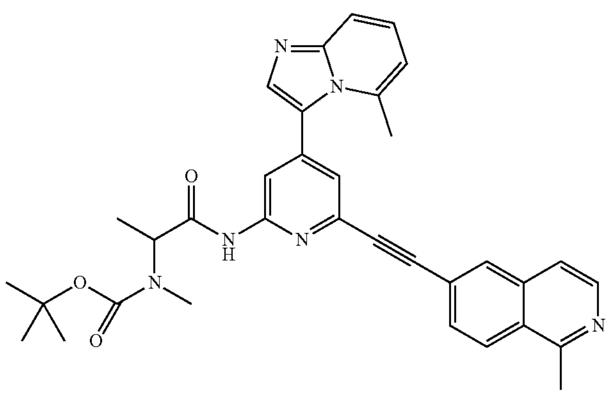 [SMILES: Cc1nccc2cc(C#Cc3cc(-c4cnc5cccc(C)n45)cc(NC(=O)C(C)N(C)C(=O)OC(C)(C)C)n3)ccc12] | tert-butyl-N-methyl-N-{1-[(4-{5-methylimidazo[1,2-a]pyridin-3-yl}-6-[2-(1-methylisoquinolin-6-yl)ethynyl]pyridin-2-yl)carbamoyl]ethyl}carbamate |
| H14 | 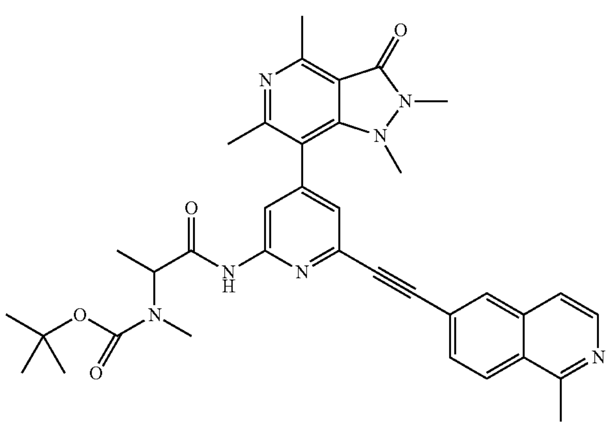 [SMILES: Cc1nc(C)c2c(=O)n(C)n(C)c2c1-c1cc(C#Cc2ccc3c(C)nccc3c2)nc(NC(=O)C(C)N(C)C(=O)OC(C)(C)C)c1] | tert-butyl-N-methyl-N-[1-({6-[2-(1-methylisoquinolin-6-yl)ethynyl]-4-{1,2,4,6-tetramethyl-3-oxo-1H,2H,3H-pyrazolo[4,3-c]pyridin-7-yl}pyridin-2-yl}carbamoyl)ethyl]carbamate |

-continued

| # | Molecular Structure | Chemical Name |
|---|---|---|
| H15 | 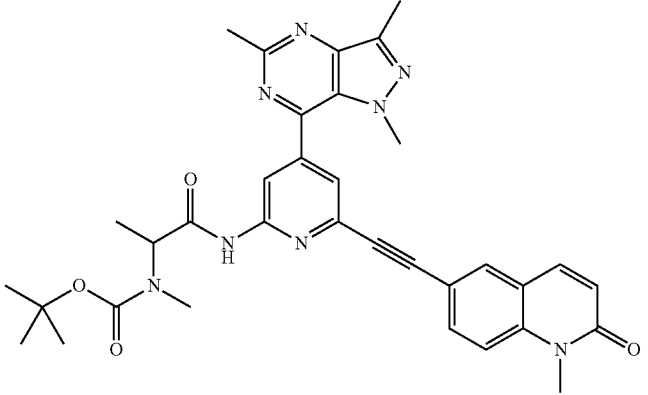 [SMILES: Cc1nc(-c2cc(C#Cc3ccc4c(ccc(=O)n4C)c3)nc(NC(=O)C(C)N(C)C(=O)OC(C)(C)C)c2)c2c(n1)c(C)nn2C] | tert-butyl-N-methyl-N-[1-({6-[2-(1-methyl-2-oxo-1,2-dihydroquinolin-6-yl)ethynyl]-4-{trimethyl-1H-pyrazolo[4,3-d]pyrimidin-7-yl}pyridin-2-yl}carbamoyl)-ethyl]carbamate |
| H16 | 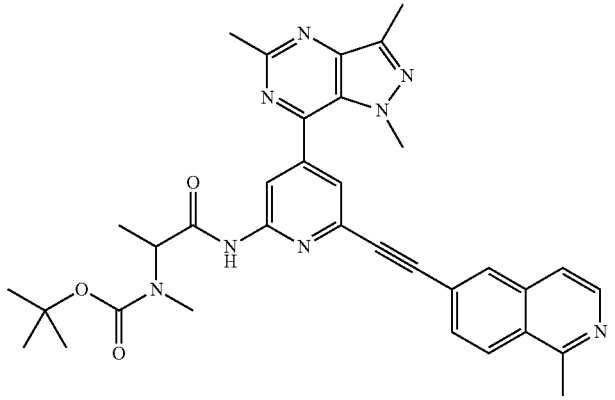 [SMILES: Cc1nc(-c2cc(C#Cc3ccc4c(C)nccc4c3)nc(NC(=O)C(C)N(C)C(=O)OC(C)(C)C)c2)c2c(n1)c(C)nn2C] | tert-butyl-N-methyl-N-[1-({6-[2-(1-methylisoquinolin-6-yl)ethynyl]-4-(trimethyl-1H-pyrazolo[4,3-d]pyrimidin-7-yl}pyridin-2-yl}carbamoyl)ethyl]carbamate |
| H17 | 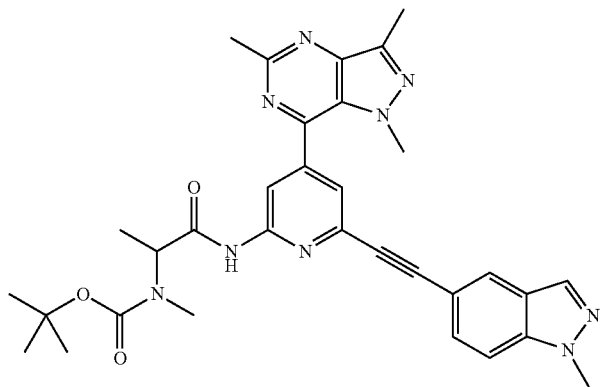 [SMILES: Cc1nc(-c2cc(C#Cc3ccc4c(cnn4C)c3)nc(NC(=O)C(C)N(C)C(=O)OC(C)(C)C)c2)c2c(n1)c(C)nn2C] | tert-butyl-N-methyl-N-[1-({6-[2-(1-methyl-1H-indazol-5-yl)ethynyl]-4-{trimethyl-1H-pyrazolo[4,3-d]pyrimidin-7-yl}pyridin-2-yl]carbamoyl)ethyl]carbamate |

| # | Molecular Structure | Chemical Name |
|---|---|---|
| H18 | 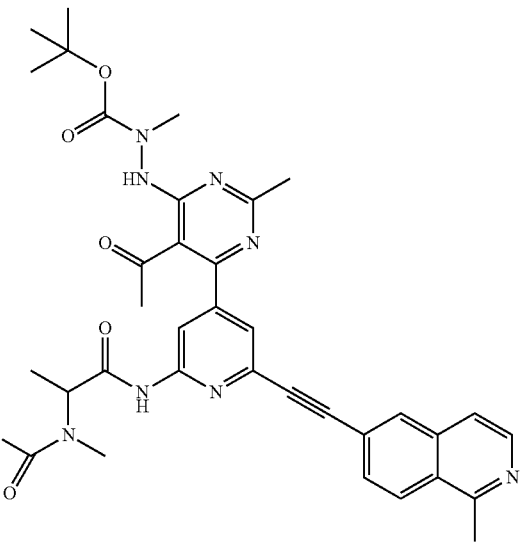 | tert-butyl-N-[1-({4-[5-acetyl-6-({[(tert-butoxy)carbonyl](methyl)-amino}amino)-2-methylpyrimidin-4-yl]-6-[2-(1-methylisoquinolin-6-yl)ethynyl]pyridin-2-yl}carbamoyl)ethyl]-N-methylcarbamate |
| H19 | 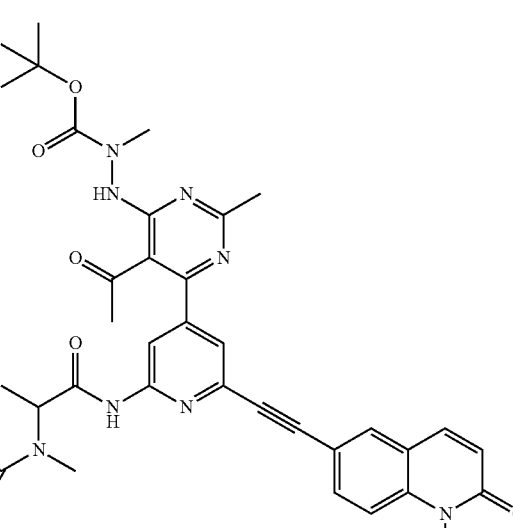 | tert-butyl-N-[1-({4-[5-acetyl-6-({[(tert-butoxy)carbonyl](methyl)-amino}amino)-2-methylpyrimidin-4-yl]-6-[2-(1-methyl-2-oxo-1,2-dihydroquinolin-6-yl)ethynyl]pyridin-6-yl}carbamoyl)ethyl]-N-methylcarbamate |
| H20 | 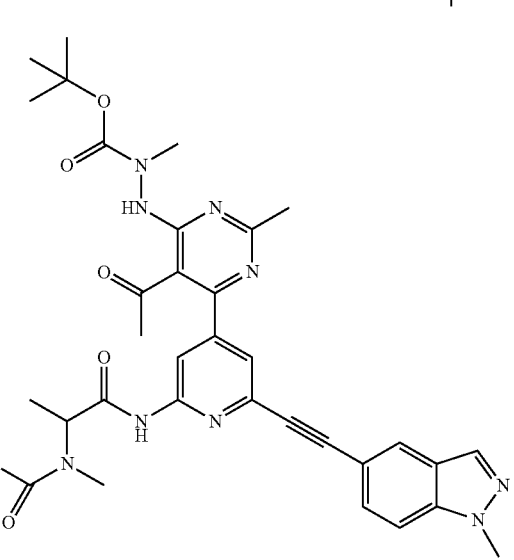 | tert-butyl-N-[1-({4-[5-acetyl-6-({[(tert-butoxy)carbonyl](methyl)-amino}amino)-2-methylpyrimidin-4-yl]-6-[2-(1-methyl-1H-indazol-5-yl)ethynyl]pyridin-2-yl}carbamoyl)ethyl]-N-methylcarbamate |

| # | Molecular Structure | Chemical Name |
|---|---|---|
| H21 | 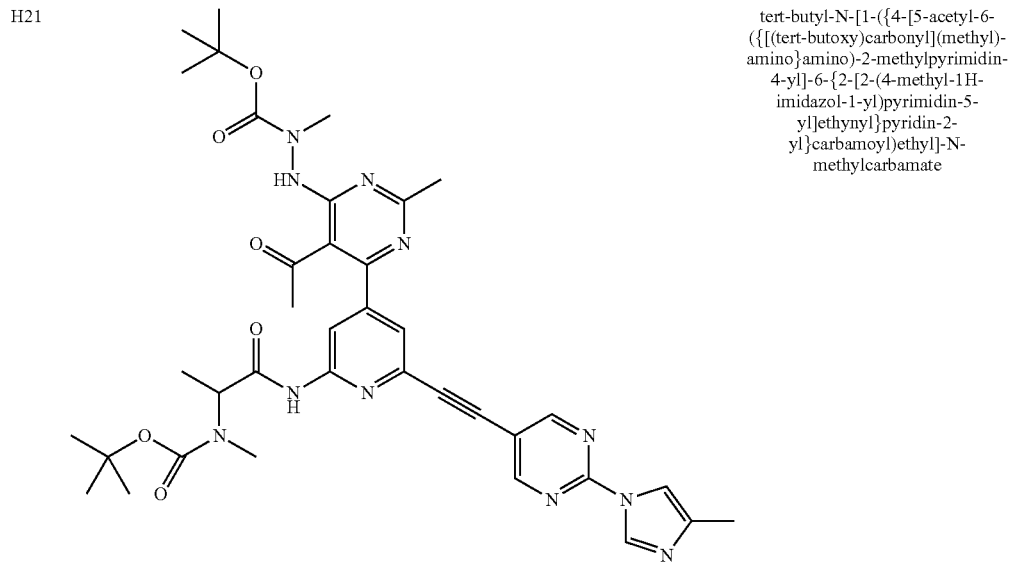 | tert-butyl-N-[1-({4-[5-acetyl-6-({[(tert-butoxy)carbonyl](methyl)-amino}amino)-2-methylpyrimidin-4-yl]-6-{2-[2-(4-methyl-1H-imidazol-1-yl)pyrimidin-5-yl]ethynyl}pyridin-2-yl}carbamoyl)ethyl]-N-methylcarbamate |
| H22 | 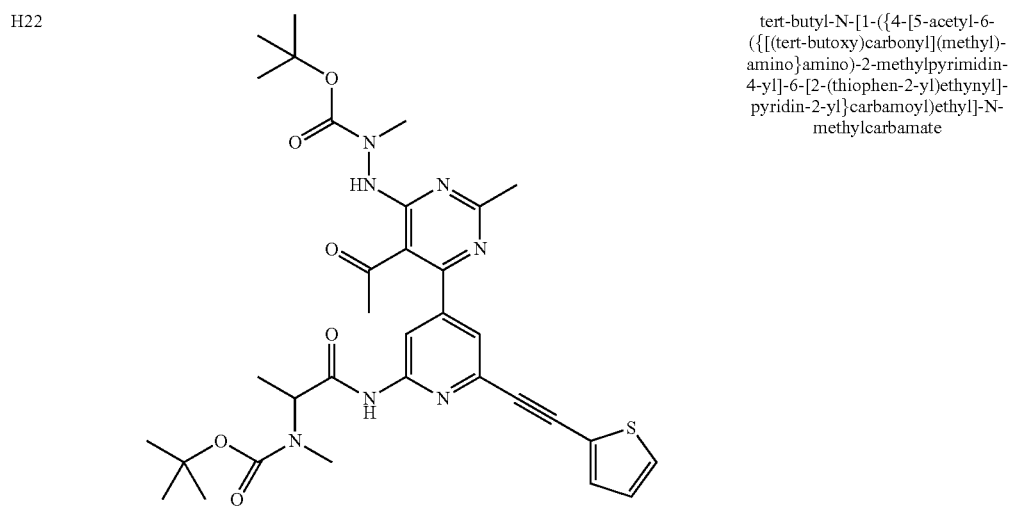 | tert-butyl-N-[1-({4-[5-acetyl-6-({[(tert-butoxy)carbonyl](methyl)-amino}amino)-2-methylpyrimidin-4-yl]-6-[2-(thiophen-2-yl)ethynyl]-pyridin-2-yl}carbamoyl)ethyl]-N-methylcarbamate |

| # | Molecular Structure | Chemical Name |
|---|---|---|
| H23 | 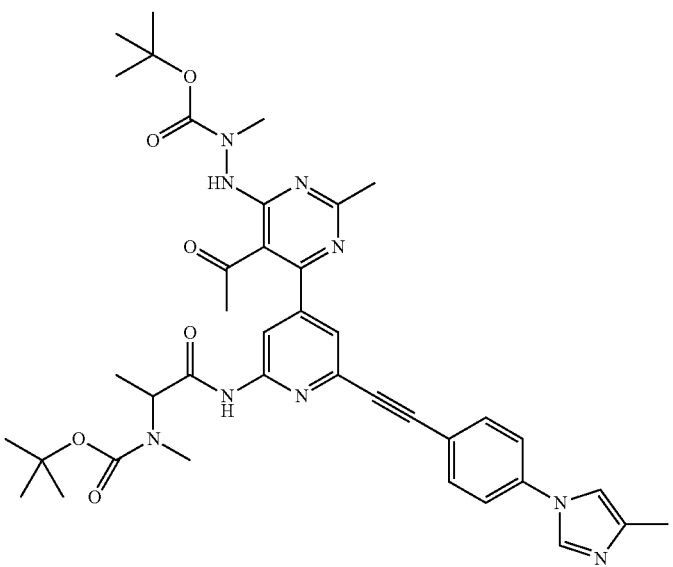 [SMILES: CC(=O)c1c(NN(C)C(=O)OC(C)(C)C)nc(C)nc1-c1cc(C#Cc2ccc(-n3cnc(C)c3)cc2)nc(NC(=O)C(C)N(C)C(=O)OC(C)(C)C)c1] | tert-butyl-N-[1-({4-[5-acetyl-6-({[(tert-butoxy)carbonyl]-(methyl)amino}amino)-2-methyl-pyrimidin-4-yl]-6-{2-[4-(4-methyl-1H-imidazol-1-yl)phenyl]-ethynyl}pyridin-2-yl}-carbamoyl}pyridin-2-yl}-carbamoyl)ethyl]-N-methylcarbamate |
| H24 | 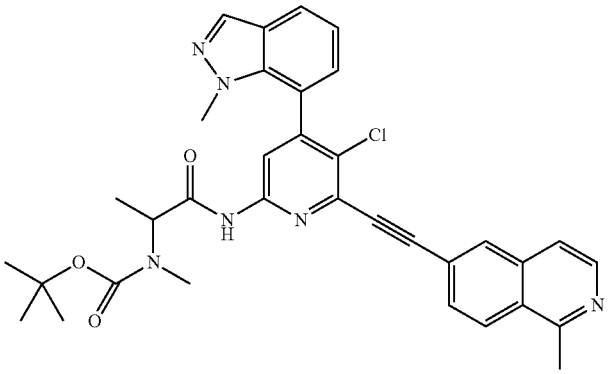 [SMILES: Cc1nccc2cc(C#Cc3nc(NC(=O)C(C)N(C)C(=O)OC(C)(C)C)cc(-c4cccc5cnn(C)c45)c3Cl)ccc12] | tert-butyl-N-(1-{[5-chloro-4-(1-methyl-1H-indazol-7-yl)-6-[2-(1-methylisoquinolin-6-yl)ethynyl]pyridin-2-yl]carbamoyl}ethyl)-N-methylcarbamate |
| H25 | 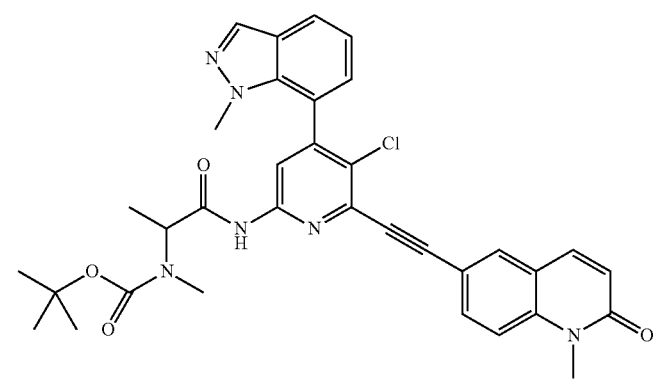 [SMILES: CC(C(=O)Nc1cc(-c2cccc3cnn(C)c23)c(Cl)c(C#Cc2ccc3c(ccc(=O)n3C)c2)n1)N(C)C(=O)OC(C)(C)C] | tert-butyl-N-(1-{[5-chloro-4-(1-methyl-1H-indazol-7-yl)-6-[2-(1-methyl-2-oxo-1,2-dihydroquinolin-6-yl)ethynyl]pyridin-2-yl]carbamoyl}ethyl)-N-methylcarbamate |

-continued

| # | Molecular Structure | Chemical Name |
|---|---|---|
| H35 | 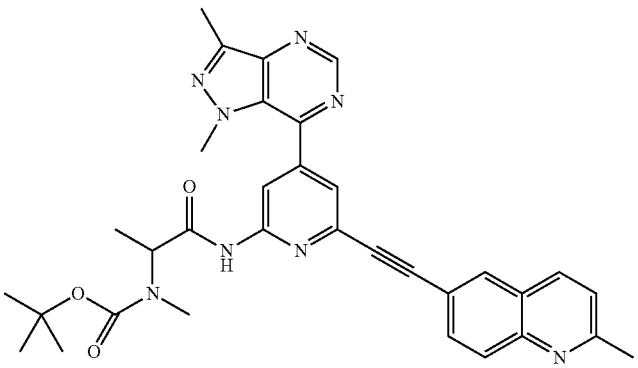 | tert-butyl N-{1-[(4-{1,3-dimethyl-1H-pyrazolo[4,3-d]pyrimidin-7-yl}-6-[2-(2-methylquinolin-6-yl)ethynyl]pyridin-2-yl)carbamoyl]ethyl}-N-methylcarbamate |
| H36 | 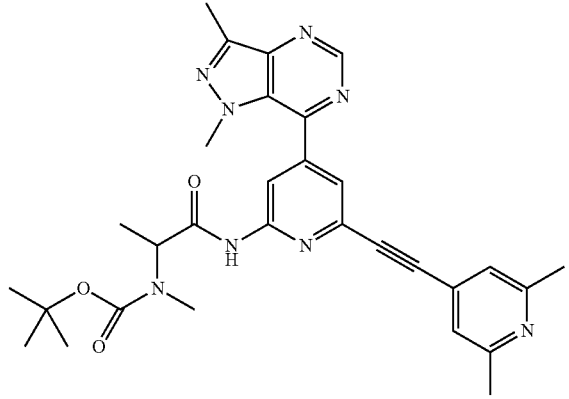 [SMILES: Cc1cc(C#Cc2cc(-c3ncnc4c(C)nn(C)c34)cc(NC(=O)C(C)N(C)C(=O)OC(C)(C)C)n2)cc(C)n1] | tert-butyl N-{1-[(4-{1,3-dimethyl-1H-pyrazolo[4,3-d]pyrimidin-7-yl}-6-[2-(2,6-dimethylpyridin-4-yl)ethynyl]pyridin-2-yl)carbamoyl]ethyl}-N-methylcarbamate |
| H37 | 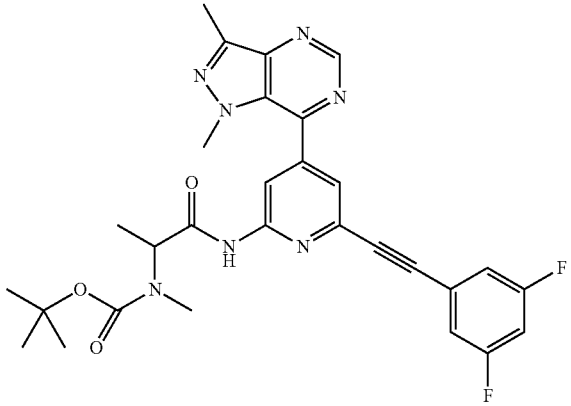 [SMILES: Cc1nn(C)c2c(-c3cc(C#Cc4cc(F)cc(F)c4)nc(NC(=O)C(C)N(C)C(=O)OC(C)(C)C)c3)ncnc12] | tert-butyl N-[1-({6-[2-(3,5-difluorophenyl)ethynyl]-4-{1,3-dimethyl-1H-pyrazolo[4,3-d]pyrimidin-7-yl}pyridin-2-yl}carbamoyl)ethyl]-N-methylcarbamate |
| H38 | 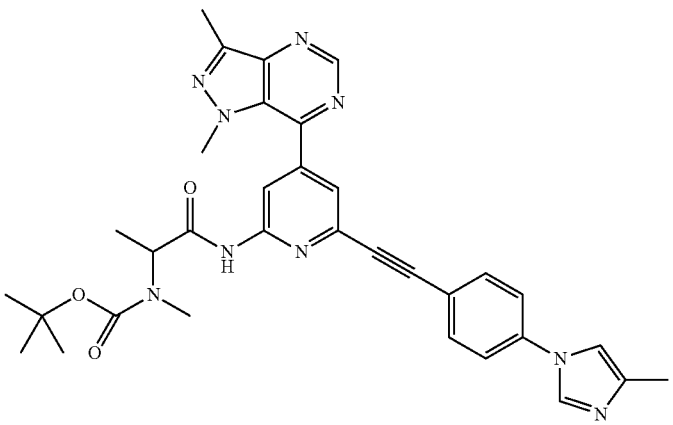 [SMILES: Cc1cn(-c2ccc(C#Cc3cc(-c4ncnc5c(C)nn(C)c45)cc(NC(=O)C(C)N(C)C(=O)OC(C)(C)C)n3)cc2)cn1] | tert-butyl N-{1-[(4-{1,3-dimethyl-1H-pyrazolo[4,3-d]pyrimidin-7-yl}-6-{2-[4-(4-methyl-1H-imidazol-1-yl)phenyl]ethynyl}pyridin-2-yl)carbamoyl]ethyl}-N-methylcarbamate |

-continued

| # | Molecular Structure | Chemical Name |
|---|---|---|
| H39 | 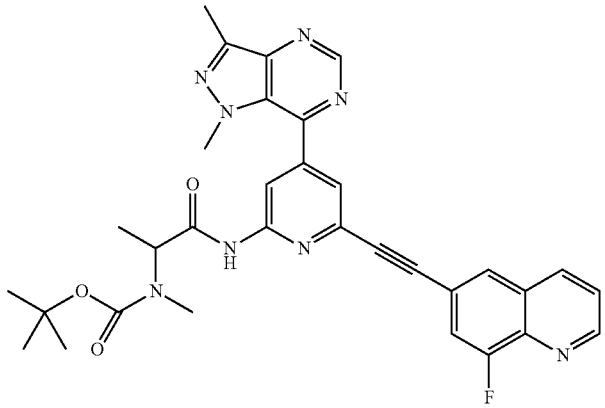 [SMILES: Cc1nn(C)c2c(-c3cc(C#Cc4cc(F)c5ncccc5c4)nc(NC(=O)C(C)N(C)C(=O)OC(C)(C)C)c3)ncnc12] | tert-butyl N-{1-[(4-{1,3-dimethyl-1H-pyrazolo[4,3-d]pyrimidin-7-yl}-6-[2-(8-fluoroquinolin-6-yl)ethynyl]pyridin-2-yl)carbamoyl]ethyl}-N-methylcarbamate |
| H40 | 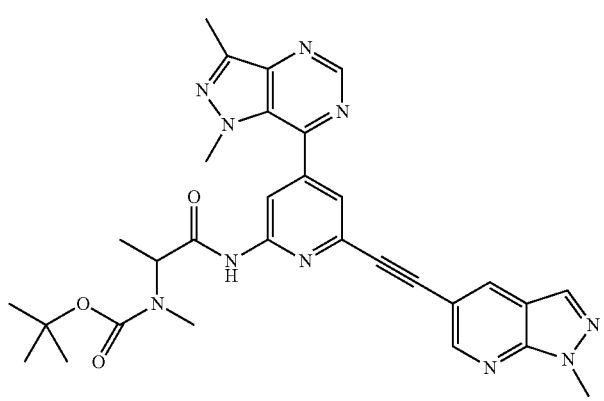 [SMILES: Cc1nn(C)c2c(-c3cc(C#Cc4cnc5c(cnn5C)c4)nc(NC(=O)C(C)N(C)C(=O)OC(C)(C)C)c3)ncnc12] | tert-butyl N-{1-[(4-{1,3-dimethyl-1H-pyrazolo[4,3-d]pyrimidin-7-yl}-6-(2-{1-methyl-1H-pyrazolo[3,4-b]pyridin-5-yl}ethynyl)pyridin-2-yl)carbamoyl]ethyl}-N-methylcarbamate |

H26) tert-butyl-N-(1-{[5-methoxy-4-(1-methyl-1H-indazol-7-yl)-6-(2-phenylethynyl)pyridin-2-yl]carbamoyl}ethyl)-N-methylcarbamate -continued

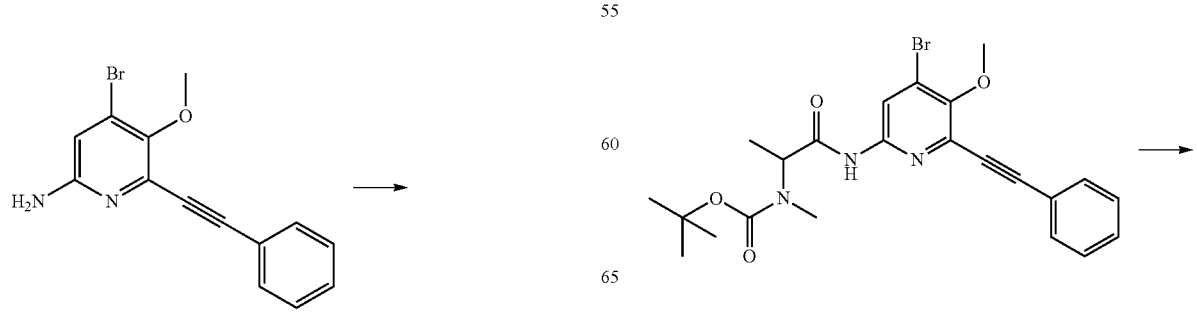

-continued

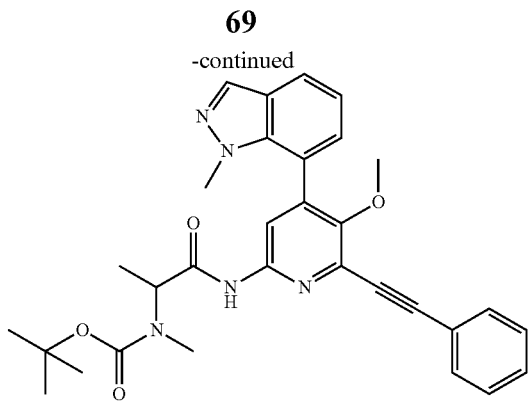

For the preparation of H26, the amidation reaction is performed prior to the introduction of R4.

N,N'-dicyclohexylcarbodiimide (0.27 g, 1.3 mmol) is added slowly to a mixture of 2-[methyl-[(2-methylpropan-2-yl)oxycarbonyl]amino]propanoic acid (0.42 g, 2.1 mmol) in DCM (5 ml) with ice bath cooling. Stirring is continued and the mixture warmed to RT. The mixture is stirred at RT for 30 minutes before 4-bromo-5-methoxy-6-(2-phenylethynyl)pyridin-2-amine F2 (0.26 g, 0.86 mmol) in 5 ml DCM is added dropwise. After stirring for 24 h at RT the reaction mixture is filtered and concentrated in vacuo. The intermediate tert-butyl-N-(1-{[4-bromo-5-methoxy-6-(2-phenylethynyl)pyridin-2-yl]-carbamoyl}ethyl)-N-methylcarbamate is purified by RP HPLC. Yield: 0.23 g (54%). HPLC-MS: M+H=488/490; tR=1.14 min (METHOD_3).

Tetrakis(triphenylphosphine)palladium(0) (24 mg, 20 μmol) is added to a mixture of tert-butyl-N-(1-{[4-bromo-5-methoxy-6-(2-phenylethynyl)pyridin-2-yl]carbamoyl}ethyl)-N-methylcarbamate (0.1 g, 0.20 mmol)), 1-methylindazole-7-boronic acid (54 mg, 0.31 mmol), sodium carbonate (65 mg, 0.61 mmol), water (0.5 ml) and dioxane (2 ml) under argon atmosphere at RT and is stirred at 85° C. for 5 h. The mixture is diluted with DCM and extracted with a saturated aqueous sodium hydrogencarbonate solution. The combined organic layers are dried over MgSO₄ and concentrated in vacuo. The product is purified by RP HPLC. Yield: 78 mg (71%). HPLC-MS: M+H=540; tR=1.15 min (METHOD_3).

The following compound is prepared analogously utilizing (quinolin-5-yl)boronic acid:

H28) tert-butyl-N-methyl-N-(1-{[6-(2-phenylethynyl)-4-(pyridin-4-yl)pyridin-2-yl]-carbamoyl}ethyl) carbamate

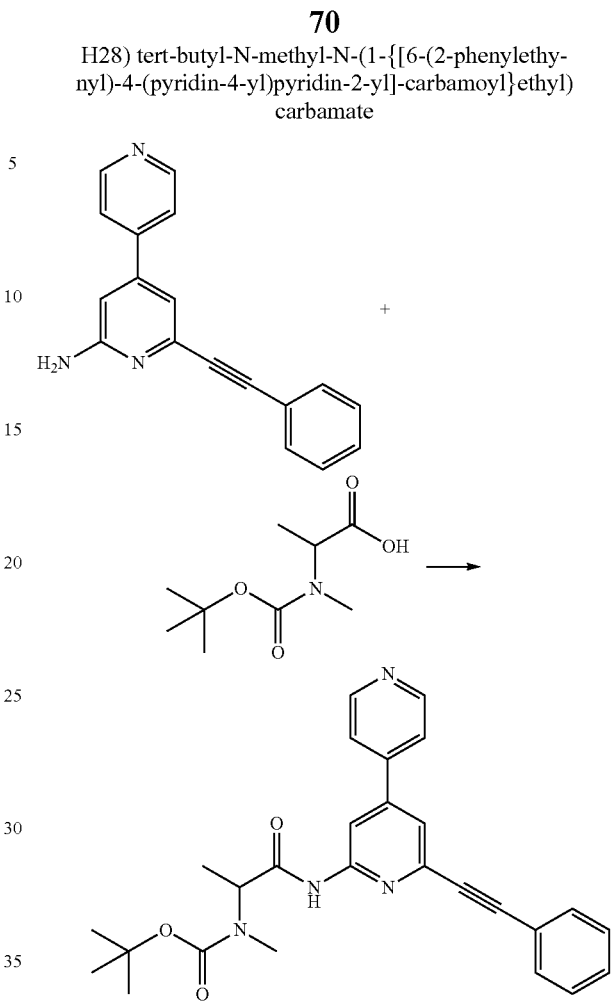

A mixture of 2-[methyl-[(2-methylpropan-2-yl)oxycarbonyl]amino]propanoic acid (1.44 g, 7.1 mmol) and N,N'-dicyclohexylcarbodiimide (0.73 g, 3.55 mmol) in DCM (4 ml) is stirred for 30 minutes at RT. This mixture is added in 4 portions over 48 h via syringe filter to a mixture of 6-(2-phenylethynyl)-4-(pyridin-4-yl)pyridin-2-amine G1 (0.24 g, 0.89 mmol), DIPEA (166 μl, 0.98 mmol) and NMP (2 ml) at 50° C. After stirring for another 16 h at 50° C. the mixture is filtered and the product purified by RP HPLC. Yield: 56 mg (14%). HPLC-MS: M+H=457; tR=.2.08 min (METHOD_2).

| # | Molecular Structure | Chemical Name |
|---|---|---|
| H27 | 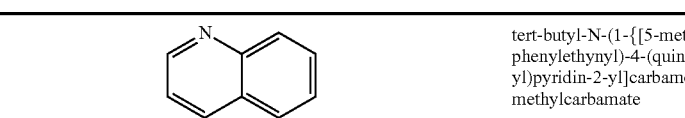 | tert-butyl-N-(1-{[5-methoxy-6-(2-phenylethynyl)-4-(quinolin-5-yl)pyridin-2-yl]carbamoyl}ethyl)-N-methylcarbamate |

The following compounds are prepared analogously from G2-G7, respectively:

| # | Molecular Structure | Chemical Name |
|---|---|---|
| H29 | 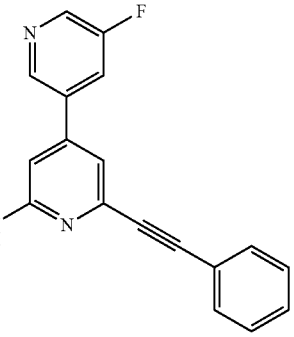 | tert-butyl-N-(1-{[4-(5-fluoropyridin-3-yl)-6-(2-phenylethynyl)pyridin-2-yl]carbamoyl}ethyl)-N-methylcarbamate |
| H30 | 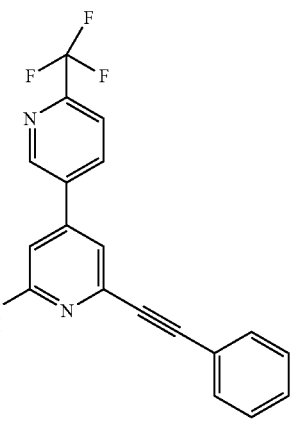 | tert-butyl-N-methyl-N-(1-{[6-(2-phenylethynyl)-4-[6-(trifluoromethyl)pyridin-3-yl]pyridin-2-yl]carbamoyl}ethyl)carbamate |
| H31 | 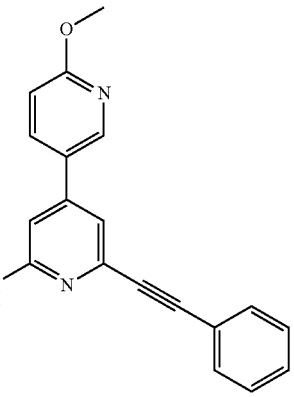 | tert-butyl-N-(1-{[4-(6-methoxypyridin-3-yl)-6-(2-phenylethynyl)pyridin-2-yl]carbamoyl}ethyl)-N-methylcarbamate |
| H32 | 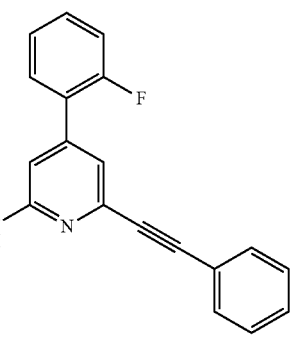 | tert-butyl-N-(1-{[4-(2-fluorophenyl)-6-(2-phenylethynyl)pyridin-2-yl]carbamoyl}ethyl)-N-methylcarbamate |

-continued

| # | Molecular Structure | Chemical Name |
|---|---|---|
| H33 | 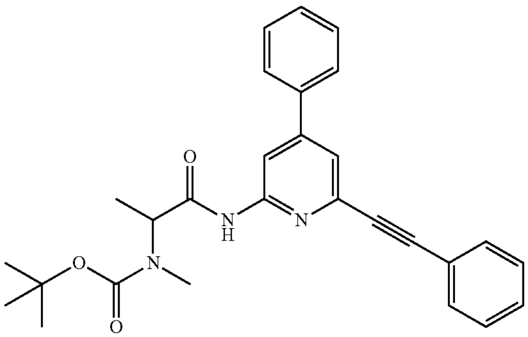 [SMILES: CC(C(=O)Nc1cc(-c2ccccc2)cc(C#Cc2ccccc2)n1)N(C)C(=O)OC(C)(C)C] | tert-butyl-N-methyl-N-(1-{[4-phenyl-6-(2-phenylethynyl)pyridin-2-yl]carbamoyl}ethyl)carbamate |
| H34 | 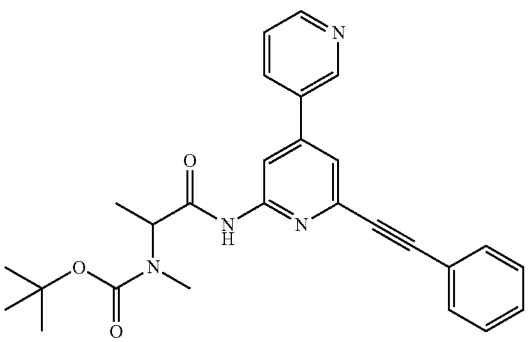 [SMILES: CC(C(=O)Nc1cc(-c2cccnc2)cc(C#Cc2ccccc2)n1)N(C)C(=O)OC(C)(C)C] | tert-butyl-N-methyl-N-(1-{[6-(2-phenylethynyl)-4-(pyridin-3-yl)pyridin-2-yl]carbamoyl}-ethyl)carbamate |

Preparation of Examples (I)

Example 1

N-(4-{1,3-dimethyl-1H-pyrazolo[4,3-d]pyrimidin-7-yl}-6-[2-(1-methyl-1H-indazol-5-yl)ethynyl]pyridin-2-yl)-2-(methylamino)propanamide

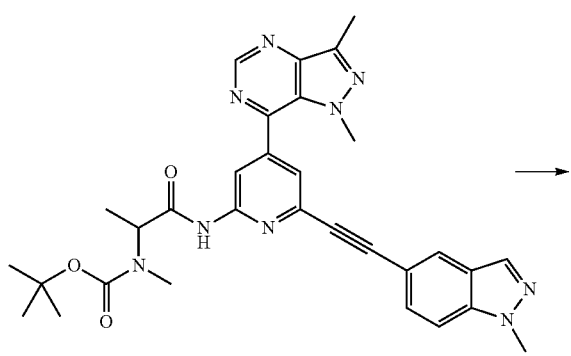

→

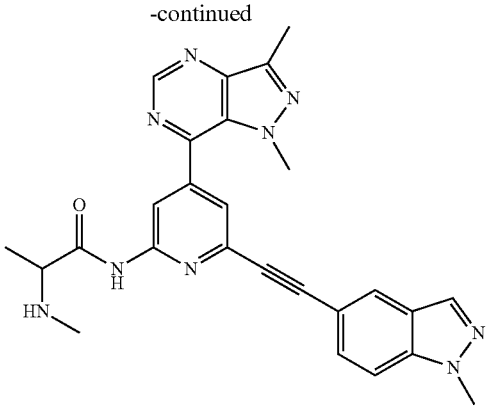

A mixture of tert-butyl-N-{1-[(4-{1,3-dimethyl-1H-pyrazolo[4,3-d]pyrimidin-7-yl}-6-[2-(1-methyl-1H-indazol-5-yl)ethynyl]pyridin-2-yl)carbamoyl]ethyl}-N-methylcarbamate H1 (246 mg, 0.42 mmol), DCM (5 ml) and TFA (1 ml) is stirred at RT for 1 h. 50 ml of a saturated aqueous sodium hydrogencarbonate solution is added and the mixture extracted with DCM. The combined organic layers are dried over MgSO$_4$ and concentrated in vacuo. The product is purified by RP HPLC. Yield: 99 mg (49%). HPLC-MS: M+H=480; tR=1.16 min (METHOD_1).

Examples 2-17, 24-34 and 38-43 are prepared analogously, starting from H2-H7, H24-H34 and H35-H40, respectively:

| # | Molecular Structure | Chemical Name | HPLC-MS (Method_1) |
|---|---|---|---|
| 2 | 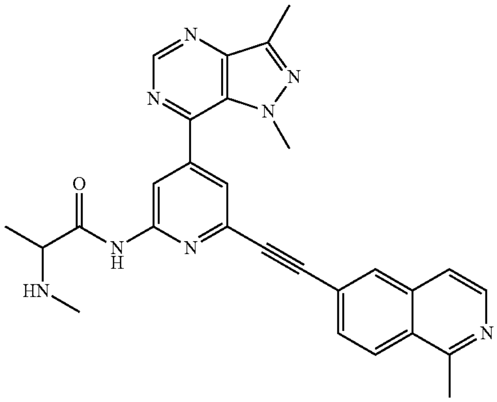 [SMILES: CNC(C)C(=O)Nc1cc(-c2ncnc3c(C)nn(C)c23)cc(C#Cc2ccc3c(C)nccc3c2)n1] | N-(4-{1,3-dimethyl-1H-pyrazolo[4,3-d]pyrimidin-7-yl}-6-[2-(1-methylisoquinolin-6-yl)ethynyl]pyridin-2-yl)-2-(methylamino)propanamide | M + H = 491; tR = 1.17 |
| 3 | 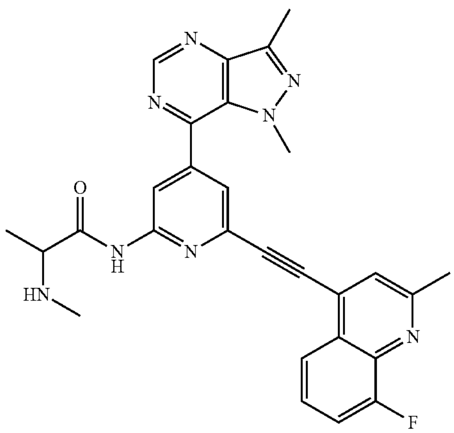 [SMILES: CNC(C)C(=O)Nc1cc(-c2ncnc3c(C)nn(C)c23)cc(C#Cc2cc(C)nc3c(F)cccc23)n1] | N-(4-{1,3-dimethyl-1H-pyrazolo[4,3-d]pyrimidin-7-yl}-6-[2-(8-fluoro-2-methylquinolin-4-yl)ethynyl]pyridin-2-yl)-2-(methylamino)propanamide | M + H = 509; tR = 1.25 |
| 4 | 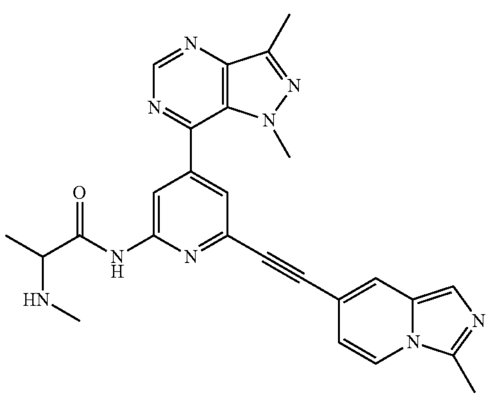 [SMILES: CNC(C)C(=O)Nc1cc(-c2ncnc3c(C)nn(C)c23)cc(C#Cc2ccn3c(C)ncc3c2)n1] | N-(4-{1,3-dimethyl-1H-pyrazolo[4,3-d]pyrimidin-7-yl}-6-(2-{3-methylimidazo[1,5-a]pyridin-7-yl}ethynyl)pyridin-2-yl)-2-(methylamino)propanamide | M + H = 480; tR = 1.05 |
| 5 | 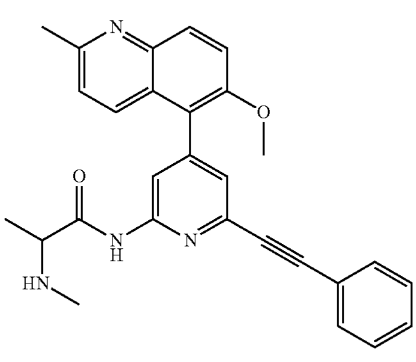 [SMILES: CNC(C)C(=O)Nc1cc(-c2c(OC)ccc3nc(C)ccc23)cc(C#Cc2ccccc2)n1] | N-[4-(6-methoxy-2-methylquinolin-5-yl)-6-(2-phenylethynyl)pyridin-2-yl]-2-(methylamino)propanamide | M + H = 451; tR = 1.36 |

-continued

| # | Molecular Structure | Chemical Name | HPLC-MS (Method_1) |
|---|---|---|---|
| 6 | 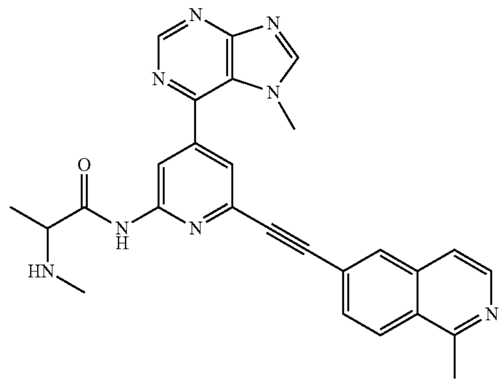 [SMILES: CNC(C)C(=O)Nc1cc(-c2ncnc3ncn(C)c23)cc(C#Cc2ccc3c(C)nccc3c2)n1] | N-[4-(7-methyl-7H-purin-6-yl)-6-[2-(1-methylisoquinolin-6-yl)ethynyl]pyridin-2-yl]-2-(methylamino)propanamide | M + H = 477; tR = 0.98 |
| 7 | 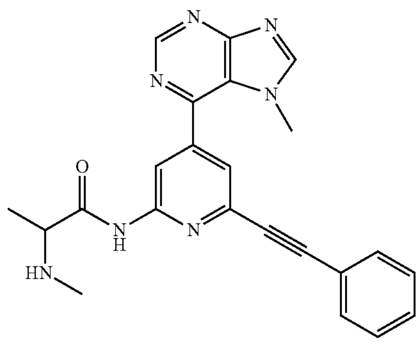 [SMILES: CNC(C)C(=O)Nc1cc(-c2ncnc3ncn(C)c23)cc(C#Cc2ccccc2)n1] | N-[4-(7-methyl-7H-purin-6-yl)-6-(2-phenylethynyl)pyridin-2-yl]-2-(methylamino)propanamide | M + H = 412; tR = 1.03 |
| 8 | 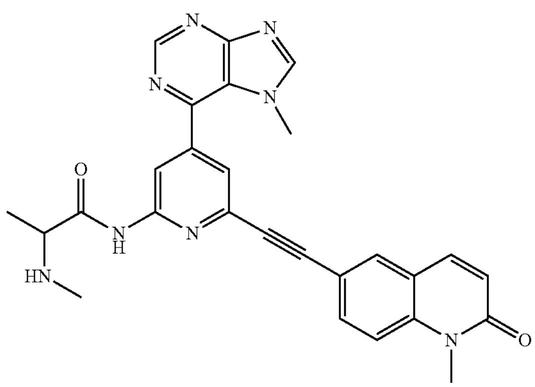 [SMILES: CNC(C)C(=O)Nc1cc(-c2ncnc3ncn(C)c23)cc(C#Cc2ccc3c(ccc(=O)n3C)c2)n1] | N-{6-[2-(1-methyl-2-oxo-1,2-dihydroquinolin-6-yl)ethynyl]-4-(7-methyl-7H-purin-6-yl)pyridin-2-yl}-2-(methylamino)propanamide | M + H = 493; tR = 0.88 |
| 9 | 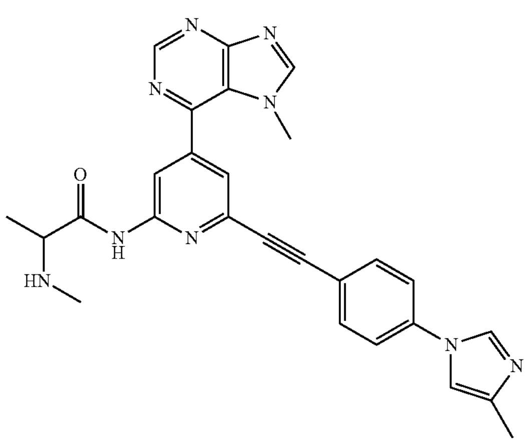 [SMILES: CNC(C)C(=O)Nc1cc(-c2ncnc3ncn(C)c23)cc(C#Cc2ccc(-n3cnc(C)c3)cc2)n1] | N-(6-{2-[4-(4-methyl-1H-imidazol-1-yl)phenyl]ethynyl}-4-(7-methyl-7H-purin-6-yl)pyridin-2-yl)-2-(methylamino)propanamide | M + H = 492; tR = 0.95 |

| # | Molecular Structure | Chemical Name | HPLC-MS (Method_1) |
|---|---|---|---|
| 10 | 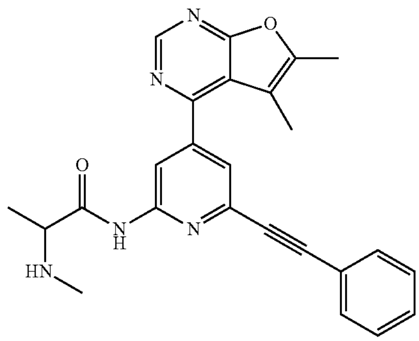 [SMILES: CNC(C)C(=O)Nc1cc(-c2ncnc3oc(C)c(C)c23)cc(C#Cc2ccccc2)n1] | N-(4-{5,6-dimethylfuro[2,3-d]pyrimidin-4-yl}-6-(2-phenylethynyl)pyridin-2-yl)-2-(methylamino)propanamide | M + H = 426; tR = 1.37 |
| 11 | 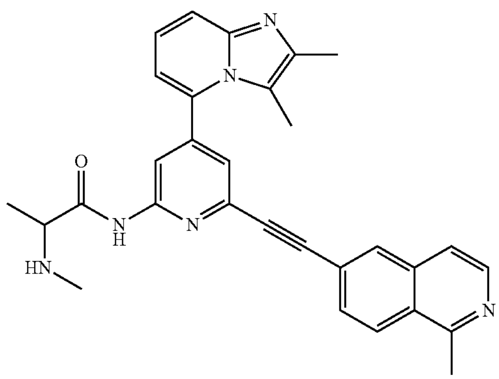 [SMILES: CNC(C)C(=O)Nc1cc(-c2cccc3nc(C)c(C)n23)cc(C#Cc2ccc3c(C)nccc3c2)n1] | N-(4-{2,3-dimethylimidazo[1,2-a]pyridin-5-yl}-6-[2-(1-methylisoquinolin-6-yl)ethynyl]pyridin-2-yl)-2-(methylamino)propanamide | M + H = 489; tR = 1.20 |
| 12 | 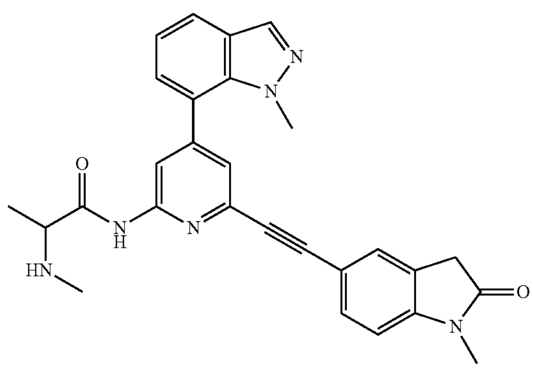 [SMILES: CNC(C)C(=O)Nc1cc(-c2cccc3cnn(C)c23)cc(C#Cc2ccc3c(c2)CC(=O)N3C)n1] | N-[4-(1-methyl-1H-indazol-7-yl)-6-[2-(1-methyl-2-oxo-2,3-dihydro-1H-indol-5-yl)ethynyl]pyridin-2-yl]-2-(methylamino)propanamide | M + H = 479; tR = 1.22 |
| 13 | 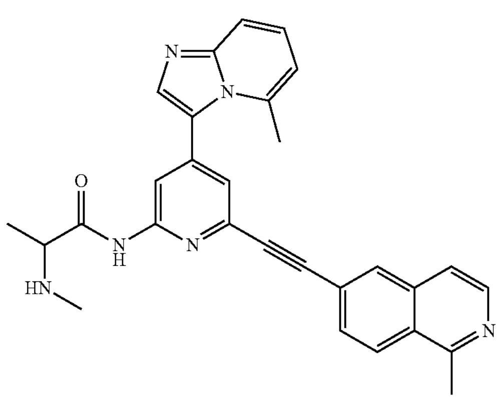 [SMILES: CNC(C)C(=O)Nc1cc(-c2cnc3cccc(C)n23)cc(C#Cc2ccc3c(C)nccc3c2)n1] | 2-(methylamino)-N-(4-{5-methylimidazo[1,2-a]pyridin-3-yl}-6-[2-(1-methylisoquinolin-6-yl)ethynyl]pyridin-2-yl)propanamide | M + H = 475; tR = 1.19 |

-continued

| # | Molecular Structure | Chemical Name | HPLC-MS (Method_1) |
|---|---|---|---|
| 14 | 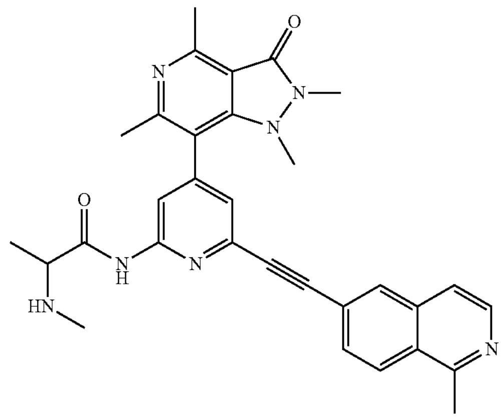 [SMILES: CNC(C)C(=O)Nc1cc(-c2c(C)nc(C)c3c(=O)n(C)n(C)c23)cc(C#Cc2ccc3c(C)nccc3c2)n1] | 2-(methylamino)-N-{6-[2-(1-methylisoquinolin-6-yl)ethynyl]-4-{1,2,4,6-tetramethyl-3-oxo-1H,2H,3H-pyrazolo[4,3-c]pyridin-7-yl}pyridin-2-yl}propanamide | M + H = 534; tR = 1.02 |
| 15 | 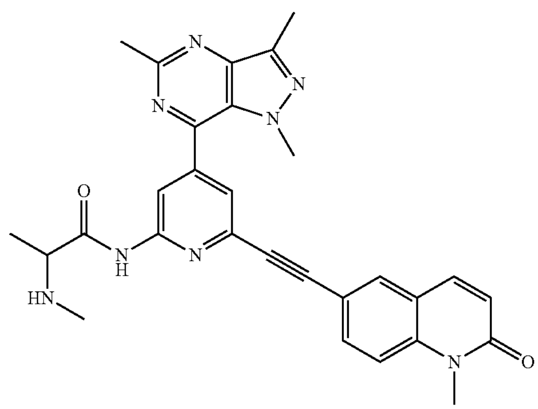 [SMILES: CNC(C)C(=O)Nc1cc(-c2nc(C)nc3c(C)nn(C)c23)cc(C#Cc2ccc3c(ccc(=O)n3C)c2)n1] | N-{6-[2-(1-methyl-2-oxo-1,2-dihydroquinolin-6-yl)ethynyl]-4-{trimethyl-1H-pyrazolo[4,3-d]pyrimidin-7-yl}pyridin-2-yl}-2-(methylamino)propanamide | M + H = 521; tR = 1.12 |
| 16 | 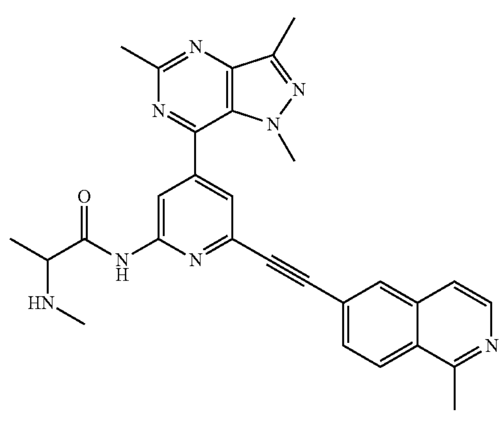 [SMILES: CNC(C)C(=O)Nc1cc(-c2nc(C)nc3c(C)nn(C)c23)cc(C#Cc2ccc3c(C)nccc3c2)n1] | 2-(methylamino)-N-{6-[2-(1-methylisoquinolin-6-yl)ethynyl]-4-{trimethyl-1H-pyrazolo[4,3-d]pyrimidin-7-yl}pyridin-2-yl}propanamide | M + H = 505; tR = 1.25 |

-continued

| # | Molecular Structure | Chemical Name | HPLC-MS (Method_1) |
|---|---|---|---|
| 17 | 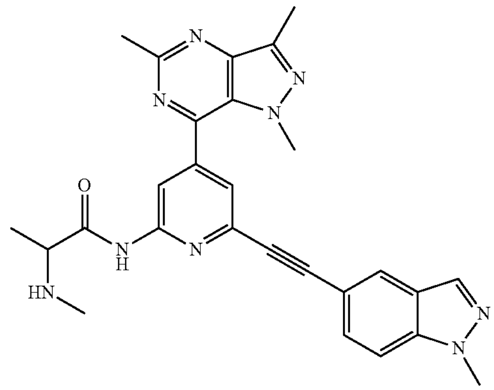 [SMILES: CNC(C)C(=O)Nc1cc(-c2nc(C)nc3c(C)nn(C)c23)cc(C#Cc2ccc3c(cnn3C)c2)n1] | N-{6-[2-(1-methyl-1H-indazol-5-yl)ethynyl]-4-{trimethyl-1H-pyrazolo[4,3-d]pyrimidin-7-yl}pyridin-2-yl}-2-(methylamino)propanamide | M + H = 494; tR = 1.20 |
| 38 | 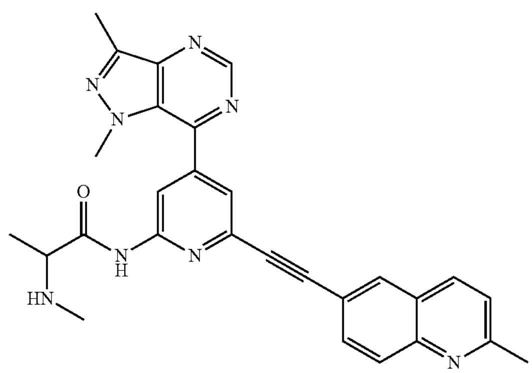 [SMILES: CNC(C)C(=O)Nc1cc(-c2ncnc3c(C)nn(C)c23)cc(C#Cc2ccc3nc(C)ccc3c2)n1] | N-(4-{1,3-dimethyl-1H-pyrazolo[4,3-d]pyrimidin-7-yl}-6-[2-(2-methylquinolin-6-yl)ethynyl]pyridin-2-yl)-2-(methylamino)propanamide | M + H = 491; tR = 1.22 |
| 39 | 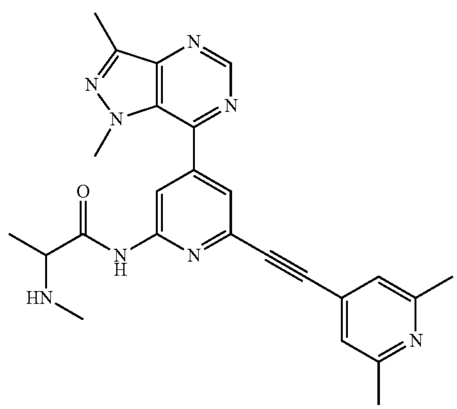 [SMILES: CNC(C)C(=O)Nc1cc(-c2ncnc3c(C)nn(C)c23)cc(C#Cc2cc(C)nc(C)c2)n1] | N-(4-{1,3-dimethyl-1H-pyrazolo[4,3-d]pyrimidin-7-yl}-6-[2-(2,6-dimethyl-pyridin-4-yl)ethynyl]pyridin-2-yl)-2-(methylamino)-propanamide | M + H = 455; tR = 1.13 |
| 40 | 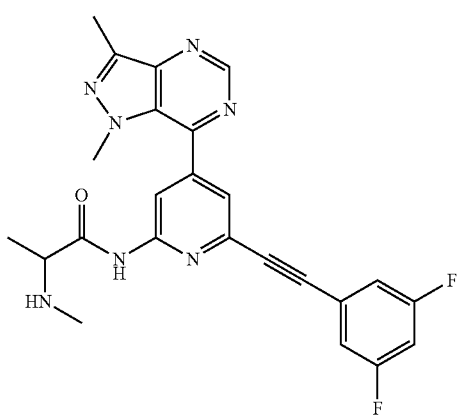 [SMILES: CNC(C)C(=O)Nc1cc(-c2ncnc3c(C)nn(C)c23)cc(C#Cc2cc(F)cc(F)c2)n1] | N-{6-[2-(3,5-difluorophenyl)ethynyl]-4-{1,3-dimethyl-1H-pyrazolo[4,3-d]pyrimidin-7-yl}pyridin-2-yl}-2-(methylamino)propanamide | M + H = 462; tR = 1.34 |

-continued

| # | Molecular Structure | Chemical Name | HPLC-MS (Method_1) |
|---|---|---|---|
| 41 | 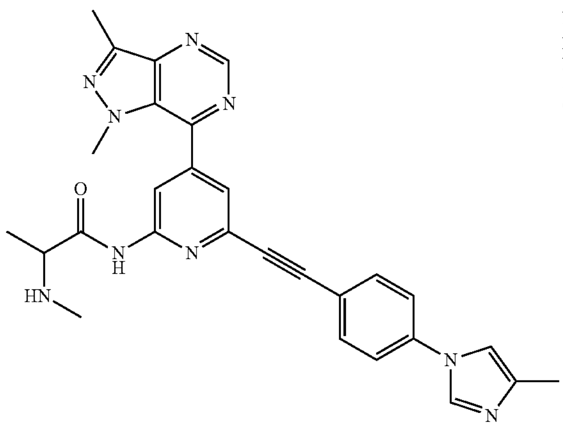 [SMILES: CNC(C)C(=O)Nc1cc(-c2ncnc3c(C)nn(C)c23)cc(C#Cc2ccc(-n3cnc(C)c3)cc2)n1] | N-(4-{1,3-dimethyl-1H-pyrazolo[4,3-d]pyrimidin-7-yl}-6-{2-[4-(4-methyl-1H-imidazol-1-yl)phenyl]-ethynyl}pyridin-2-yl)-2-(methylamino)propanamide | M + H = 506; tR = 1.14 |
| 42 | 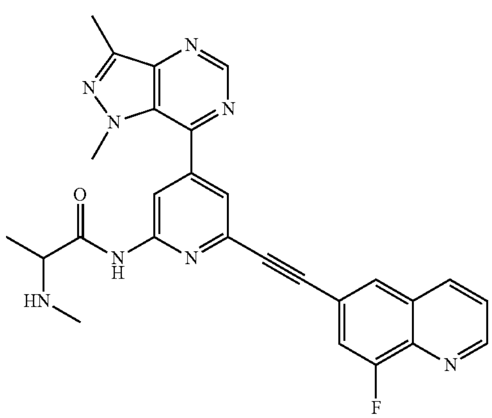 [SMILES: CNC(C)C(=O)Nc1cc(-c2ncnc3c(C)nn(C)c23)cc(C#Cc2cc(F)c3ncccc3c2)n1] | N-(4-{1,3-dimethyl-1H-pyrazolo[4,3-d]pyrimidin-7-yl}-6-[2-(8-fluoroquinolin-6-yl)ethynyl]pyridin-2-yl)-2-(methylamino)propanamide | M + H = 495; tR = 1.16 |
| 43 | 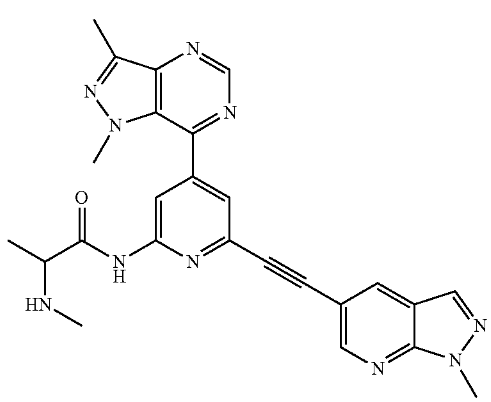 [SMILES: CNC(C)C(=O)Nc1cc(-c2ncnc3c(C)nn(C)c23)cc(C#Cc2cnc3c(cnn3C)c2)n1] | N-(4-{1,3-dimethyl-1H-pyrazolo[4,3-d]pyrimidin-7-yl}-6-(2-{1-methyl-1H-pyrazolo[3,4-b]pyridin-5-yl}ethynyl)pyridin-2-yl)-2-(methylamino)propanamide | M + H = 481; tR = 1.09 |

Example 18

2-(methylamino)-N-{6-[2-(1-methylisoquinolin-6-yl)ethynyl]-4-{trimethyl-2H-pyrazolo[3,4-d]pyrimidin-4-yl}pyridin-2-yl}-propanamide

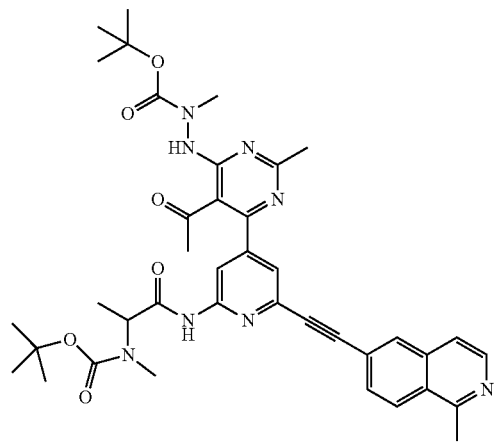

→

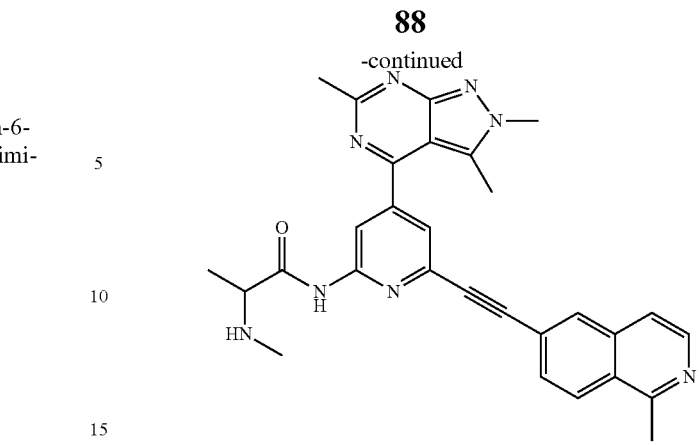

A mixture of tert-butyl-N-[1-({4-[5-acetyl-6-({[tert-butoxy)carbonyl](methyl)amino}-amino)-2-methylpyrimidin-4-yl]-6-[2-(1-methylisoquinolin-6-yl-ethynyl]pyridin-2-yl}-carbamoyl)-ethyl]-N-methylcarbamate H18 (130 mg, 180 μmol), DCM (4 ml) and TFA (1 ml) is stirred for 1 h at RT. A saturated aqueous sodium hydrogencarbonate solution (50 ml) is added and the mixture extracted with DCM. The combined organic layers are dried over MgSO₄ and concentrated in vacuo. The product is purified by RP HPLC. Yield: 46 mg (51%). HPLC-MS: M+H=505; tR=1.07 min (METHOD_1).

The examples 19-23 are prepared analogously from H19-H23.

| # | Molecular Structure | Chemical Name | HPLC-MS (Method_1) |
|---|---|---|---|
| 19 | ![structure] | N-{6-[2-(1-methyl-2-oxo-1,2-dihydroquinolin-6-yl)ethynyl]-4-{trimethyl-2H-pyrazolo[3,4-d]pyrimidin-4-yl}pyridin-2-yl}-2-(methylamino)propanamide | M + H = 521; tR = 0.96 |
| 20 | ![structure] | N-{6-[2-(1-methyl-1H-indazol-5-yl)ethynyl]-4-{trimethyl-2H-pyrazolo[3,4-d]pyrimidin-4-yl}pyridin-2-yl}-2-(methylamino)-propanamide | M + H = 494; tR = 1.04 |

| # | Molecular Structure | Chemical Name | HPLC-MS (Method_1) |
|---|---|---|---|
| 21 | 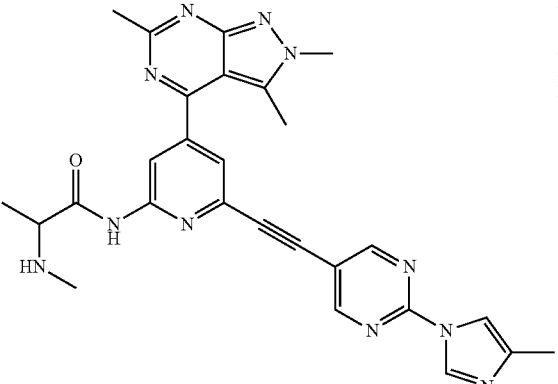 | N-(6-{2-[2-(4-methyl-1H-imidazol-1-yl)pyrimidin-5-yl]ethynyl}-4-{trimethyl-2H-pyrazolo[3,4-d]pyrimidin-4-yl}pyridin-2-yl)-2-(methyl-amino)propanamide | M + H = 522; tR = 1.01 |
| 22 | 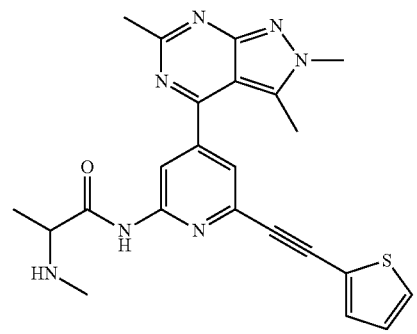 [SMILES: CNC(C)C(=O)Nc1cc(-c2nc(C)nc3nn(C)c(C)c23)cc(C#Cc2cccs2)n1] | 2-(methylamino)-N-{6-[2-(thiophen-2-yl)ethynyl]-4-{trimethyl-2H-pyrazolo[3,4-d]pyrimidin-4-yl}pyridin-2-yl}propanamide | M + H = 446; tR = 1.11 |
| 23 | 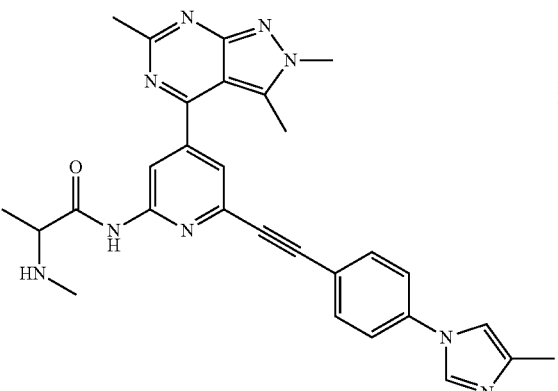 | (2S)-N-(6-{2-[4-(4-methyl-1H-imidazol-1-yl)phenyl]-ethynyl}-4-{trimethyl-2H-pyrazolo[3,4-d]pyrimidin-4-yl}pyridin-2-yl)-2-(methyl-amino)propanamide | M + H = 520; tR = 1.04 |
| 24 | 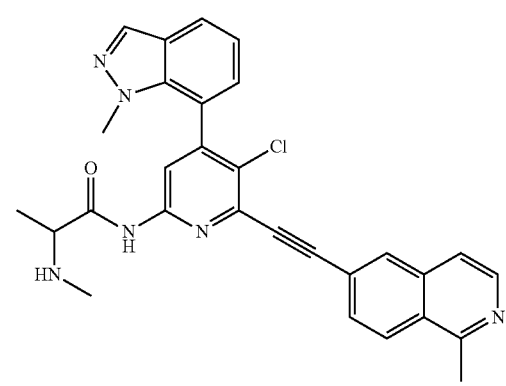 [SMILES: CNC(C)C(=O)Nc1cc(-c2cccc3cnn(C)c23)c(Cl)c(C#Cc2ccc3c(C)nccc3c2)n1] | N-[5-chloro-4-(1-methyl-1H-indazol-7-yl)-6-[2-(1-methylisoquinolin-6-yl)ethynyl]pyridin-2-yl]-2-(methylamino)propanamide | M + H = 509; tR = 1.39 |

-continued

| # | Molecular Structure | Chemical Name | HPLC-MS (Method_1) |
|---|---|---|---|
| 25 | 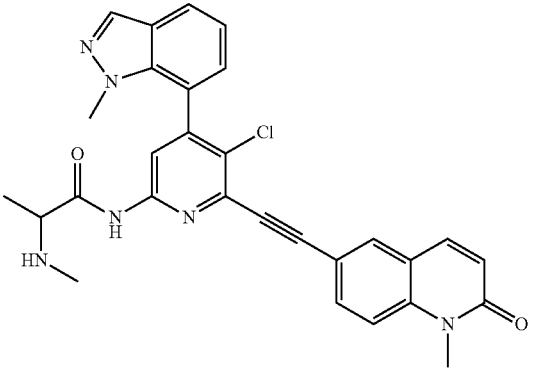 [SMILES: CNC(C)C(=O)Nc1cc(-c2cccc3cnn(C)c23)c(Cl)c(C#Cc2ccc3c(ccc(=O)n3C)c2)n1] | N-[5-chloro-4-(1-methyl-1H-indazol-7-yl)-6-[2-(1-methyl-2-oxo-1,2-dihydroquinolin-6-yl)ethynyl]pyridin-2-yl]-2-(methylamino)propanamide | M + H = 525; tR = 1.26 |
| 26 | 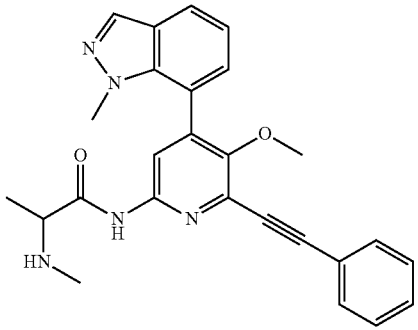 [SMILES: CNC(C)C(=O)Nc1cc(-c2cccc3cnn(C)c23)c(OC)c(C#Cc2ccccc2)n1] | N-[5-methoxy-4-(1-methyl-1H-indazol-7-yl)-6-(2-phenylethynyl)pyridin-2-yl]-2-(methylamino)propanamide | M + H = 440; tR = 1.36 |
| 27 | 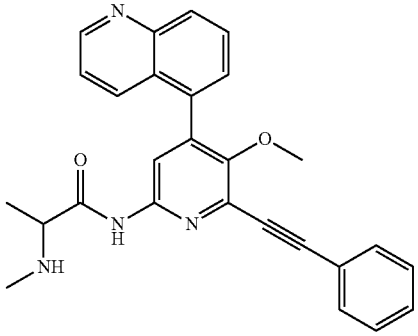 [SMILES: CNC(C)C(=O)Nc1cc(-c2cccc3ncccc23)c(OC)c(C#Cc2ccccc2)n1] | N-[5-methoxy-6-(2-phenylethynyl)-4-(quinolin-5-yl)pyridin-2-yl]-2-(methyl-amino)propanamide | M + H = 437; tR = 1.29 |
| 28 | 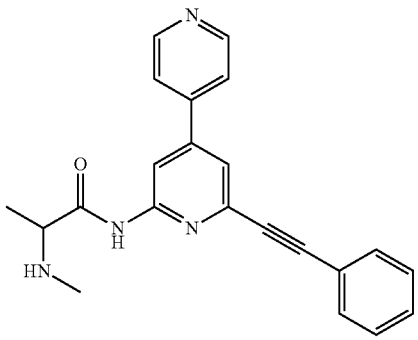 [SMILES: CNC(C)C(=O)Nc1cc(-c2ccncc2)cc(C#Cc2ccccc2)n1] | 2-(methylamino)-N-[6-(2-phenylethynyl)-4-(pyridin-4-yl)pyridin-2-yl]propanamide | M + H = 357; tR = 1.36 |

-continued

| # | Chemical Name | HPLC-MS (Method_1) |
|---|---|---|
| 29 | N-[4-(5-fluoropyridin-3-yl)-6-(2-phenylethynyl)pyridin-2-yl]-2-(methylamino)propanamide | M + H = 375; tR = 1.41 |
| 30 | 2-(methylamino)-N-[6-(2-phenylethynyl)-4-[6-(trifluoromethyl)pyridin-3-yl]pyridin-2-yl]propanamide | M + H = 425; tR = 1.55 |
| 31 | N-[4-(6-methoxypyridin-3-yl)-6-(2-phenylethynyl)pyridin-2-yl]-2-(methylamino)propanamide | M + H = 387; tR = 1.52 |
| 32 | N-[4-(2-fluorophenyl)-6-(2-phenylethynyl)pyridin-2-yl]-2-(methylamino)propanamide | M + H = 374; tR = 1.60 |

| # | Molecular Structure | Chemical Name | HPLC-MS (Method_1) |
|---|---|---|---|
| 33 | 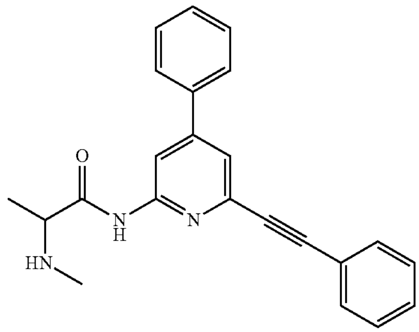 [SMILES: CNC(C)C(=O)Nc1cc(-c2ccccc2)cc(C#Cc2ccccc2)n1] | 2-(methylamino)-N-[4-phenyl-6-(2-phenylethynyl)pyridin-2-yl]propanamide | M + H = 356; tR = 1.61 |
| 34 | 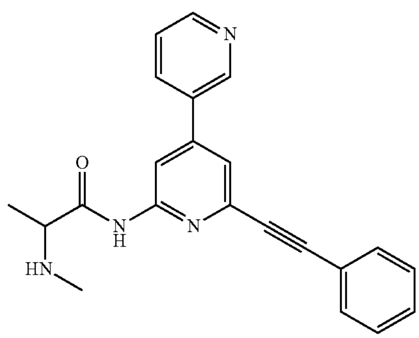 [SMILES: CNC(C)C(=O)Nc1cc(-c2cccnc2)cc(C#Cc2ccccc2)n1] | 2-(methylamino)-N-[6-(2-phenyethynyl)-4-(pyridin-3-yl)pyridin-2-yl]propanamide | M + H = 357; tR = 1.35 |

Example 35

2-(methylamino)-N-[6-(2-phenylethynyl)-4-(pyridin-4-yl)-5-(pyrimidin-5-yl)pyridin-2-yl]propanamide

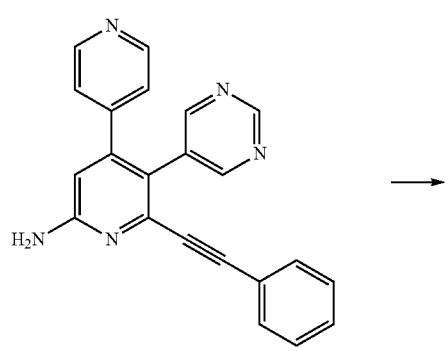

-continued

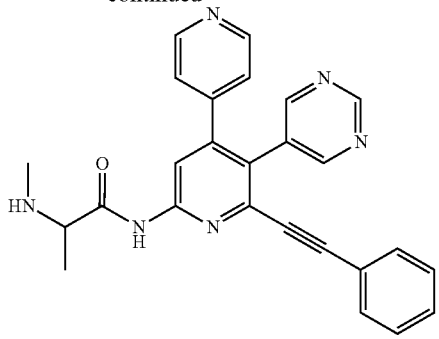

A mixture of 6-(2-phenylethynyl)-4-(pyridin-4-yl)-5-(pyrimidin-5-yl)pyridin-2-amine G9 (72 mg, 0.21 mmol), DMAP (0.05 mg, 4 μmol) and Et3N (43 μl, 0.31 mmol) in dioxane (4.3 ml) is stirred at 0° C. for 15 minutes. 2-bromopropionyl bromide (33 μl, 0.31 mmol) is added dropwise and the mixture stirred at RT for 1 h. The mixture is heated to 90° C. and stirred for 16 h. Et3N (43 μl, 0.31 mmol) and 2-Bromopropionyl bromide (33 µl, 0.31 mmol) is added and the mixture stirred for another 3 h. The mixture is cooled to RT, methylamine (2 mol/l solution in THF, 1.03 ml, 2.06 mmol) is added and the mixture stirred for 17 h. The mixture is concentrated in vacuo and the product purified by RP HPLC. Yield: 7.6 mg (9%). HPLC-MS: M+H=435; tR=.2.75 min (METHOD_6).

The following example is prepared analogously from G10:

Cooled to RT 2-bromobutanoyl bromide (29 µl, 0.24 mmol) in toluene (200 µl) is added dropwise. The mixture is stirred at 60° C. for 16 h before it is again cooled to RT. Ethanamine (aqueous solution 70 wt.-%, 1 ml) is added and the mixture stirred for 16 h at 80° C. The mixture is concentrated in vacuo and the product purified by RP HPLC. Yield: 3 mg (8%). HPLC-MS: M+H=519; tR=1.37 min (METHOD_1).

| # | Molecular Structure | Chemical Name | HPLC-MS |
|---|---|---|---|
| 36 | 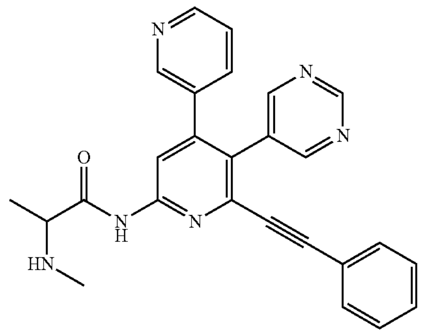 [SMILES: CNC(C)C(=O)Nc1cc(-c2cccnc2)c(-c2cncnc2)c(C#Cc2ccccc2)n1] | 2-(methylamino)-N-[6-(2-phenylethynyl)-4-(pyridin-3-yl)-5-(pyrimidin-5-yl)-pyridin-2-yl]propanamide | M + H = 435; tR = 2.59 (METHOD_7) |

Example 37

N-(4-{1,3-dimethyl-1H-pyrazolo[4,3-d]pyrimidin-7-yl}-6-[2-(1-methylisoquinolin-6-yl)ethynyl]pyridin-2-yl)-2-(ethylamino)butanamide

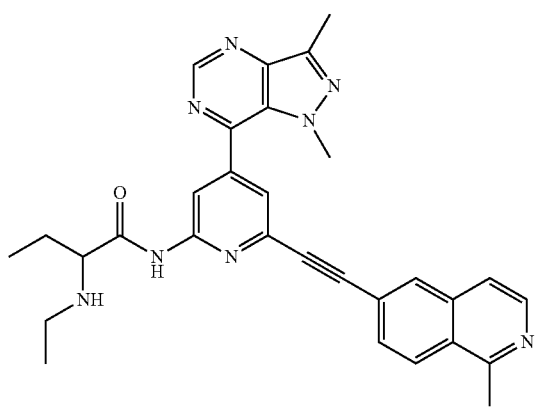 [SMILES: CCNC(CC)C(=O)Nc1cc(-c2ncnc3c(C)nn(C)c23)cc(C#Cc2ccc3c(C)nccc3c2)n1]

A mixture of tert-butyl-N-{1-[(4-{1,3-dimethyl-1H-pyrazolo[4,3-d]pyrimidin-7-yl}-6-[2-(1-methylisoquinolin-6-yl)ethynyl]pyridin-2-yl)carbamoyl]ethyl}-N-methylcarbamate H2 (150 mg, 0.31 mmol) and potassium hydroxide (1 mol/l solution in MeOH:water=2:1, 3 ml, 3 mmol) is stirred at 60° C. for 2 days. The precipitate is collected and purified by NP chromatography to yield 4-{1,3-dimethyl-1H-pyrazolo[4,3-d]pyrimidin-7-yl}-6-[2-(1-methylisoquinolin-6-yl)ethynyl]pyridin-2-amine. Yield: 110 mg (89%). HPLC-MS: M+H=406; tR=1.07 min (METHOD_1).

A mixture of 4-{1,3-dimethyl-1H-pyrazolo[4,3-d]pyrimidin-7-yl}-6-[2-(1-methylisoquinolin-6-yl)ethynyl]pyridin-2-amine (30 mg, 74 µmol), toluene (200 µl) and DIPEA (57 µl, 333 µmol) is cooled to 0° C. 2-Bromobutanoyl bromide (29 µl, 0.24 mmol) in toluene (200 µl) is added dropwise. The mixture is warmed to 50° C. and stirring is continued for 16 h.

Preparation of Additional Building Blocks K and L

Ka) 3-iodo-5-methylimidazo[1,2-a]pyridine

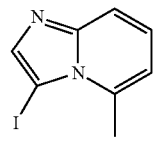

To 5-methyl-imidazo[1,2-a]pyridine (0.51 g, 3.0 mmol) in ACN (1 ml) at RT is added NIS (0.73 g, 3.3 mmol) and stirring continued for 18 h. The mixture is poured onto water. The precipitate is collected, washed with water and dried. Yield: 0.78 g (92%). HPLC-MS: M+H=259; tR=1.04 min (METHOD_1).

Kb) 7-bromo-1,2,4,6-tetramethyl-1H,2H,3H-pyrazolo[4,3-c]pyridin-3-one

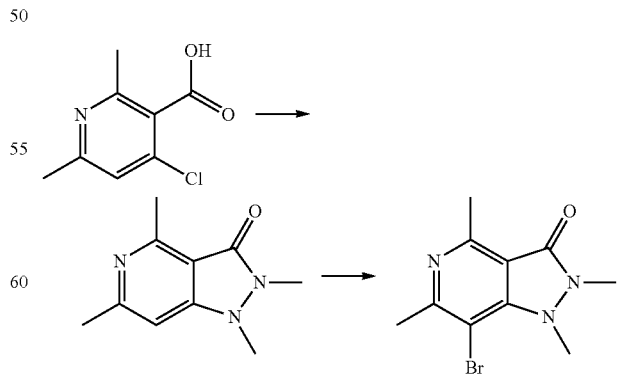

A mixture of 4-chloro-2,6-dimethyl-nicotinic acid (0.96 g, 5.2 mmol), 1,2-dimethyl-hydrazine dihydrochloride (0.83 g, 6.2 mmol), DIPEA (3.5 ml, 20.7 mmol) and NMP (5 ml) is heated in the microwave at 100° C. for 45 minutes. The mixture is diluted with DCM and extracted with a saturated aqueous sodium hydrogencarbonate solution. The combined organic layers are dried over MgSO$_4$ and concentrated in vacuo. 1,2,4,6-tetramethyl-1H,2H,3H-pyrazolo[4,3-c]pyridin-3-one is purified by RP HPLC. Yield: 0.35 g (35%). HPLC-MS: M+H=192; tR=0.28 min (METHOD_1).

A mixture of 1,2,4,6-tetramethyl-1H,2H,3H-pyrazolo[4,3-c]pyridin-3-one (0.33 g, 1.7 mmol), NBS (0.34 g, 1.9 mmol) and conc. H$_2$SO$_4$ (8 ml) is stirred at RT for 18 h. The mixture is poured onto ice-water. The water phase is made basic with an aqueous solution of sodium hydroxide (1 mol/l) and extracted with DCM. The combined organic layers are dried over MgSO$_4$ and concentrated in vacuo. 7-bromo-1,2,4,6-tetramethyl-1H,2H,3H-pyrazolo[4,3-c]pyridin-3-one is used without further purification. Yield: 0.37 g (80%). HPLC-MS: M+H=270/272; tR=0.77 min (METHOD_1).

Kc) N'-(5-acetyl-6-chloro-2-methylpyrimidin-4-yl)-N-methyl(tert-butoxy)-carbohydrazide

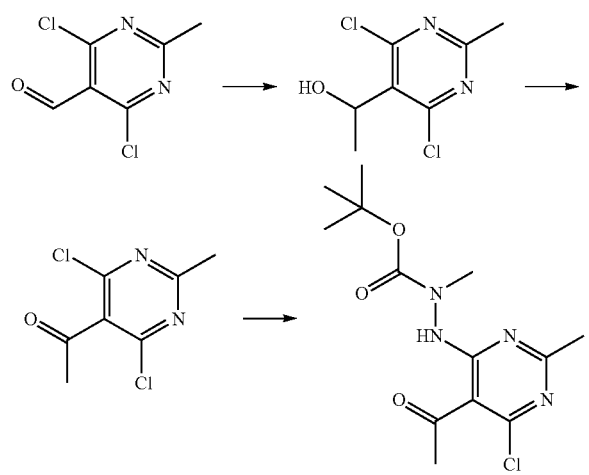

A solution of methyl methylmagnesium bromide (1.4 mol/l solution in toluene:THF=3:1, 0.13 mol) is added to 4,6-dichloro-2-methylpyrimidine-5-carbaldehyde (20 g, 0.105 mol) in THF (100 ml) at 0° C. under inert atmosphere. The mixture is stirred for 10 minutes, gradually warmed to RT and stirred for another 30 minutes. The mixture is diluted with water and extracted with EtOAc. The combined organic layers are washed with water and brine, dried over MgSO$_4$ and concentrated in vacuo. The crude 1-(4,6-dichloro-2-methylpyrimidin-5-yl)ethan-1-ol is used without further purification. Yield: 15 g (69%).

A mixture of 1-(4,6-dichloro-2-methylpyrimidin-5-yl)ethan-1-ol (15 g, 72 mmol), in DCM (113 mml) is cooled to 0° C. 1,1,1-tris (acetyloxy)-1,1-dihydro-1,2-benziodoxol-3-(1H)-one (33.8 g, 80 mmol) is added and stirring continued for 4 h. The mixture is filtered and washed with a saturated aqueous sodium hydrogencarbonate solution. The combined organic layers are dried over MgSO$_4$ and concentrated under reduced pressure. The crude 1-(4,6-dichloro-2-methylpyrimidin-5-yl)ethan-1-one is used without further purification. Yield: 10 g (67%).

To 1-(4,6-dichloro-2-methylpyrimidin-5-yl)ethan-1-one (0.5 g, 2.4 mmol) in DMF (2 ml) is added 1-boc-1-methylhydrazine (0.36 g, 2.4 mmol). DIPEA (0.5 ml, 2.9 mmol) is added and the mixture stirred at 50° C. for 18 h. The mixture is concentrated in vacuo and N'-(5-acetyl-6-chloro-2-methylpyrimidin-4-yl)-N-methyl(tert-butoxy)carbohydrazide purified by RP HPLC. Yield: 0.57 g (74%). HPLC-MS: M+H=315; tR=0.89 min (METHOD_3).

La) 6-iodo-1-methylisoquinoline

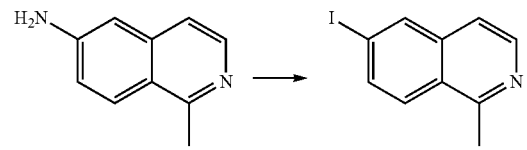

A mixture of 1-methylisoquinolin-6-amine (0.25 g, 1.6 mmol) in 2-methylpropan-2-ol (15 ml) and hydrochloric acid (2 mol/l, 15 ml) is cooled to 0° C. Sodium nitrite (0.11 g, 1.6 mmol) is added and stirring continued for 30 minutes. The mixture is warmed to RT and stirred for 5 minutes before it is cooled to 0° C. once more. Sodium iodide (0.42 g, 2.8 mmol) is added and the mixture stirred at RT for 1 h. The mixture is diluted with water and extracted with EtOAc. The aqueous phase is made basic with sodium hydroxide and extracted with EtOAc again. The combined organic layers are washed with an aqueous solution of sodium thiosulfate (10 wt.-%), dried over MgSO$_4$ and concentrated in vacuo. The product is purified by RP HPLC. Yield: 54 mg (13%). HPLC-MS: M+H=270; tR=1.70 min (METHOD_4).

Biological Methods

XIAP BIR3 and cIAP1 BIR3 Binding Assays (DELFIA)

BIR3 domains of human XIAP (covering amino acids 241 to 356; XIAP BIR3) and cIAP1 (covering amino acids 256 to 363; cIAP1 BIR3) were expressed and purified from E. coli as GST-fusion proteins. Peptide AVPIAQKSE-Lys(Biotin), representing the N-terminus of mature human SMAC(SMAC peptide), was used as interaction partner in the protein-peptide interaction assay.

BIR3 domains (10 nM) were incubated with SMAC peptide (10 nM) in assay buffer (50 mM Tris, 120 mM NaCl, 0.1% BSA, 1 mM DTT, 0.05% TritonX100) for one hour at room temperature in the presence of inhibitory compounds. The assay mixture was transferred to a strepatvidin coated plate and incubated for one hour at room temperature to allow binding of the biotinylated peptide and associated BIR3 domains to the plate. After several washing steps Eu labeled anti-GST antibody (e.g. Perkin Elmer DELFIA Eu-N1-antiGST AD0250) was added to detect BIR3 domain-SMAC peptide interactions according to Perkin Elmer's instructions. Briefly, the antibody was added (dilution 1:5000 in Perkin Elmer DELFIA Assay Buffer 2013-01) and incubated for one hour. After 3 washing steps using Delfia Washing Buffer (Perkin Elmer DELFIA Wash 2013-05), Enhancement Solution (Perkin Elmer Enhancement Asolution 2013-02) was added and incubation continued for 10 minutes. Time resolved Europium fluorescence was measured in a Wallac Victor using Standard assay settings.

IC$_{50}$ values for inhibitory compounds were calculated from assay results obtained by incubating BIR3 domains with SMAC peptide in the presence of serially diluted compounds (e.g. 1:5). DELFIA assay results were plotted against compound concentrations and Software GraphPad Prizm was used to calculate half maximal inhibitory concentrations (IC$_{50}$ values).

The IC$_{50}$ values representing the biological activity of the examples are listed in the tables below. All IC$_{50}$ values are reported in nM and represent the activity of the (S)-isomer (examples 1-34, 38-43) or the racemate (examples 35-37):

| # | XIAP BIR-3 | cIAP1 BIR-3 |
|---|---|---|
| 1 | 72 | 1 |
| 2 | 123 | 1 |
| 3 | 70 | 1 |
| 4 | 95 | 1 |
| 5 | 79 | 59 |
| 6 | 50 | 1 |
| 7 | 12 | 2 |
| 8 | 222 | 1 |
| 9 | 94 | 2 |
| 10 | 26 | 2 |
| 11 | 57 | 1 |
| 12 | 2050 | 11 |
| 13 | 143 | 1 |
| 14 | 29 | 1 |
| 15 | 247 | 1 |
| 16 | 151 | 1 |
| 17 | 58 | 1 |
| 18 | 42 | 1 |
| 19 | 299 | 2 |
| 20 | 50 | 1 |
| 21 | 158 | 1 |
| 22 | 10 | 1 |
| 23 | n.a. | n.a. |
| 24 | 5402 | 12 |
| 25 | n.a. | 10 |
| 26 | 129 | 12 |
| 27 | 99 | 136 |
| 28 | 350 | 282 |
| 29 | 840 | 127 |
| 30 | 1811 | 352 |
| 31 | 711 | 325 |
| 32 | 10250 | 4010 |
| 33 | 5492 | 2642 |
| 34 | 485 | 250 |
| 35 | 103 | 250 |
| 36 | 100 | 172 |
| 37 | 2879 | 6 |
| 38 | 131 | 1 |
| 39 | 57 | 1 |
| 40 | 55 | 1 |
| 41 | 105 | 1 |
| 42 | 73 | 1 |
| 43 | 231 | 1 |

On the basis of their biological properties the compounds of general formula (I) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancers, which may be treated with compounds according to the invention, are lung, liver, colon, brain, breast, ovary, prostate cancer, pancreas, kidney, stomach, head, neck and urothelial cancer, as well as lymphoma and leukemia.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4, 3-alethine, 131-I-TM-601, 3CPA, 7-ethyl-10-hydroxy-camptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992, BIBF 1120, bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-100, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhuMAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (I)

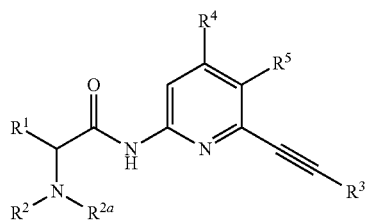

wherein,
R$^1$ is —C$_{1-3}$alkyl, —C$_{1-3}$haloalkyl or —H;
R$^2$ is —C$_{1-3}$alkyl or —H;
R$^{2a}$ is —C$_{1-3}$alkyl or —H;
R$^3$ is phenyl or 5-12 membered heteroaryl, each of which is optionally substituted with one or more independently selected R$^6$ groups, or
R$^3$ is 8-12 membered aromatic heterocyclyl, optionally substituted with one or more moieties independently selected from the group consisting of =O and R$^6$;
R$^4$ is phenyl or 5-12 membered heteroaryl, each of which is optionally substituted with one or more independently selected R$^7$ groups, or
R$^4$ is 8-12 membered aromatic heterocyclyl, optionally substituted with one or more moieties independently selected from the group consisting of =O and R$^7$;
R$^5$ is —H, halogen, —O—C$_{1-3}$alkyl or 5-6 membered heteroaryl;
R$^6$ is halogen, —C$_{1-3}$alkyl, —O—C$_{1-3}$alkyl, cyano, or 5-6 membered heteroaryl, wherein the heteroaryl group is optionally substituted with —C$_{1-3}$alkyl, —O—C$_{1-3}$alkyl or halogen; and
R$^7$ is halogen, —C$_{1-3}$ alkyl, —C$_{1-3}$haloalkyl and —O—C$_{1-3}$ alkyl or cyano;
or a pharmaceutically acceptable salt thereof.

2. A compound according to claim 1, wherein R$^1$ is —CH$_3$ or —CH$_2$CH$_3$.

3. A compound according to claim 1, wherein R$^2$ is —CH$_3$ or —CH$_2$CH$_3$.

4. A compound according to claim 1, wherein R$^{2a}$ is —H.

5. A compound according to claim 1, wherein R$^3$ is phenyl,

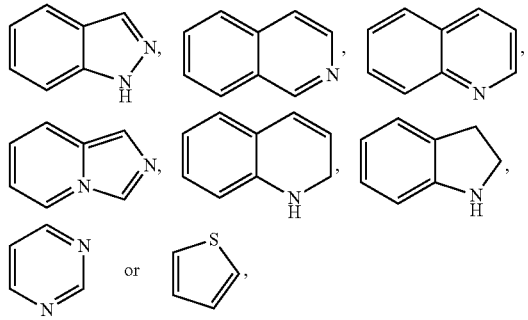

each of which groups is optionally substituted as defined in claim 1.

6. A compound according to claim 1, wherein R$^3$ is phenyl,

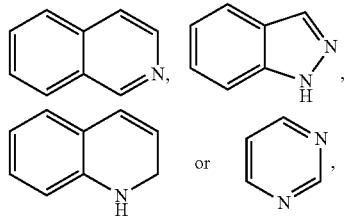

each of which groups is optionally substituted as defined in claim 1.

7. A compound according to claim 1, wherein R$^3$ is phenyl,

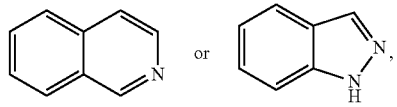 [SMILES: c1ccc2cnccc2c1 ; c1ccc2[nH]ncc2c1]

each of which groups is optionally substituted as defined in claim 1.

8. A compound according to claim 1, wherein R$^4$ is phenyl, pyridyl,

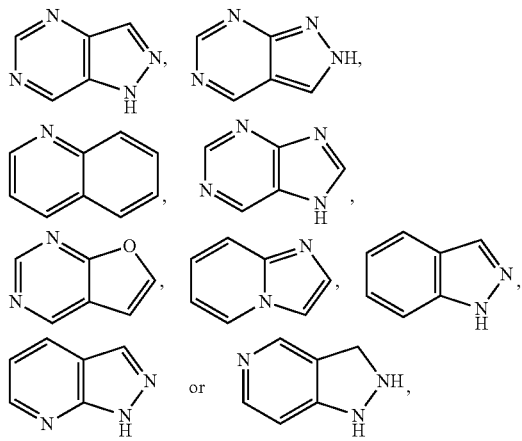

each of which groups is optionally substituted as defined in claim 1.

9. A compound according to claim 1, wherein R⁴ is phenyl, pyridyl,

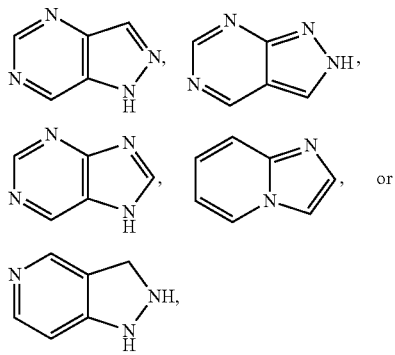

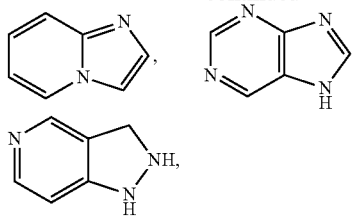

or each of which groups is optionally substituted as defined in claim 1.

11. A compound according to claim 1, wherein R⁵ is —H, —Cl, —O—CH₃ or pyrimidinyl.

12. A compound according to claim 11, wherein R⁵ is —H.

13. A compound according to claim 1, wherein R³ is substituted with =O or R⁶, wherein R⁶ is —F, —CH₃, —O—CH₃, or

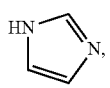

which imidazole is optionally substituted with —CH₃.

14. A compound according to claim 1, wherein R⁴ is substituted with =O or R⁷, wherein R⁷ is —F, —CH₃ or —O—CH₃.

15. A compound according to claim 1 selected from the group consisting of

10. A compound according to claim 1, wherein R⁴ is

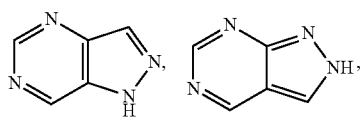

| EX # | Structure | Ex # | Structure |
|---|---|---|---|
| 1 | 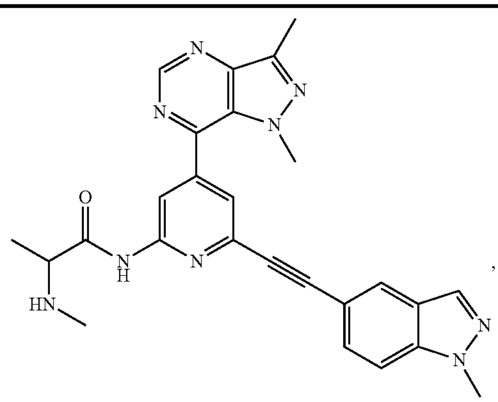 | 2 | 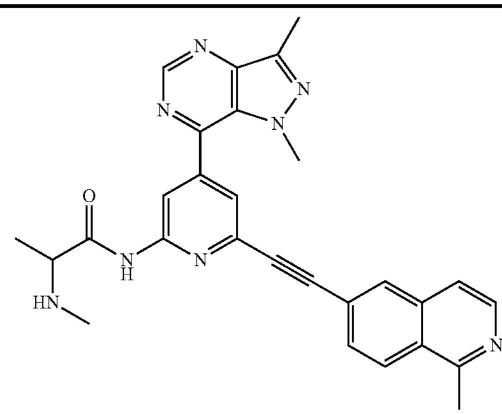 |
| 3 | 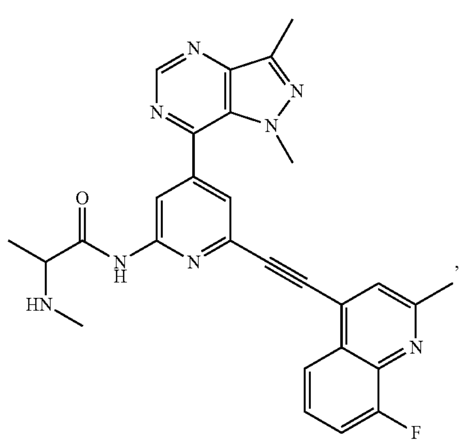 [SMILES: CNC(C)C(=O)Nc1cc(-c2ncnc3c(C)nn(C)c23)cc(C#Cc2cc(C)nc3c(F)cccc23)n1] | 4 | 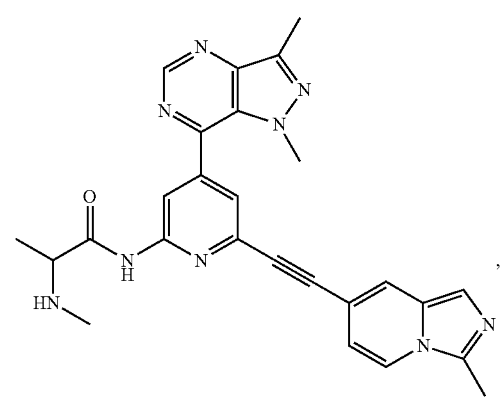 [SMILES: CNC(C)C(=O)Nc1cc(-c2ncnc3c(C)nn(C)c23)cc(C#Cc2ccn3c(C)ncc3c2)n1] |

-continued

| EX # | Structure | Ex # | Structure |
|---|---|---|---|
| 5 | 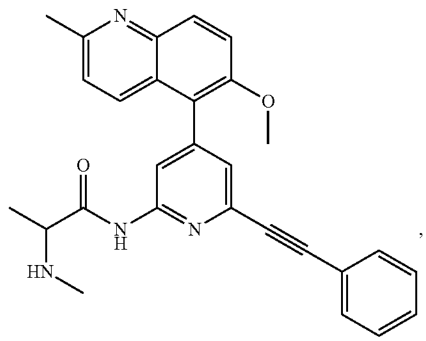 [SMILES: CNC(C)C(=O)Nc1cc(-c2c(OC)ccc3nc(C)ccc23)cc(C#Cc2ccccc2)n1] | 6 | 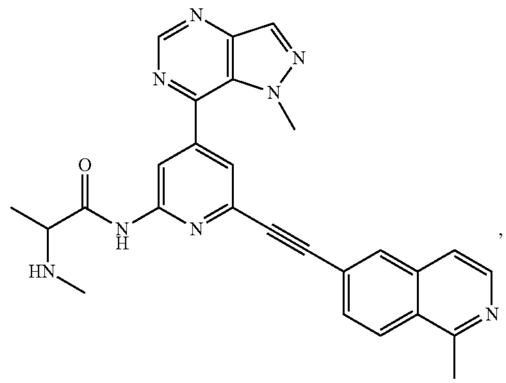 [SMILES: CNC(C)C(=O)Nc1cc(-c2ncnc3cnn(C)c23)cc(C#Cc2ccc3c(C)nccc3c2)n1] |
| 7 | 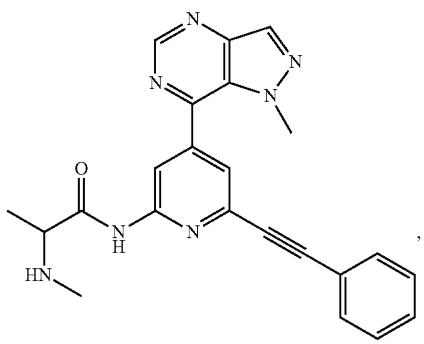 [SMILES: CNC(C)C(=O)Nc1cc(-c2ncnc3cnn(C)c23)cc(C#Cc2ccccc2)n1] | 8 | 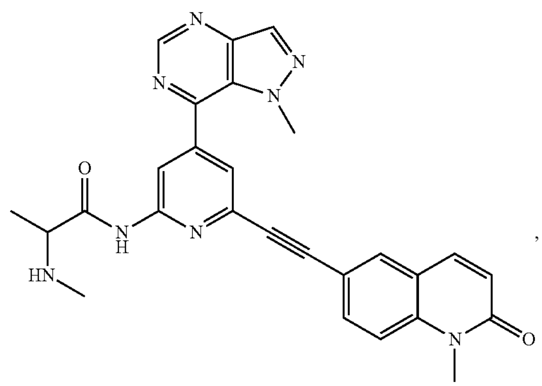 [SMILES: CNC(C)C(=O)Nc1cc(-c2ncnc3cnn(C)c23)cc(C#Cc2ccc3c(ccc(=O)n3C)c2)n1] |
| 9 | 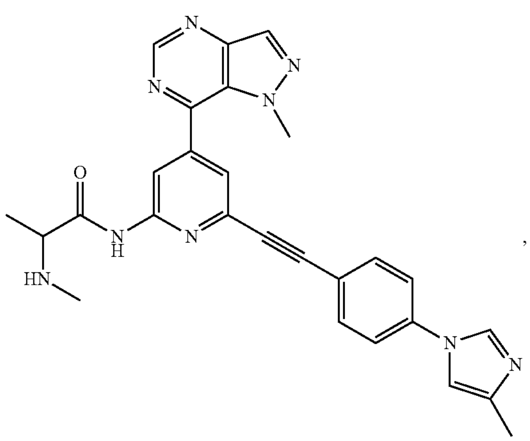 [SMILES: CNC(C)C(=O)Nc1cc(-c2ncnc3cnn(C)c23)cc(C#Cc2ccc(-n3cnc(C)c3)cc2)n1] | 10 | 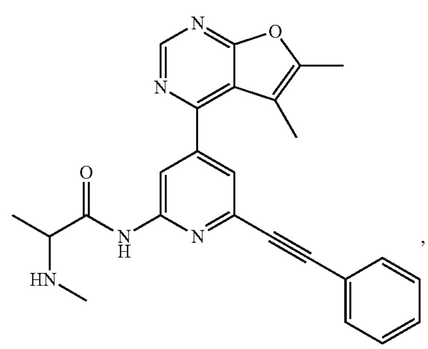 [SMILES: CNC(C)C(=O)Nc1cc(-c2ncnc3oc(C)c(C)c23)cc(C#Cc2ccccc2)n1] |
| 11 | 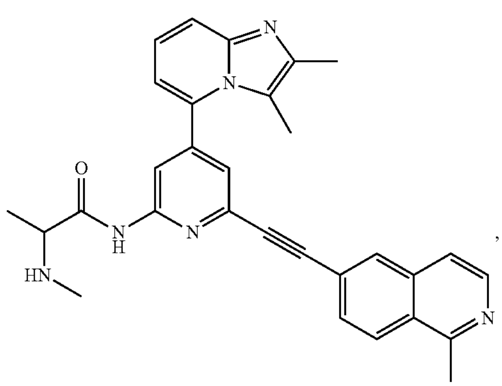 [SMILES: CNC(C)C(=O)Nc1cc(-c2cccc3nc(C)c(C)n23)cc(C#Cc2ccc3c(C)nccc3c2)n1] | 12 | 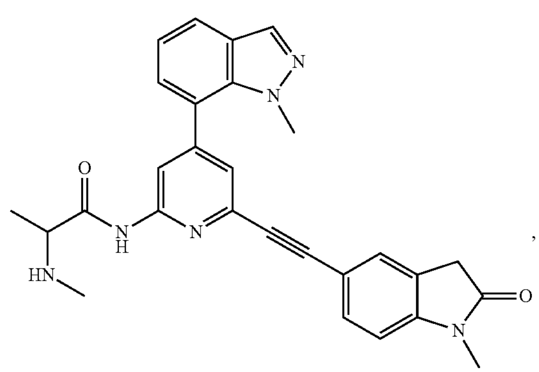 [SMILES: CNC(C)C(=O)Nc1cc(-c2cccc3cnn(C)c23)cc(C#Cc2ccc3c(c2)CC(=O)N3C)n1] |

-continued

| EX # | Structure | Ex # | Structure |
|---|---|---|---|
| 13 | 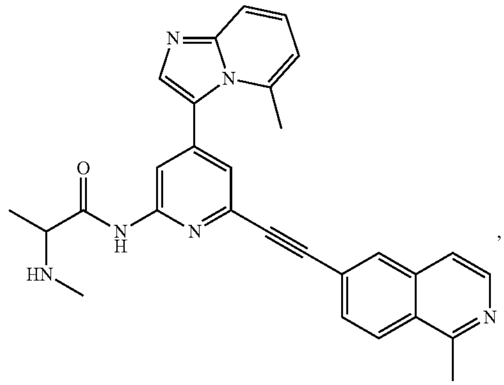 [SMILES: CNC(C)C(=O)Nc1cc(-c2cnc3cccc(C)n23)cc(C#Cc2ccc3c(C)nccc3c2)n1] | 14 | 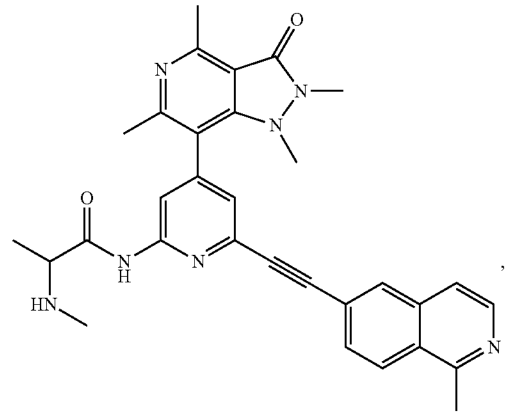 [SMILES: CNC(C)C(=O)Nc1cc(-c2c(C)nc(C)c3c(=O)n(C)n(C)c23)cc(C#Cc2ccc3c(C)nccc3c2)n1] |
| 15 | 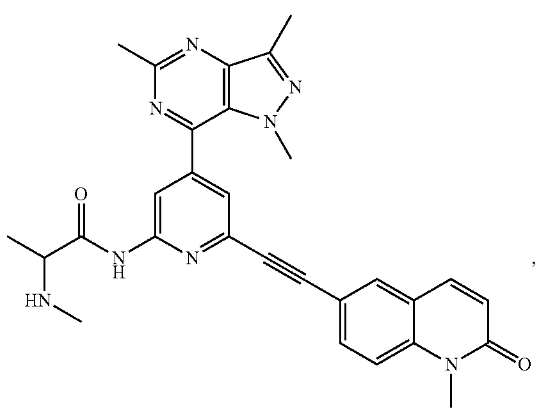 [SMILES: CNC(C)C(=O)Nc1cc(-c2nc(C)nc3c(C)nn(C)c23)cc(C#Cc2ccc3c(ccc(=O)n3C)c2)n1] | 16 | 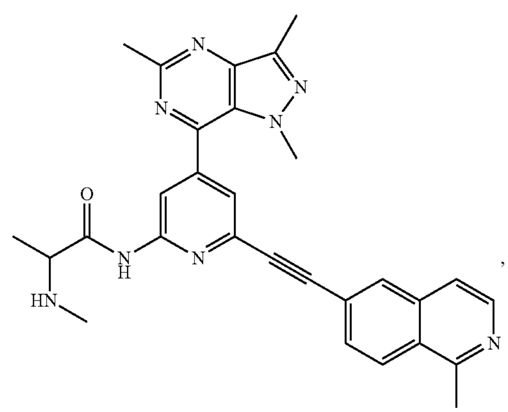 [SMILES: CNC(C)C(=O)Nc1cc(-c2nc(C)nc3c(C)nn(C)c23)cc(C#Cc2ccc3c(C)nccc3c2)n1] |
| 17 | 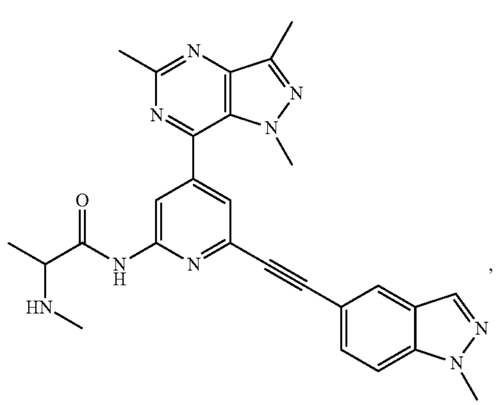 [SMILES: CNC(C)C(=O)Nc1cc(-c2nc(C)nc3c(C)nn(C)c23)cc(C#Cc2ccc3c(cnn3C)c2)n1] | 18 | 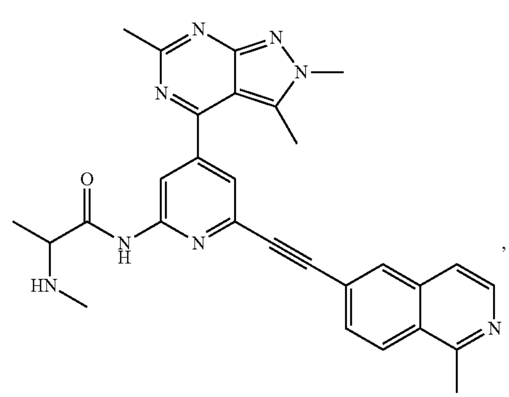 [SMILES: CNC(C)C(=O)Nc1cc(-c2nc(C)nc3nn(C)c(C)c23)cc(C#Cc2ccc3c(C)nccc3c2)n1] |

-continued

| EX # | Structure | Ex # | Structure |
|---|---|---|---|
| 19 | 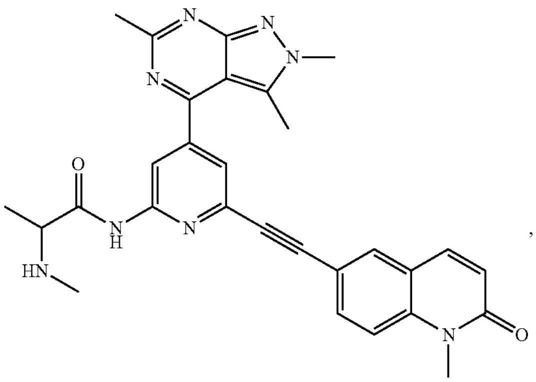 [SMILES: CNC(C)C(=O)Nc1cc(-c2nc(C)nc3nn(C)c(C)c23)cc(C#Cc2ccc3c(ccc(=O)n3C)c2)n1] | 20 | 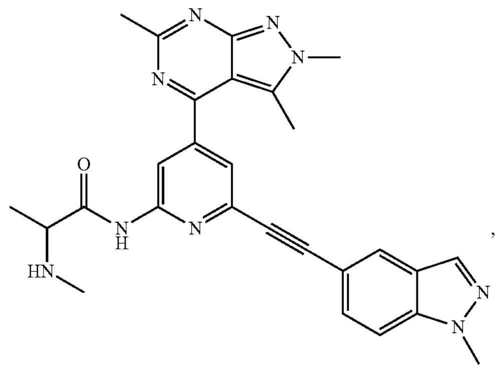 [SMILES: CNC(C)C(=O)Nc1cc(-c2nc(C)nc3nn(C)c(C)c23)cc(C#Cc2ccc3c(cnn3C)c2)n1] |
| 21 | 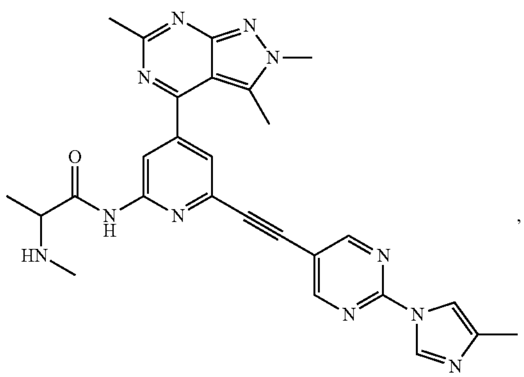 [SMILES: CNC(C)C(=O)Nc1cc(-c2nc(C)nc3nn(C)c(C)c23)cc(C#Cc2cnc(-n3cnc(C)c3)nc2)n1] | 22 | 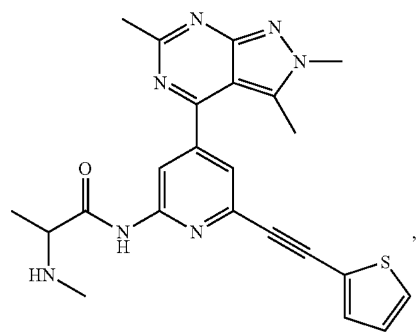 [SMILES: CNC(C)C(=O)Nc1cc(-c2nc(C)nc3nn(C)c(C)c23)cc(C#Cc2cccs2)n1] |
| 23 | 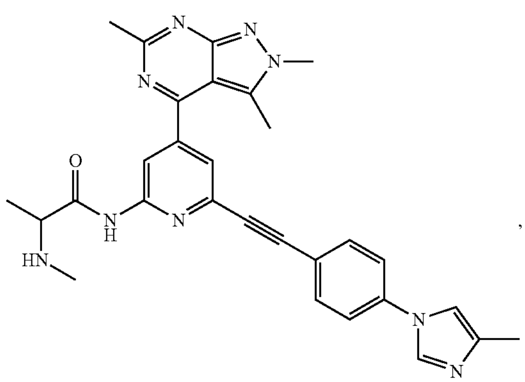 [SMILES: CNC(C)C(=O)Nc1cc(-c2nc(C)nc3nn(C)c(C)c23)cc(C#Cc2ccc(-n3cnc(C)c3)cc2)n1] | 24 | 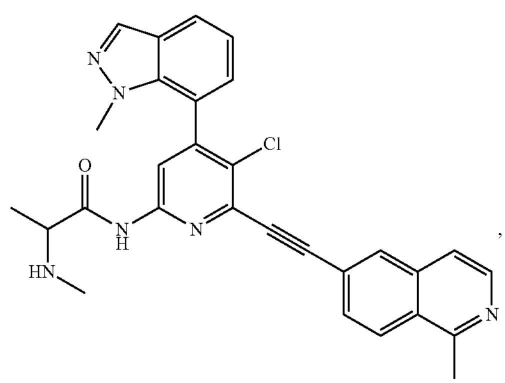 [SMILES: CNC(C)C(=O)Nc1cc(-c2cccc3cnn(C)c23)c(Cl)c(C#Cc2ccc3c(C)nccc3c2)n1] |
| 25 | 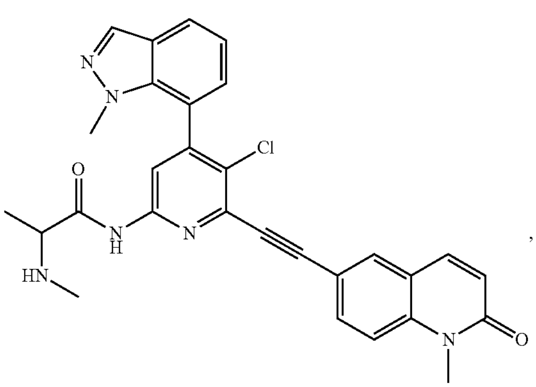 [SMILES: CNC(C)C(=O)Nc1cc(-c2cccc3cnn(C)c23)c(Cl)c(C#Cc2ccc3c(ccc(=O)n3C)c2)n1] | 26 | 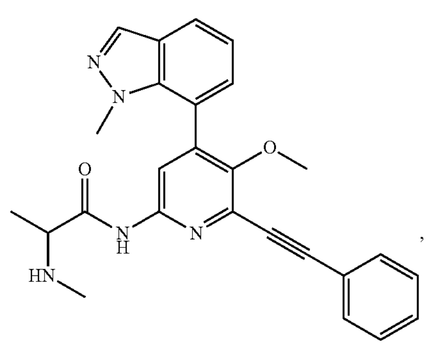 [SMILES: CNC(C)C(=O)Nc1cc(-c2cccc3cnn(C)c23)c(OC)c(C#Cc2ccccc2)n1] |

-continued

| EX # | Structure | Ex # | Structure |
|---|---|---|---|
| 27 | 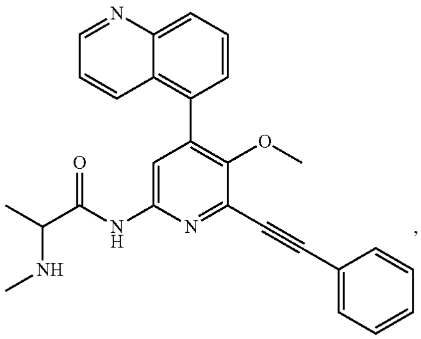 [SMILES: CNC(C)C(=O)Nc1cc(-c2cccc3ncccc23)c(OC)c(C#Cc2ccccc2)n1] | 28 | 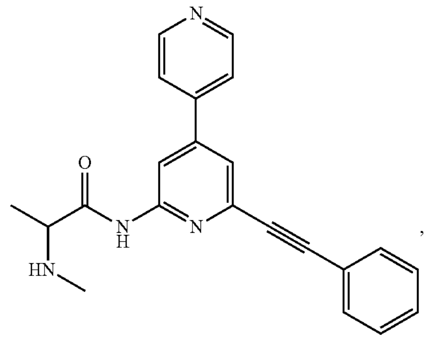 [SMILES: CNC(C)C(=O)Nc1cc(-c2ccncc2)cc(C#Cc2ccccc2)n1] |
| 29 | 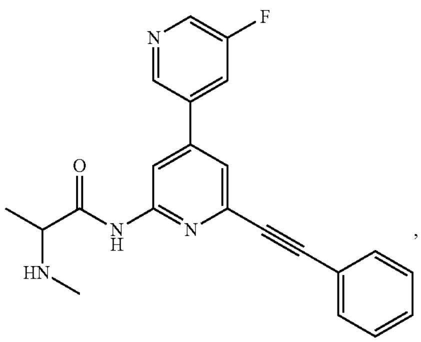 [SMILES: CNC(C)C(=O)Nc1cc(-c2cncc(F)c2)cc(C#Cc2ccccc2)n1] | 30 | 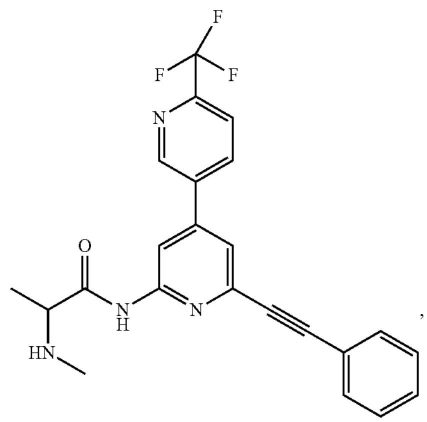 [SMILES: CNC(C)C(=O)Nc1cc(-c2ccc(C(F)(F)F)nc2)cc(C#Cc2ccccc2)n1] |
| 31 | 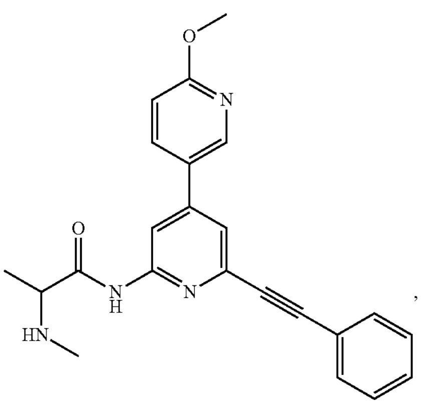 [SMILES: CNC(C)C(=O)Nc1cc(-c2ccc(OC)nc2)cc(C#Cc2ccccc2)n1] | 32 | 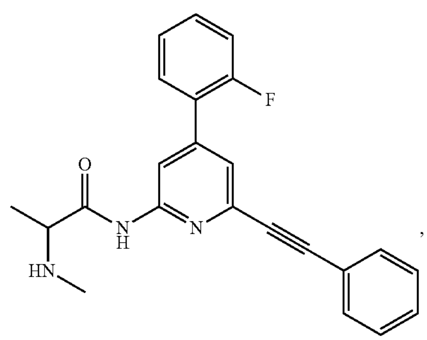 [SMILES: CNC(C)C(=O)Nc1cc(-c2ccccc2F)cc(C#Cc2ccccc2)n1] |
| 33 | 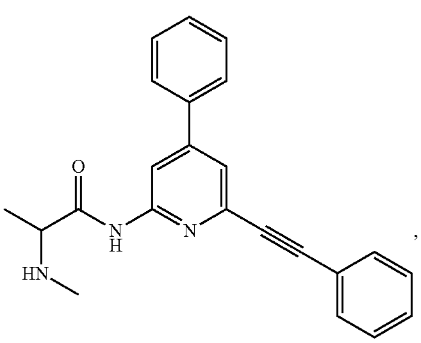 [SMILES: CNC(C)C(=O)Nc1cc(-c2ccccc2)cc(C#Cc2ccccc2)n1] | 34 | 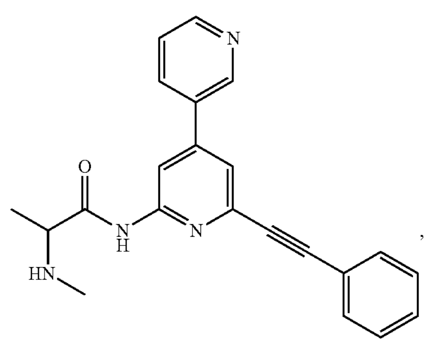 [SMILES: CNC(C)C(=O)Nc1cc(-c2cccnc2)cc(C#Cc2ccccc2)n1] |

-continued

| EX # | Structure | Ex # | Structure |
|---|---|---|---|
| 35 | 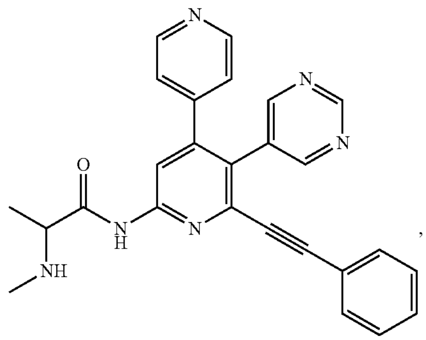 [SMILES: CNC(C)C(=O)Nc1cc(-c2ccncc2)c(-c2cncnc2)c(C#Cc2ccccc2)n1] | 36 | 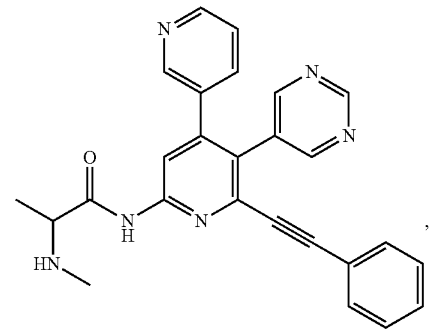 [SMILES: CNC(C)C(=O)Nc1cc(-c2cccnc2)c(-c2cncnc2)c(C#Cc2ccccc2)n1] |
| 37 | 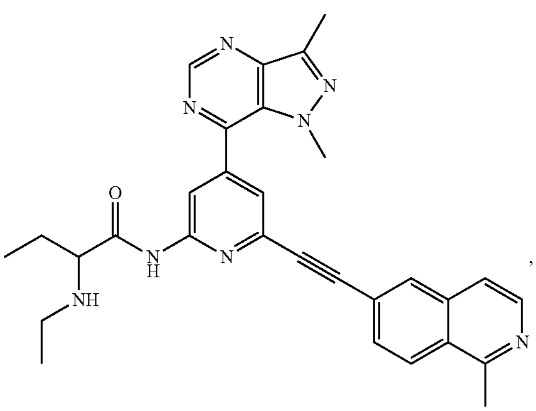 [SMILES: CCNC(CC)C(=O)Nc1cc(-c2ncnc3c(C)nn(C)c23)cc(C#Cc2ccc3c(C)nccc3c2)n1] | 38 | 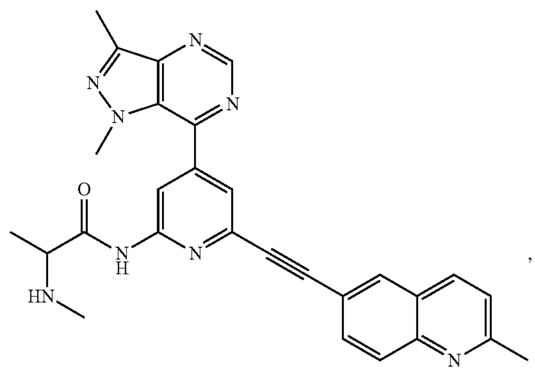 [SMILES: CNC(C)C(=O)Nc1cc(-c2ncnc3c(C)nn(C)c23)cc(C#Cc2ccc3nc(C)ccc3c2)n1] |
| 39 | 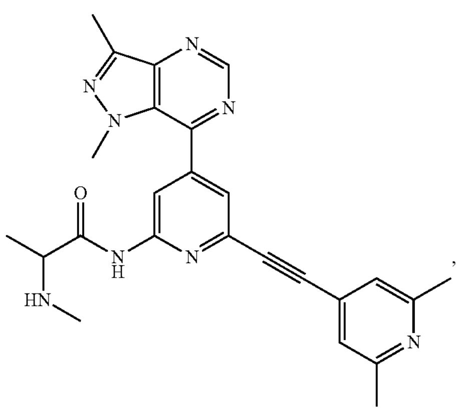 [SMILES: CNC(C)C(=O)Nc1cc(-c2ncnc3c(C)nn(C)c23)cc(C#Cc2cc(C)nc(C)c2)n1] | 40 | 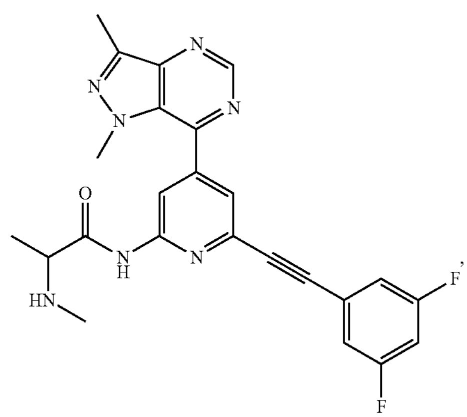 [SMILES: CNC(C)C(=O)Nc1cc(-c2ncnc3c(C)nn(C)c23)cc(C#Cc2cc(F)cc(F)c2)n1] |
| 41 | 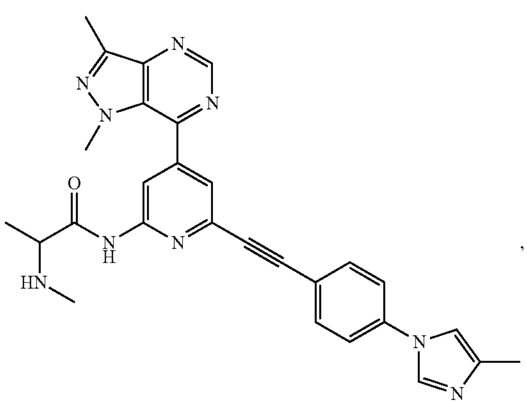 [SMILES: CNC(C)C(=O)Nc1cc(-c2ncnc3c(C)nn(C)c23)cc(C#Cc2ccc(-n3cnc(C)c3)cc2)n1] | 42 | 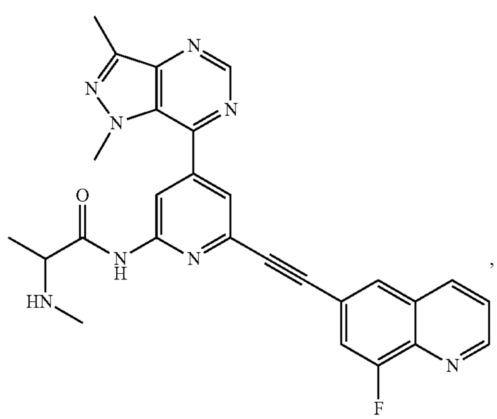 [SMILES: CNC(C)C(=O)Nc1cc(-c2ncnc3c(C)nn(C)c23)cc(C#Cc2cc(F)c3ncccc3c2)n1] |

| EX # | Structure | Ex # | Structure |
|---|---|---|---|
| | and | 43 | 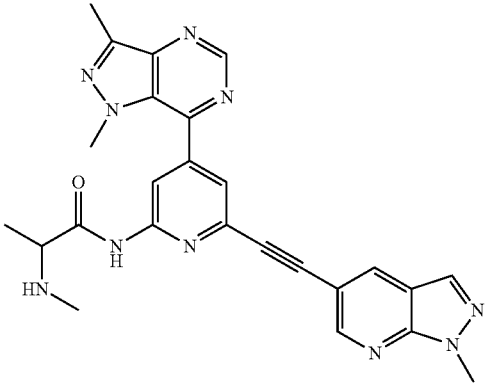 [SMILES: CNC(C)C(=O)Nc1cc(-c2ncnc3c(C)nn(C)c23)cc(C#Cc2cnc3c(cnn3C)c2)n1] |
or a pharmaceutically acceptable salt thereof.
16. A pharmaceutical composition comprising a compound according to claim 1 and a pharmaceutically acceptable carrier.
* * * * *